(12) United States Patent
Rice et al.

(10) Patent No.: US 8,372,851 B2
(45) Date of Patent: Feb. 12, 2013

(54) PYRAZOLO PYRIMIDINES AS CASEIN KINASE II (CK2) MODULATORS

(75) Inventors: Kenneth D. Rice, San Rafael, CA (US);
Joerg Bussenius, Foster City, CA (US);
Simona Costanzo, Emerald Hills, CA (US); Abigail R. Kennedy, Oakland, CA (US); Angie Inyoung Kim, San Mateo, CA (US); Jean-Claire Limun Manalo, Daly City, CA (US); Csaba J. Peto, Alameda, CA (US)

(73) Assignee: Exelixis, Inc., South San Francisco, CA (US)

( * ) Notice: Subject to any disclaimer, the term of this patent is extended or adjusted under 35 U.S.C. 154(b) by 673 days.

(21) Appl. No.: 12/083,669

(22) PCT Filed: Oct. 23, 2006

(86) PCT No.: PCT/US2006/041506
§ 371 (c)(1),
(2), (4) Date: Feb. 11, 2010

(87) PCT Pub. No.: WO2007/048066
PCT Pub. Date: Apr. 26, 2007

(65) Prior Publication Data
US 2010/0130488 A1    May 27, 2010

Related U.S. Application Data

(60) Provisional application No. 60/729,348, filed on Oct. 21, 2005.

(51) Int. Cl.
*A01N 43/90* (2006.01)
*A61K 31/519* (2006.01)
*C07D 487/00* (2006.01)

(52) U.S. Cl. .................................. 514/259.3; 544/281

(58) Field of Classification Search .................. None
See application file for complete search history.

(56) References Cited

U.S. PATENT DOCUMENTS
2005/0282827 A1    12/2005    Goetschi et al.

FOREIGN PATENT DOCUMENTS
JP    06 298752 A    10/1925

OTHER PUBLICATIONS

Ishibashi, M., et al., "Casein Kinase II Inhibitors Isolated from Two Brazilian Plants *Hymenaea parvifolia* and *Wulffia baccata*," Bioorganic & Medicinal Chemistry Letters, vol. 9, pp. 2157-2160, (1999).
Database Chemcats Apr. 25, 2003, Database accession No. 2004:1990881.
Database Chemcats Apr. 25, 2003, Database accession No. 2004:1990880.
Database Chemcats Apr. 25, 2003, Database accession No. 2004:1990879.
Database Chemcats Apr. 25, 2003, Database accession No. 2004:1990878.
Database Chemcats Apr. 25, 2003, Database accession No. 2004:1990877.
Database Chemcats Apr. 25, 2003, Database accession No. 2004:1990876.
Database Chemcats Apr. 25, 2003, Database accession No. 2004:1990872.
Database Chemcats Apr. 25, 2003, Database accession No. 2004:1990801.
Database Chemcats Apr. 25, 2003, Database accession No. 2004:1990800.
Database Chemcats Apr. 25, 2003, Database accession No. 2004:1982450.

*Primary Examiner* — Jeffrey Murray
(74) *Attorney, Agent, or Firm* — McDonnell Boehnen Hulbert & Berghoff LLP

(57) ABSTRACT

A compound according to Formula (I) or a pharmaceutically acceptable salt thereof, wherein $R^1$, $R^2$, $R^6$, $R^7$ and Z are as defined in the specification; pharmaceutical compositions thereof; and methods of use thereof.

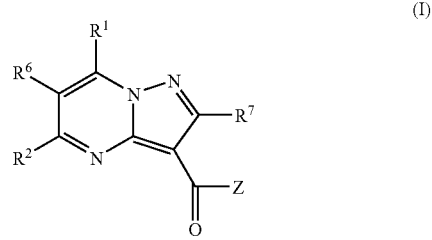

12 Claims, No Drawings

PYRAZOLO PYRIMIDINES AS CASEIN KINASE II (CK2) MODULATORS

CROSS REFERENCE TO RELATED APPLICATIONS

This application claims priority to U.S. Provisional Application Ser. No. 60/729,348, filed Oct. 21, 2005.

BACKGROUND OF THE INVENTION

1. Field of the Invention

This invention relates to the field of protein kinases and inhibitors thereof. In particular, the invention relates to inhibitors of Casein kinase II (CK2) pathways.

2. Summary of the Related Art

Casein kinase II (CK2) is a highly conserved, ubiquitously expressed protein serine/threonine kinase that phosphorylates acidic proteins such as casein. It has a tetrameric α(2)/β(2) structure. The alpha subunit possesses catalytic activity, and the beta subunit is autophosphorylated in vitro. While consideration of CK2 as a tetrameric complex remains relevant, significant evidence has emerged to challenge the view that its individual subunits exist exclusively within these complexes (Bibby et al (2005) Int J Biol Sci. 1:67-79). Circumscribed as having a vast array of substrates located in a number of cellular compartments, CK2 has been implicated in critical cellular processes such as proliferation, apoptosis, differentiation, and transformation (Olsten et al (2004) Biochem Cell Biol. 82:681-93).

Thus, there is a need for novel compounds that specifically inhibit, regulate and/or modulate kinases, particularly Casein kinase II (CK2), in order to treat, prevent, and/or inhibit diseases and conditions that involve critical cellular processes such as proliferation, apoptosis, differentiation, and transformation, such as cancers.

SUMMARY OF THE INVENTION

The invention relates to compounds and pharmaceutical compositions of the compounds for inhibiting CK2.

One aspect of the invention relates to compounds that inhibit CK2 function. The compounds are exemplified by Formula I as described herein.

Another aspect of the invention relates to a pharmaceutical composition comprising a compound according Formula I and a pharmaceutically acceptable carrier, excipient, or diluent.

Another aspect of the invention relates to a method of inhibiting CK2 in a cell, comprising contacting the cell, in which inhibition of CK2 is desired, with a compound according to Formula I Another aspect of the invention relates to a method of inhibiting CK2 in a cell, comprising contacting a cell in which inhibition of CK2 is desired with a pharmaceutical composition comprising a compound according to Formula I and a pharmaceutically acceptable carrier, excipient, or diluent.

Another aspect of the invention relates to a method of treating a disease or condition that involves CK2 comprising administering to a patient, in need of said treatment, a compound according to Formula I.

Another aspect of the invention relates to a method of treating a disease or condition that involves CK2 comprising administering to a patient, in need of said treatment, a pharmaceutical composition comprising a compound according to Formula I and a pharmaceutically acceptable carrier, excipient, or diluent.

The disease or condition that can be treated by the compounds of Formula I, and the pharmaceutical compositions thereof, include cancer. Non-limiting examples of the types of cancer that can be treated include ovarian cancer, cervical cancer, breast cancer, colorectal cancer, or glioblastomas.

The foregoing only summarizes certain aspects of the invention and is not intended to be limiting in nature. These aspects and other aspects and embodiments are described more fully below.

DETAILED DESCRIPTION OF THE INVENTION

The invention relates to a compound according to Formula I:

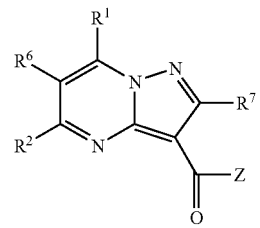

or a pharmaceutically acceptable salt thereof, wherein:

$R^1$ is selected from —OH, —O—($C_1$-$C_6$)alkyl, and —NH($C_1$-$C_6$)alkyl-(5-10 membered)aryl;

$R^2$ is selected from -(5-10 membered)heteroaryl, -(4-10 membered)heterocycloalkyl, —($C_5$-$C_{10}$)aryl, and —($C_1$-$C_6$)alkyl, wherein the -(5-10 membered)heteroaryl, —($C_5$-$C_{10}$)aryl and -(4-10 membered)heterocycloalkyl are each optionally substituted with 1-3 groups independently selected from halo, —OH, —$NH_2$, —NH($C_1$-$C_6$)alkyl, —N[($C_1$-$C_6$)alkyl]$_2$, —$NO_2$, —CN, —O—($C_1$-$C_6$)alkyl, halo, —S—($C_1$-$C_6$)alkyl, —$CF_3$, —($C_1$-$C_6$)alkyl, —($C_3$-$C_{10}$)cycloalkyl, and —($C_1$-$C_6$)alkyl-($C_3$-$C_{10}$)cycloalkyl;

$R^3$ is selected from H, —($C_1$-$C_6$)alkyl-($C_5$-$C_{10}$)aryl, —C($R^5$)—($C_1$-$C_6$)alkyl-($C_5$-$C_{10}$)aryl, —C($R^5$)—($C_1$-$C_6$)alkyl, —C($R^5$)—($C_5$-$C_{10}$)aryl, —C($R^5$)—($C_3$-$C_{10}$)cycloalkyl, —C($R^5$)—($C_1$-$C_6$)alkyl-($C_3$-$C_{10}$)cycloalkyl, —C($R^5$)—($C_1$-$C_6$)alkyl-(4-10 membered)heterocycloalkyl, —C($R^5$)-(5-10 membered)heterocycloalkyl, —($C_1$-$C_6$)alkyl-($C_3$-$C_{10}$)cycloalkyl, —($C_3$-$C_{10}$)cycloalkyl, —($C_1$-$C_6$)alkyl-N[$C_1$-$C_6$)alkyl]$_2$, —($C_1$-$C_6$)alkyl, —($C_1$-$C_6$)alkyl-(4-10 membered)heterocycloalkyl, and -(4-10 membered)heterocycloalkyl, wherein each —($C_1$-$C_6$)alkyl-($C_5$-$C_{10}$)aryl, —C($R^5$)—($C_1$-$C_6$)alkyl-($C_5$-$C_{10}$)aryl, —C($R^5$)—($C_1$-$C_6$)alkyl, —C($R^5$)—($C_5$-$C_{10}$)aryl, —C($R^5$)—($C_3$-$C_{10}$)cycloalkyl, —C($R^5$)—($C_1$-$C_6$)alkyl-($C_3$-$C_{10}$)cycloalkyl, —C($R^5$)—($C_1$-$C_6$)alkyl-(4-10 membered)heterocycloalkyl, —C($R^5$)-(4-10 membered)heterocycloalkyl, —($C_3$-$C_{10}$)cycloalkyl, —($C_1$-$C_6$)alkyl-($C_3$-$C_{10}$)cycloalkyl, —($C_1$-$C_6$)alkyl-N[$C_1$-$C_6$)alkyl]$_2$, —($C_1$-$C_6$)alkyl, —($C_1$-$C_6$)alkyl-(4-10 membered)heterocycloalkyl, and -(4-10 membered)heterocycloalkyl are optionally substituted with 1-3 groups independently selected from —($C_1$-$C_6$)alkyl, —O—($C_1$-$C_6$)alkyl, halo, —($C_5$-$C_{10}$)aryl, —$NO_2$, —C(O)O—($C_1$-$C_6$)alkyl, —C(O)—($C_1$-$C_6$)alkyl, —O—($C_5$-$C_{10}$)aryl, —S—$CH_3$, —$SO_2$—$CH_3$, —C(O)$CH_3$, —$CF_3$ and -(4-10 membered)heterocycloalkyl optionally substituted with —($C_1$-$C_6$)alkyl or —N[($C_1$-$C_6$)alkyl]$_2$;

$R^4$ is H or —$(C_1$-$C_6)$alkyl, or $R^3$ and $R^4$, together with the nitrogen atom to which they are attached, form a -(4-10 membered)heterocycloalkyl optionally substituted with 1-3 groups independently selected from halo, —$(C_1$-$C_6)$alkyl, —O—$(C_1$-$C_6)$alkyl, —$(C_5$-$C_{10})$aryl, —$SO_2$—$(C_1$-$C_6)$alkyl, -(4-10 membered)heterocycloalkyl, -(3-10 membered)cycloalkyl, -(5-10 membered)heteroaryl and —C(O)—$(C_1$-$C_6)$alkyl, wherein each —$(C_5$-$C_{10})$aryl, —$SO_2$—$(C_1$-$C_6)$alkyl, -(4-10 membered)heterocycloalkyl, -(3-10 membered)cycloalkyl, and (5-10 membered)heteroaryl is optionally substituted with 1, 2 or 3 groups selected from —$(C_1$-$C_6)$alkyl, —O—$(C_1$-$C_6)$alkyl, halo, —$NO_2$, —$(C_5$-$C_{10})$aryl, —$(C_3$-$C_{10})$cycloalkyl, —$(C_1$-$C_6)$alkyl-$(C_3$-$C_{10})$cycloalkyl, -(4-10 membered)heterocycloalkyl, —$(C_1$-$C_6)$alkyl-(4-10 membered)heterocycloalkyl, -(5-10 membered)heteroaryl, —S—$CH_3$, and —$CF_3$;

$R^5$ is —C(O)O($C_1$-$C_6$)alkyl;

$R^6$ is H or —$(C_1$-$C_3)$alkyl;

$R^7$ is H, —NH($C_1$-$C_6$alkyl) or —N[$C_1$-$C_6$alkyl]$_2$;

$R^8$ is selected from —$(C_5$-$C_{10}$aryl, —$(C_3$-$C_{10})$cycloalkyl, —$(C_1$-$C_6)$alkyl-$(C_3$-$C_{10})$cycloalkyl, -(4-10 membered)heterocycloalkyl, —$(C_1$-$C_6)$alkyl-(4-10 membered)heterocycloalkyl, -(5-10 membered)hetero aryl, —$(C_1$-$C_6)$ alkyl-(5-10 membered)hetero aryl and —$(C_1$-$C_6)$alkyl-$(C_5$-$C_{10})$ aryl; and Z is —$OR^8$ or —$NR^3R^4$, with the proviso that when $R^1$ is —OH, $R^2$ is $CH_3$, $R^6$ is H, $R^7$ is H, and Z is —C(O)NHR$^3$, then $R^3$ is not

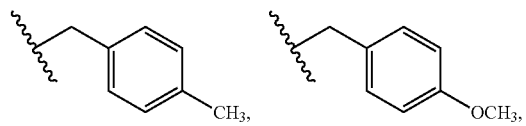

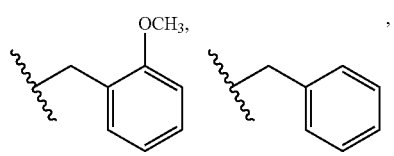

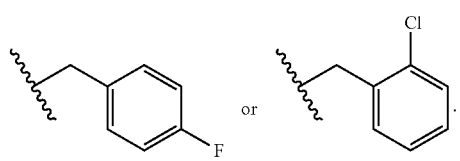

In another embodiment of the compound of Formula I, $R^8$ is —$(C_5$-$C_{10})$aryl or —$(C_1$-$C_6)$alkyl-$(C_5$-$C_{10})$aryl.

In another embodiment of the compound of Formula I, $R^3$ is —$(C_1$-$C_6)$alkyl-$(C_5$-$C_{10})$aryl substituted with 1-3 groups independently selected from —$(C_2$-$C_6)$alkyl, —O—$(C_2$-$C_6)$alkyl, Br, —$(C_5$-$C_{10})$aryl, —$NO_2$, —C(O)O—$(C_1$-$C_6)$alkyl, —C(O)—$(C_1$-$C_6)$alkyl, —O—$(C_5$-$C_{10})$aryl, —S—$CH_3$, —$SO_2$—$CH_3$, —C(O)$CH_3$, —$CF_3$ and -(4-10 membered)heterocycloalkyl optionally substituted with —$(C_1$-$C_6)$alkyl, —$SO_2CH_3$ or —N[$(C_1$-$C_6)$alkyl]$_2$.

In another embodiment of the compound of Formula I, $R^1$ is OH.

In another embodiment of the compound of Formula I, $R^2$ is $CH_3$.

In another embodiment of the compound of Formula I, $R^2$ is phenyl optionally substituted with 1, 2 or 3 halogens.

In another embodiment of the compound of Formula I, $R^2$ is furanyl or pyridinyl.

In another embodiment of the compound of Formula I, $R^3$ is —$(C_1$-$C_6)$alkyl-phenyl optionally substituted with morpholinyl or piperizinyl optionally substituted with —$(C_1$-$C_6)$alkyl.

In another embodiment of the compound of Formula I, $R^3$ is piperidinyl optionally substituted with —$SO_2CH_3$.

In another embodiment of the compound of Formula I, $R^3$ is —$(C_3$-$C_6)$cycloalkyl optionally substituted with phenyl.

In another embodiment of the compound of Formula I, $R^3$ is cyclopropane or cyclopentane optionally substituted with phenyl.

In another embodiment of the compound of formula I, $R^3$ is —C($R^5$)—$(C_1$-$C_6)$alkyl —$(C_5$-$C_{10})$aryl, —C($R^5$)—$(C_1$-$C_6)$alkyl, or —C($R^5$)—$(C_5$-$C_{10})$aryl.

In another embodiment of the compound of formula I, $R^3$ is —C($R^5$)—$(C_1$-$C_6)$alkyl —$(C_5$-$C_{10})$aryl.

In another embodiment, the compound of Formula I is of Formula II:

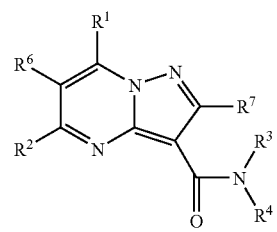

II or a pharmaceutically acceptable salt thereof, wherein:

$R^1$ is —OH or —O($C_1$-$C_3)$alkyl;

$R^2$ is independently selected from —$(C_1$-$C_3)$alkyl, phenyl optionally substituted with 1-3 groups independently selected from halo, —$CF_3$, —O($C_1$-$C_3)$alkyl, —$(C_1$-$C_3)$alkyl, furanyl and pyridinyl optionally substituted with methyl;

$R^3$ is selected from H, —$(C_1$-$C_3)$alkyl-phenyl optionally substituted with 1-3 substituents independently selected from —$OCH_3$, —$NO_2$, halo, phenyl, —S—$CH_3$, —O-phenyl, —$(C_1$-$C_3)$alkyl, morpholinyl, —$CF_3$, —$(C_1$-$C_6)$alkyl, piperizinyl optionally substituted with —$(C_1$-$C_3)$alkyl and —$(C_1$-$C_3)$alkyl-piperidinyl optionally substituted with —$(C_1$-$C_3)$alkyl; cyclohexyl; —$(C_1$-$C_3)$alkyl-N($CH_3)_2$; —$(C_1$-$C_6)$alkyl; cyclopentyl; piperizinyl optionally substituted with phenyl; —$(C_1$-$C_3)$alkyl-morpholinyl; piperidinyl optionally substituted with —CH$_3$, —SO$_2$CH$_3$, —CH$_2$—NH$_2$, piperidinyl or pyrrolidinyl; 3,4-dihydroisoquinolinyl; cyclopropyl optionally substituted with phenyl; pyrrolidinyl optionally substituted with methyl; —CH$_2$-pyrrolidinyl optionally substituted with —CH$_3$; —(C$_1$-C$_3$)alkyl-piperidinyl optionally substituted with —(C$_1$-C$_3$)alkyl, —C(O)—(C$_1$-C$_3$)alkyl, or —C(O))C(CH$_3$)$_3$; and -cyclopentyl-phenyl;

R$^4$ is H or —(C$_1$-C$_3$)alkyl, or R$^3$ and R$^4$, together with the nitrogen atom to which they are attached, form dihydroisoquinolinyl, morpholinyl, piperidinyl, pyrrolidinyl or piperizinyl, wherein the piperidinyl, pyrrolidinyl and piperizinyl are each optionally substituted with —C(O)—CH$_3$, —SO$_2$—CH$_3$, piperidinyl, pyrrolidinyl, phenyl, —(C$_1$-C$_3$)alkyl, or —CH$_2$—NH$_2$;

R$^6$ is H; and

R$^7$ is H.

In another embodiment, R$^3$ is selected from H, —(C$_1$-C$_3$)alkyl-phenyl substituted with 1-3 substituents independently selected from —NO$_2$, phenyl, —S—CH$_3$, morpholinyl, —O-phenyl, —CF$_3$, piperizinyl optionally substituted with —(C$_1$-C$_3$)alkyl, and —(C$_1$-C$_3$)alkyl-piperidinyl optionally substituted with —(C$_1$-C$_3$)alkyl;

In another embodiment of the compound of Formula II, R$^1$ is OH.

In another embodiment of the compound of Formula II, R$^2$ is CH$_3$.

In another embodiment of the compound of Formula II, R$^2$ is phenyl optionally substituted with 1, 2 or 3 halogens.

In another embodiment of the compound of Formula II, R$^2$ is furanyl or pyridinyl.

In another embodiment of the compound of Formula II, R$^3$ is —(C$_1$-C$_3$)alkyl-phenyl optionally substituted with morpholinyl or piperizinyl optionally substituted with —(C$_1$-C$_6$)alkyl.

In another embodiment of the compound of Formula II, R$^3$ is piperidinyl optionally substituted with —SO$_2$CH$_3$.

In another embodiment of the compound of Formula II, R$^3$ is —(C$_3$-C$_6$)cycloalkyl optionally substituted with phenyl.

In another embodiment of the compound of Formula II, R$^3$ is cyclopropane or cyclopentane optionally substituted with phenyl.

In another embodiment, the compound of Formula I is of Formula III:

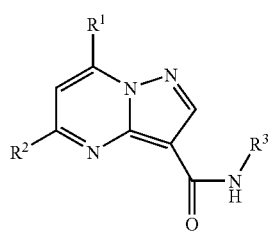

III or a pharmaceutically acceptable salt thereof, wherein:

R$^1$ is —OH or —OCH$_3$;

R$^2$ is independently selected from —CH$_3$, phenyl optionally substituted with 1-3 groups independently selected from halo, —CF$_3$, and —OCH$_3$, —(C$_1$-C$_3$)alkyl, furanyl and pyridinyl optionally substituted with methyl;

R$^3$ is selected from —CH$_2$-phenyl optionally substituted with 1-3 substituents independently selected from —OCH$_3$, halo, phenyl, —S—CH$_3$, —O-phenyl, —CH$_3$, —CF$_3$, —(C$_1$-C$_6$)alkyl, piperizinyl optionally substituted with —(C$_1$-C$_3$)alkyl, morpholinyl, and —CH$_2$-piperidine optionally substituted with —(C$_1$-C$_3$)alkyl; —(C$_1$-C$_3$)alkylmorpholinyl; —(C$_1$-C$_3$)alkyl-piperidinyl optionally substituted with —(C$_1$-C$_3$)alkyl; -piperidinyl optionally substituted with —(C$_1$-C$_3$)alkyl; —(C$_1$-C$_3$)alkyl-piperizinyl optionally substituted with —(C$_1$-C$_3$)alkyl; piperidinyl optionally substituted with —SO$_2$CH$_3$, -piperizinyl optionally substituted with —(C$_1$-C$_3$)alkyl; and R$^5$ is —C(O)(C$_1$-C$_3$)alkyl or —C(O)O(C$_1$-C$_3$)alkyl.

In another embodiment, R$^3$ is —CH$_2$-phenyl optionally substituted with 1-3 substituents independently selected from phenyl, —S—CH$_3$, —O-phenyl, —CF$_3$, piperizinyl optionally substituted with —(C$_1$-C$_3$)alkyl, morpholinyl, and —CH$_2$-piperidine optionally substituted with —(C$_1$-C$_3$)alkyl.

In another embodiment of the compound of Formula III, R$^1$ is OH.

In another embodiment of the compound of Formula III, R$^2$ is CH$_3$.

In another embodiment of the compound of Formula III, R$^2$ is phenyl optionally substituted with 1, 2 or 3 halogens.

In another embodiment of the compound of Formula III, R$^2$ is furanyl or pyridinyl.

In another embodiment of the compound of Formula III, R$^3$ is —CH$_2$-phenyl optionally substituted with morpholinyl or piperizinyl optionally substituted with —CH$_3$.

In another embodiment of the compound of Formula III, R$^3$ is piperidinyl optionally substituted with —SO$_2$CH$_3$.

In another embodiment of the compound of Formula III, R$^3$ is —(C$_3$-C$_6$)cycloalkyl optionally substituted with phenyl.

In another embodiment of the compound of Formula III, R$^3$ is cyclopropane or cyclopentane optionally substituted with phenyl.

Another aspect of the invention relates to a pharmaceutical composition comprising a compound according to Formulae I, II or III and a pharmaceutically acceptable carrier, excipient, or diluent.

Another aspect of the invention relates to a method of inhibiting CK2 in a cell, comprising contacting a cell in which inhibition of CK2 is desired with a compound according to Formulae I, II or III, or a pharmaceutical composition comprising a compound according to Formulae I, II or III and a pharmaceutically acceptable carrier, excipient, or diluent.

Another aspect of the invention relates to a method of treating a disease or condition that involves CK2 comprising administering to a patient a compound according to Formulae I, II or III, or a pharmaceutical composition comprising a compound according to Formulae I, II or III and a pharmaceutically acceptable carrier, excipient, or diluent. The disease or condition is cancer such as ovarian cancer, cervical cancer, breast cancer, colorectal cancer, or glioblastomas.

Table 1 illustrates some examples of the compounds of the invention. The examples in Table 1 merely illustrate some embodiments of the invention, and do not limit the scope of the invention in any way.

TABLE 1

| Cpd. No. | Structure | IUPAC Name | MS |
|---|---|---|---|
| 1 | 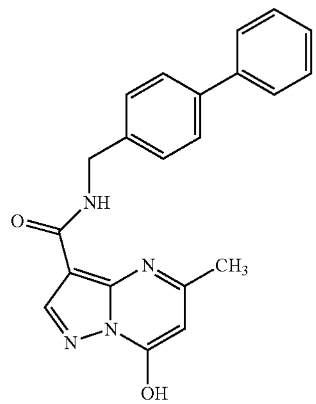 [SMILES: Cc1cc(O)n2ncc(C(=O)NCc3ccc(-c4ccccc4)cc3)c2n1] | N-(biphenyl-4-ylmethyl)-7-hydroxy-5-methylpyrazolo[1,5-a]pyrimidine-3-carboxamide | 359 |
| 2 | 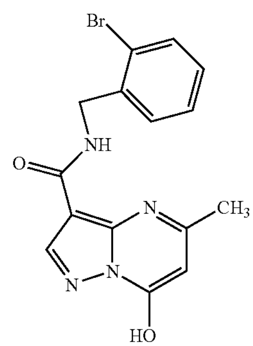 [SMILES: Cc1cc(O)n2ncc(C(=O)NCc3ccccc3Br)c2n1] | N-[(2-bromophenyl)methyl]-7-hydroxy-5-methylpyrazolo[1,5-a]pyrimidine-3-carboxamide | 362 |
| 3 | 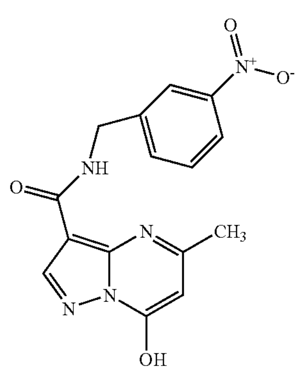 [SMILES: Cc1cc(O)n2ncc(C(=O)NCc3cccc([N+](=O)[O-])c3)c2n1] | 7-hydroxy-5-methyl-N-[(3-nitrophenyl)methyl]pyrazolo[1,5-a]pyrimidine-3-carboxamide | 328 |
| 4 | 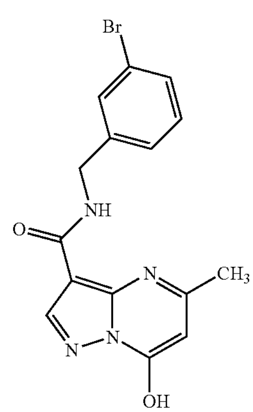 [SMILES: Cc1cc(O)n2ncc(C(=O)NCc3cccc(Br)c3)c2n1] | N-[(3-bromophenyl)methyl]-7-hydroxy-5-methylpyrazolo[1,5-a]pyrimidine-3-carboxamide | 362 |

TABLE 1-continued

| Cpd. No. | Structure | IUPAC Name | MS |
|---|---|---|---|
| 5 | 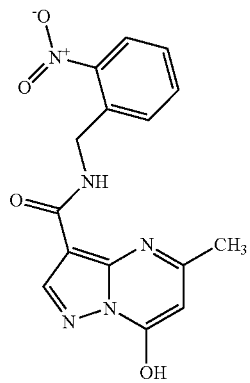 | 7-hydroxy-5-methyl-N-[(2-nitrophenyl)methyl]pyrazolo[1,5-a]pyrimidine-3-carboxamide | 329 |
| 6 | 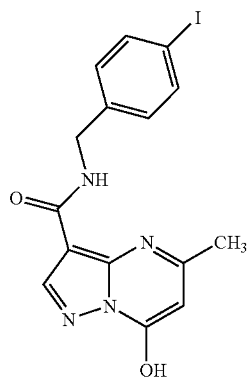 [SMILES: Cc1cc(O)n2ncc(C(=O)NCc3ccc(I)cc3)c2n1] | 7-hydroxy-N-[(4-iodophenyl)methyl]-5-methylpyrazolo[1,5-a]pyrimidine-3-carboxamide | 409 |
| 7 | 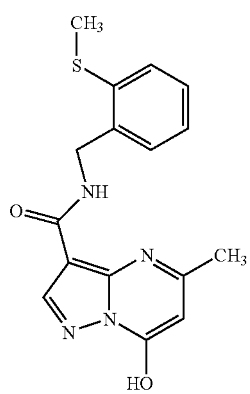 [SMILES: CSc1ccccc1CNC(=O)c1cnn2c(O)cc(C)nc12] | 7-hydroxy-5-methyl-N-{[2-(methylthio)phenyl]methyl}pyrazolo[1,5-a]pyrimidine-3-carboxamide | 329 |
| 8 | 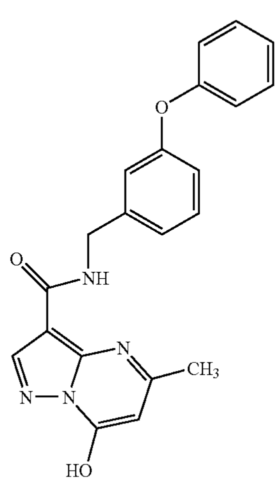 [SMILES: Cc1cc(O)n2ncc(C(=O)NCc3cccc(Oc4ccccc4)c3)c2n1] | 7-hydroxy-5-methyl-N-{[3-(phenyloxy)phenyl]methyl}pyrazolo[1,5-a]pyrimidine-3-carboxamide | 375 |

TABLE 1-continued

| Cpd. No. | Structure | IUPAC Name | MS |
| --- | --- | --- | --- |
| 9 | 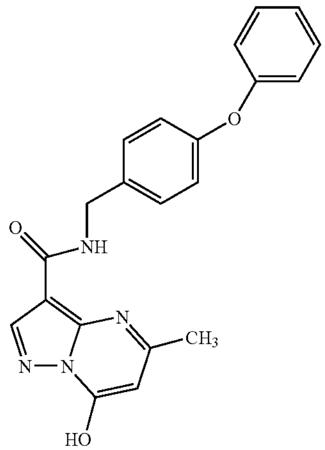 [SMILES: Cc1cc(O)n2ncc(C(=O)NCc3ccc(Oc4ccccc4)cc3)c2n1] | 7-hydroxy-5-methyl-N-{[4-(phenyloxy)phenyl]methyl}pyrazolo[1,5-a]pyrimidine-3-carboxamide | 375 |
| 10 | 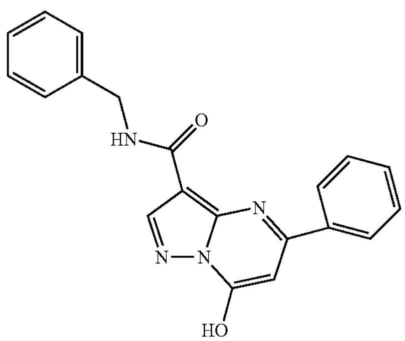 [SMILES: O=C(NCc1ccccc1)c1cnn2c(O)cc(-c3ccccc3)nc12] | 7-hydroxy-5-phenyl-N-(phenylmethyl)pyrazolo[1,5-a]pyrimidine-3-carboxamide | 345 |
| 11 | 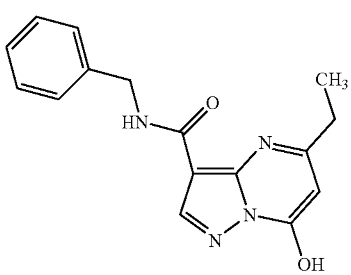 [SMILES: CCc1cc(O)n2ncc(C(=O)NCc3ccccc3)c2n1] | 5-ethyl-7-hydroxy-N-(phenylmethyl)pyrazolo[1,5-a]pyrimidine-3-carboxamide | 297 |
| 12 | 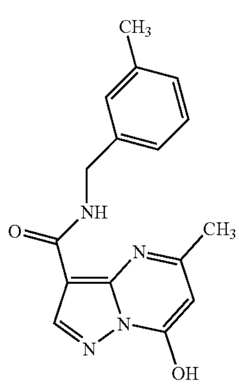 [SMILES: Cc1cccc(CNC(=O)c2cnn3c(O)cc(C)nc23)c1] | 7-hydroxy-5-methyl-N-[(3-methylphenyl)methyl]pyrazolo[1,5-a]pyrimidine-3-carboxamide | 297 |

TABLE 1-continued

| Cpd. No. | Structure | IUPAC Name | MS |
|---|---|---|---|
| 13 | 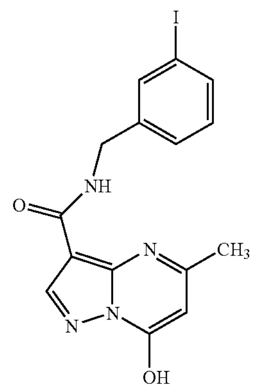 [SMILES: Cc1cc(O)n2ncc(C(=O)NCc3cccc(I)c3)c2n1] | 7-hydroxy-N-[(3-iodophenyl)methyl]-5-methylpyrazolo[1,5-a]pyrimidine-3-carboxamide | 409 |
| 14 | 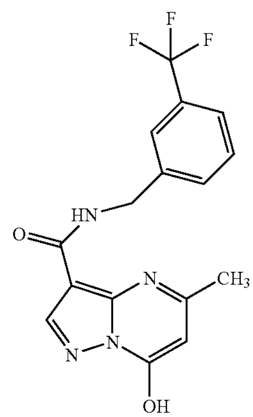 [SMILES: Cc1cc(O)n2ncc(C(=O)NCc3cccc(C(F)(F)F)c3)c2n1] | 7-hydroxy-5-methyl-N-{(3-(trifluoromethyl)phenyl]methyl}pyrazolo[1,5-a]pyrimidine-3-carboxamide | 351 |
| 15 | 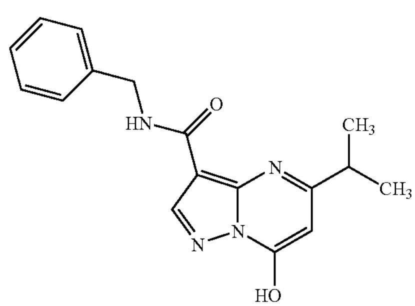 [SMILES: CC(C)c1cc(O)n2ncc(C(=O)NCc3ccccc3)c2n1] | 7-hydroxy-5-(1-methylethyl)-N-(phenylmethyl)pyrazolo[1,5-a]pyrimidine-3-carboxamide | 311 |
| 16 | 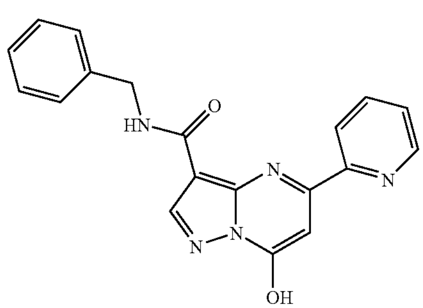 [SMILES: O=C(NCc1ccccc1)c1cnn2c(O)cc(-c3ccccn3)nc12] | 7-hydroxy-N-(phenylmethyl)-5-pyridin-2-ylpyrazolo[1,5-a]pyrimidine-3-carboxamide | 346 |

TABLE 1-continued

| Cpd. No. | Structure | IUPAC Name | MS |
|---|---|---|---|
| 17 | 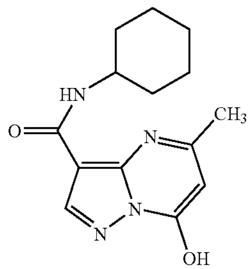 [SMILES: Cc1cc(O)n2ncc(C(=O)NC3CCCCC3)c2n1] | N-cyclohexyl-7-hydroxy-5-methylpyrazolo[1,5-a]pyrimidine-3-carboxamide | 275 |
| 18 | 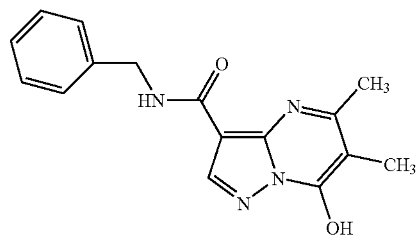 [SMILES: Cc1nc2c(C(=O)NCc3ccccc3)cnn2c(O)c1C] | 7-hydroxy-5,6-dimethyl-N-(phenylmethyl)pyrazolo[1,5-a]pyrimidine-3-carboxamide | 297 |
| 19 | 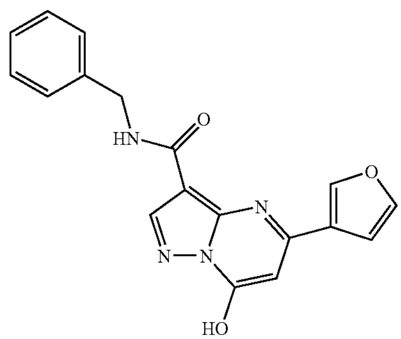 [SMILES: O=C(NCc1ccccc1)c1cnn2c(O)cc(-c3ccoc3)nc12] | 5-furan-3-yl-7-hydroxy-N-(phenylmethyl)pyrazolo[1,5-a]pyrimidine-3-carboxamide | 335 |
| 20 | 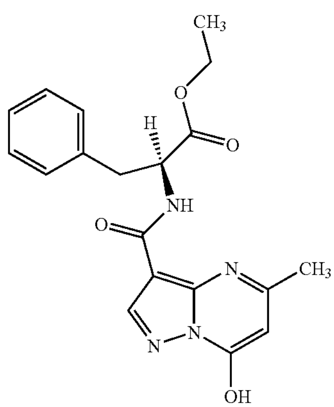 | ethyl N-[(7-hydroxy-5-methylpyrazolo[1,5-a]pyrimidin-3-yl)carbonyl]-L-phenylalaninate | 369 |
| 21 | 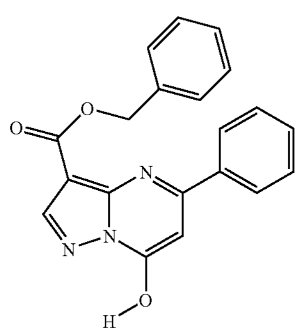 [SMILES: O=C(OCc1ccccc1)c1cnn2c(O)cc(-c3ccccc3)nc12] | phenylmethyl 7-hydroxy-5-phenylpyrazolo[1,5-a]pyrimidine-3-carboxylate | 346 |

TABLE 1-continued

| Cpd. No. | Structure | IUPAC Name | MS |
|---|---|---|---|
| 22 | 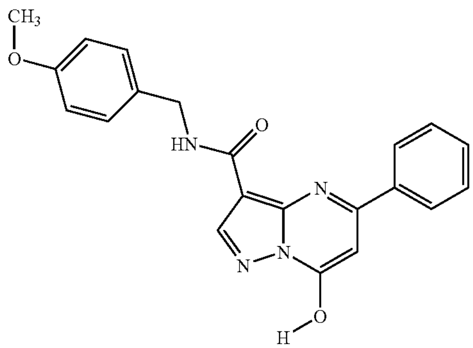 [SMILES: COc1ccc(CNC(=O)c2cnn3c(O)cc(-c4ccccc4)nc23)cc1] | 7-hydroxy-N-{[4-(methyloxy)phenyl]methyl)-5-phenylpyrazolo[1,5-a]pyrimidine-3-carboxamide | 375 |
| 23 | 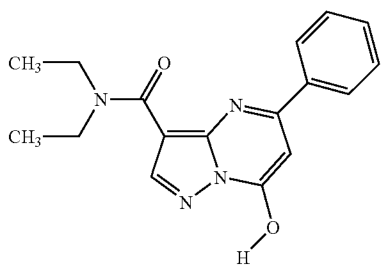 [SMILES: CCN(CC)C(=O)c1cnn2c(O)cc(-c3ccccc3)nc12] | N,N-diethyl-7-hydroxy-5-phenylpyrazolo[1,5-a]pyrimidine-3-carboxamide | 311 |
| 24 | 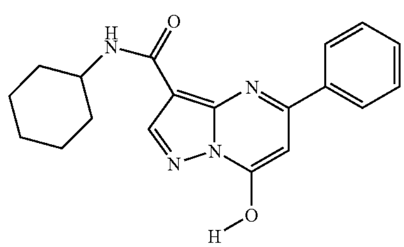 [SMILES: O=C(NC1CCCCC1)c1cnn2c(O)cc(-c3ccccc3)nc12] | N-cyclohexyl-7-hydroxy-5-phenylpyrazolo[1,5-a]pyrimidine-3-carboxamide | 337 |
| 25 | 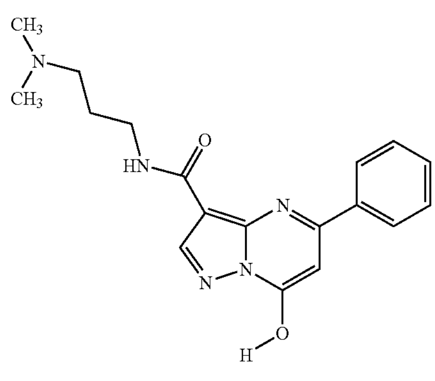 [SMILES: CN(C)CCCNC(=O)c1cnn2c(O)cc(-c3ccccc3)nc12] | N-[3-(dimethylamino)propyl]-7-hydroxy-5-phenylpyrazolo[1,5-a]pyrimidine-3-carboxamide | 340 |
| 26 | 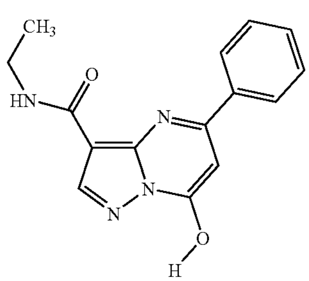 [SMILES: CCNC(=O)c1cnn2c(O)cc(-c3ccccc3)nc12] | N-ethyl-7-hydroxy-5-phenylpyrazolo[1,5-a]pyrimidine-3-carboxamide | 283 |

TABLE 1-continued

| Cpd. No. | Structure | IUPAC Name | MS |
|---|---|---|---|
| 27 | 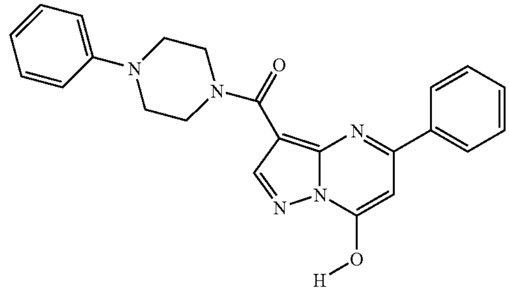 [SMILES: O=C(c1cnn2c(O)cc(-c3ccccc3)nc12)N1CCN(c2ccccc2)CC1] | 5-phenyl-3-[(4-phenylpiperazin-1-yl)carbonyl]pyrazolo[1,5-a]pyrimidin-7-ol | 400 |
| 28 | 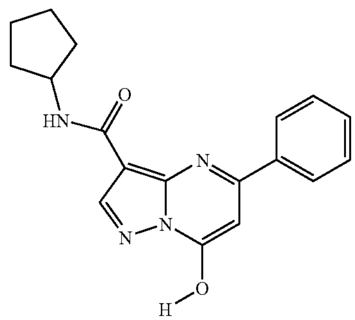 [SMILES: O=C(NC1CCCC1)c1cnn2c(O)cc(-c3ccccc3)nc12] | N-cyclopentyl-7-hydroxy-5-phenylpyrazolo[1,5-a]pyrimidine-3-carboxamide | 323 |
| 29 | 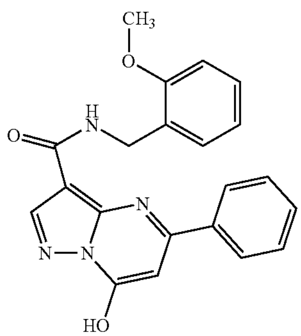 [SMILES: COc1ccccc1CNC(=O)c1cnn2c(O)cc(-c3ccccc3)nc12] | 7-hydroxy-N-{[2-(methyloxy)phenyl]methyl}-5-phenylpyrazolo[1,5-a]pyrimidine-3-carboxamide | 375 |
| 30 | 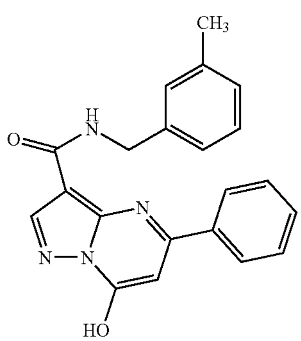 [SMILES: Cc1cccc(CNC(=O)c2cnn3c(O)cc(-c4ccccc4)nc23)c1] | 7-hydroxy-N-[(3-methylphenyl)methyl]-5-phenylpyrazolo[1,5-a]pyrimidine-3-carboxamide | 359 |
| 31 | 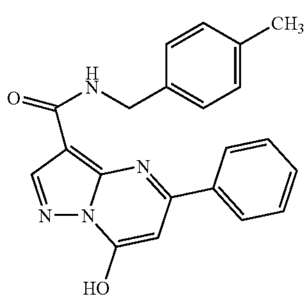 [SMILES: Cc1ccc(CNC(=O)c2cnn3c(O)cc(-c4ccccc4)nc23)cc1] | 7-hydroxy-N-[(4-methylphenyl)methyl]-5-phenylpyrazolo[1,5-a]pyrimidine-3-carboxamide | 359 |

TABLE 1-continued

| Cpd. No. | Structure | IUPAC Name | MS |
|---|---|---|---|
| 32 | 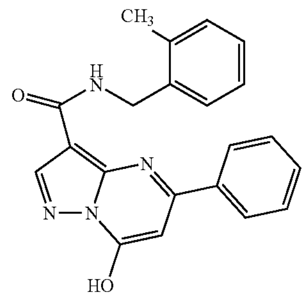 [SMILES: Cc1ccccc1CNC(=O)c1cnn2c(O)cc(-c3ccccc3)nc12] | 7-hydroxy-N-[(2-methylphenyl)methyl]-5-phenylpyrazolo[1,5-a]pyrimidine-3-carboxamide | 359 |
| 33 | 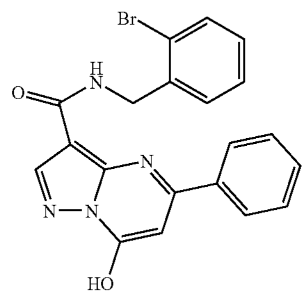 [SMILES: O=C(NCc1ccccc1Br)c1cnn2c(O)cc(-c3ccccc3)nc12] | N-[(2-bromophenyl)methyl]-7-hydroxy-5-phenylpyrazolo[1,5-a]pyrimidine-3-carboxamide | 424 |
| 34 | 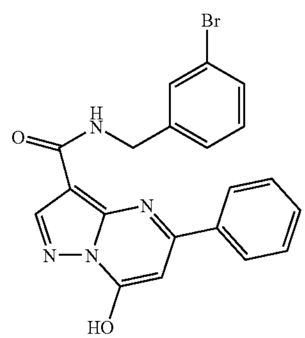 [SMILES: O=C(NCc1cccc(Br)c1)c1cnn2c(O)cc(-c3ccccc3)nc12] | N-[(3-bromophenyl)methyl]-7-hydroxy-5-phenylpyrazolo[1,5-a]pyrimidine-3-carboxamide | 424 |
| 35 | 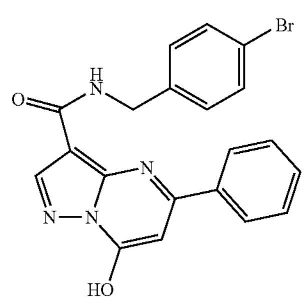 [SMILES: O=C(NCc1ccc(Br)cc1)c1cnn2c(O)cc(-c3ccccc3)nc12] | N-[(4-bromophenyl)methyl]-7-hydroxy-5-phenylpyrazolo[1,5-a]pyrimidine-3-carboxamide | 424 |
| 36 | 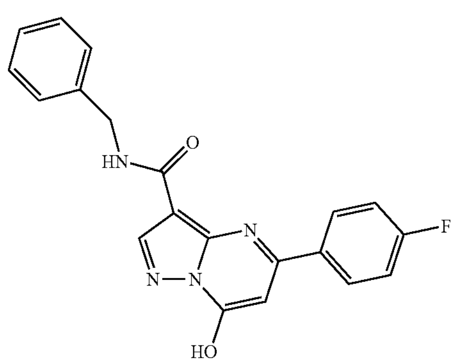 [SMILES: O=C(NCc1ccccc1)c1cnn2c(O)cc(-c3ccc(F)cc3)nc12] | 5-(4-fluorophenyl)-7-hydroxy-N-(phenylmethyl)pyrazolo[1,5-a]pyrimidine-3-carboxamide | 363 |

TABLE 1-continued

| Cpd. No. | Structure | IUPAC Name | MS |
|---|---|---|---|
| 37 | 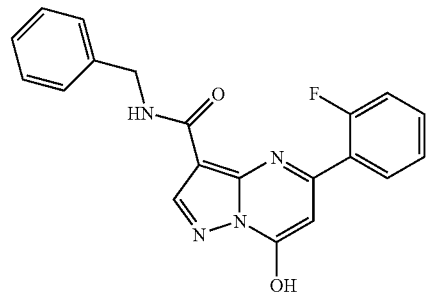 [SMILES: O=C(NCc1ccccc1)c1cnn2c(O)cc(-c3ccccc3F)nc12] | 5-(2-fluorophenyl)-7-hydroxy-N-(phenylmethyl)pyrazolo[1,5-a]pyrimidine-3-carboxamide | 363 |
| 38 | 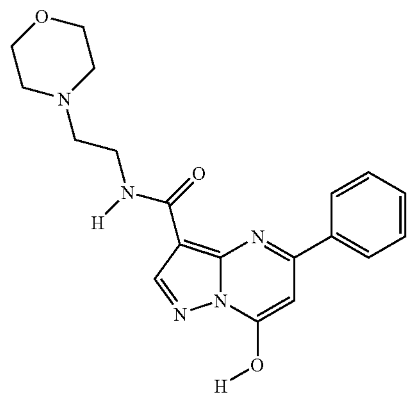 [SMILES: O=C(NCCN1CCOCC1)c1cnn2c(O)cc(-c3ccccc3)nc12] | 7-hydroxy-N-(2-morpholin-4-ylethyl)-5-phenylpyrazolo[1,5-a]pyrimidine-3-carboxamide | 368 |
| 39 | 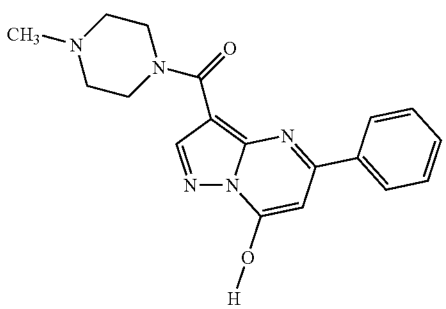 [SMILES: CN1CCN(C(=O)c2cnn3c(O)cc(-c4ccccc4)nc23)CC1] | 3-[(4-methylpiperazin-1-yl)carbonyl]-5-phenylpyrazolo[1,5-a]pyrimidin-7-ol | 338 |
| 40 | 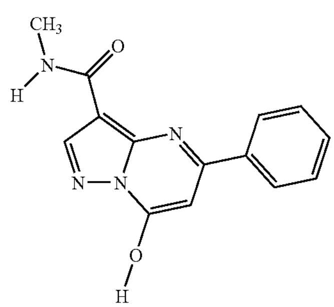 [SMILES: CNC(=O)c1cnn2c(O)cc(-c3ccccc3)nc12] | 7-hydroxy-N-methyl-5-phenylpyrazolo[1,5-a]pyrimidine-3-carboxamide | 269 |
| 41 | 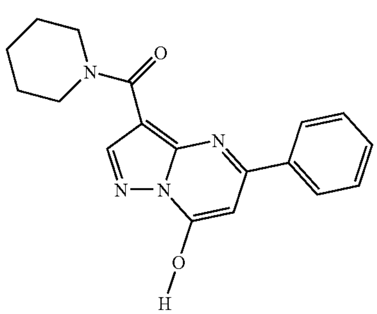 [SMILES: O=C(c1cnn2c(O)cc(-c3ccccc3)nc12)N1CCCCC1] | 5-phenyl-3-(piperidin-1-ylcarbonyl)pyrazolo[1,5-a]pyrimidin-7-ol | 323 |

TABLE 1-continued

| Cpd. No. | Structure | IUPAC Name | MS |
|---|---|---|---|
| 42 | 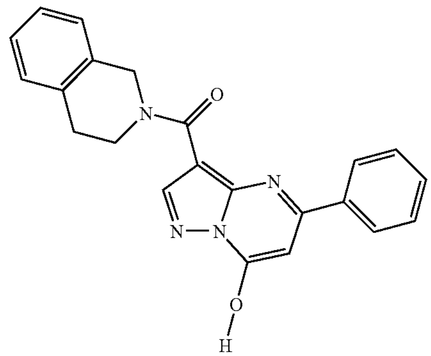 [SMILES: O=C(c1cnn2c(O)cc(-c3ccccc3)nc12)N1CCc2ccccc2C1] | 3-(3,4-dihydroisoquinolin-2(1H)-ylcarbonyl)-5-phenylpyrazolo[1,5-a]pyrimidin-7-ol | 371 |
| 43 | 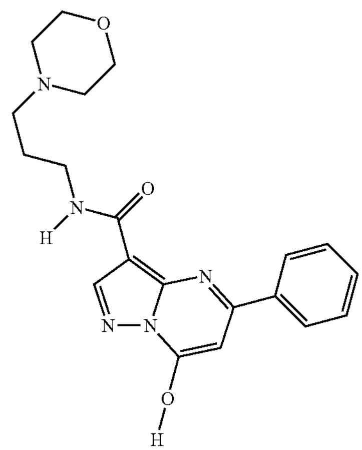 [SMILES: O=C(NCCCN1CCOCC1)c1cnn2c(O)cc(-c3ccccc3)nc12] | 7-hydroxy-N-(3-morpholin-4-ylpropyl)-5-phenylpyrazolo[1,5-a]pyrimidine-3-carboxamide | 382 |
| 44 | 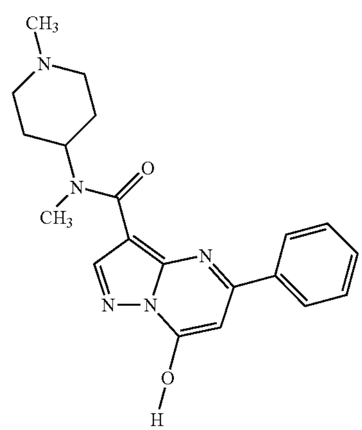 [SMILES: CN1CCC(N(C)C(=O)c2cnn3c(O)cc(-c4ccccc4)nc23)CC1] | 7-hydroxy-N-methyl-N-(1-methylpiperidin-4-yl)-5-phenylpyrazolo[1,5-a]pyrimidine-3-carboxamide | 366 |
| 45 | 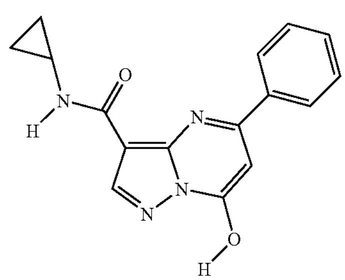 [SMILES: O=C(NC1CC1)c1cnn2c(O)cc(-c3ccccc3)nc12] | N-cyclopropyl-7-hydroxy-5-phenylpyrazolo[1,5-a]pyrimidine-3-carboxamide | 295 |

TABLE 1-continued

| Cpd. No. | Structure | IUPAC Name | MS |
|---|---|---|---|
| 46 | 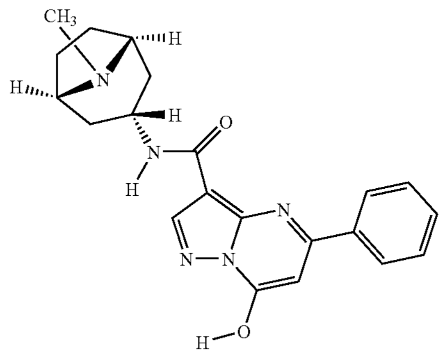 [SMILES: CN1[C@@H]2CC[C@H]1C[C@H](NC(=O)c1cnn3c(O)cc(-c4ccccc4)nc13)C2] | 7-hydroxy-N-[(3-endo)-8-methyl-8-azabicyclo[3.2.1]oct-3-yl]-5-phenylpyrazolo[1,5-a]pyrimidine-3-carboxamide | 377 |
| 47 | 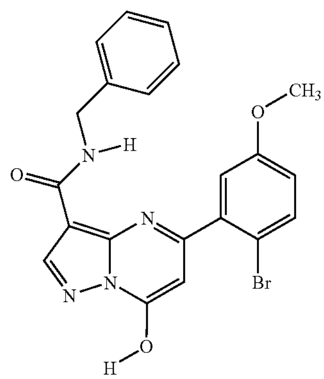 [SMILES: COc1ccc(Br)c(-c2cc(O)n3ncc(C(=O)NCc4ccccc4)c3n2)c1] | 5-[2-bromo-5-(methyloxy)phenyl]-7-hydroxy-N-(phenylmethyl)pyrazolo[1,5-a]pyrimidine-3-carboxamide | 454 |
| 48 | 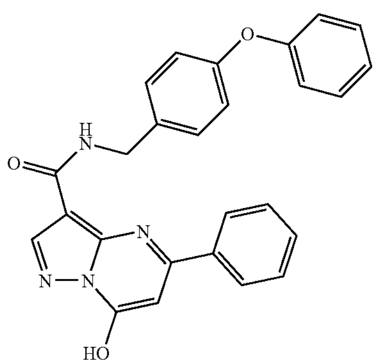 [SMILES: O=C(NCc1ccc(Oc2ccccc2)cc1)c1cnn2c(O)cc(-c3ccccc3)nc12] | 7-hydroxy-5-phenyl-N-{[4-(phenyloxy)phenyl]methyl}pyrazolo[1,5-a]pyrimidine-3-carboxamide | 437 |
| 49 | 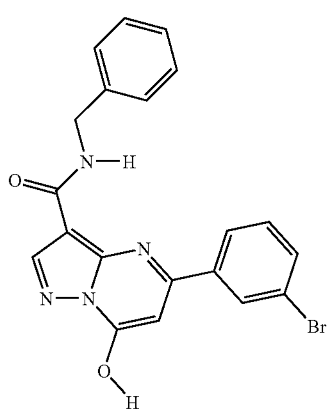 [SMILES: O=C(NCc1ccccc1)c1cnn2c(O)cc(-c3cccc(Br)c3)nc12] | 5-(3-bromophenyl)-7-hydroxy-N-(phenylmethyl)pyrazolo[1,5-a]pyrimidine-3-carboxamide | 424 |

TABLE 1-continued
| Cpd. No. | Structure | IUPAC Name | MS |
|---|---|---|---|
| 50 | 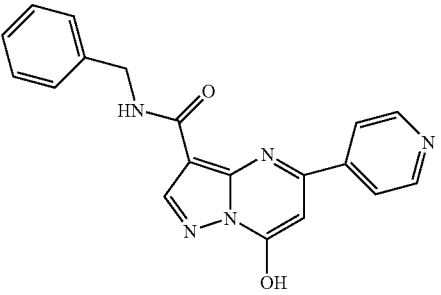 [SMILES: O=C(NCc1ccccc1)c1cnn2c(O)cc(-c3ccncc3)nc12] | 7-hydroxy-N-(phenylmethyl)-5-pyridin-4-ylpyrazolo[1,5-a]pyrimidine-3-carboxamide | 346 |
| 51 | 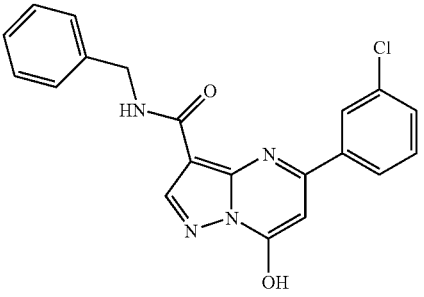 [SMILES: O=C(NCc1ccccc1)c1cnn2c(O)cc(-c3cccc(Cl)c3)nc12] | 5-(3-chlorophenyl)-7-hydroxy-N-(phenylmethyl)pyrazolo[1,5-a]pyrimidine-3-carboxamide | 380 |
| 52 | 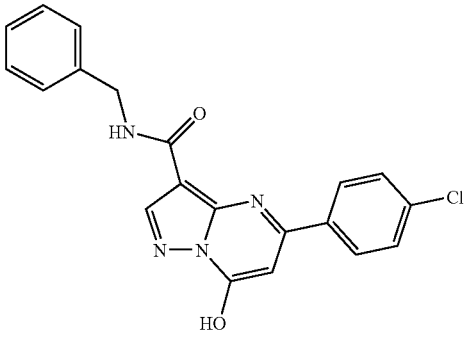 [SMILES: O=C(NCc1ccccc1)c1cnn2c(O)cc(-c3ccc(Cl)cc3)nc12] | 5-(4-chlorophenyl)-7-hydroxy-N-(phenylmethyl)pyrazolo[1,5-a]pyrimidine-3-carboxamide | 380 |
| 53 | 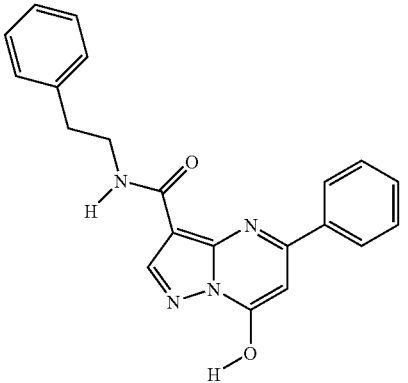 [SMILES: O=C(NCCc1ccccc1)c1cnn2c(O)cc(-c3ccccc3)nc12] | 7-hydroxy-5-phenyl-N-(2-(phenylethyl)pyrazolo[1,5-a]pyrimidine-3-carboxamide | 359 |

TABLE 1-continued

| Cpd. No. | Structure | IUPAC Name | MS |
|---|---|---|---|
| 54 | 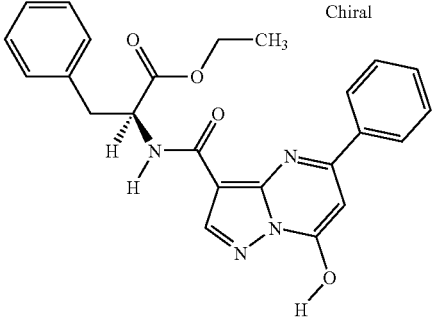 [SMILES: CCOC(=O)[C@H](Cc1ccccc1)NC(=O)c1cnn2c(O)cc(-c3ccccc3)nc12] Chiral | ethyl N-[(7-hydroxy-5-phenylpyrazolo[1,5-a]pyrimidin-3-yl)carbonyl]-L-phenylalaninate | 431 |
| 55 | 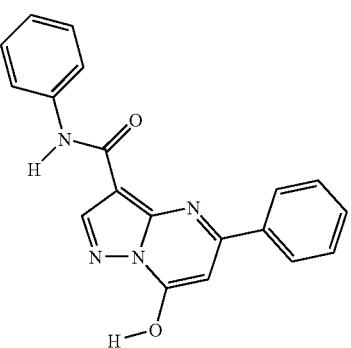 [SMILES: O=C(Nc1ccccc1)c1cnn2c(O)cc(-c3ccccc3)nc12] | 7-hydroxy-N,5-diphenylpyrazolo[1,5-a]pyrimidine-3-carboxamide | 331 |
| 56 | 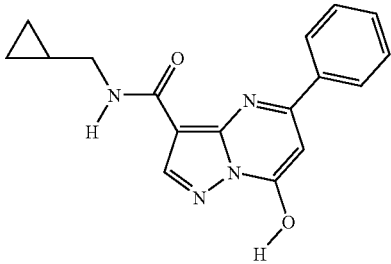 [SMILES: O=C(NCC1CC1)c1cnn2c(O)cc(-c3ccccc3)nc12] | N-(cyclopropylmethyl)-7-hydroxy-5-phenylpyrazolo[1,5-a]pyrimidine-3-carboxamide | 309 |
| 57 | 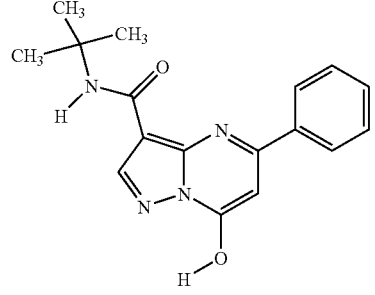 [SMILES: CC(C)(C)NC(=O)c1cnn2c(O)cc(-c3ccccc3)nc12] | N-(1,1-dimethylethyl)-7-hydroxy-5-phenylpyrazolo[1,5-a]pyrimidine-3-carboxamide | 311 |
| 58 | 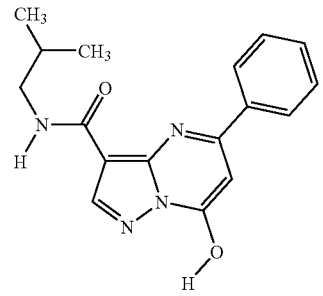 [SMILES: CC(C)CNC(=O)c1cnn2c(O)cc(-c3ccccc3)nc12] | 7-hydroxy-N-(2-methylpropyl)-5-phenylpyrazolo[1,5-a]pyrimidine-3-carboxamide | 311 |

TABLE 1-continued
| Cpd. No. | Structure | IUPAC Name | MS |
|---|---|---|---|
| 59 | 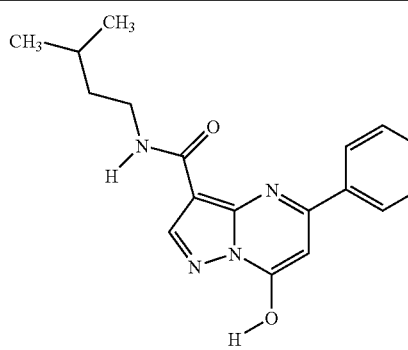 | 7-hydroxy-N-(3-methylbutyl)-5-phenylpyrazolo[1,5-a]pyrimidine-3-carboxamide | 325 |
| 60 | 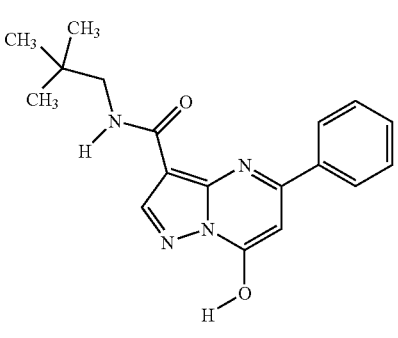 [SMILES: CC(C)(C)CNC(=O)c1cnn2c(O)cc(-c3ccccc3)nc12] | N-(2,2-dimethylpropyl)-7-hydroxy-5-phenylpyrazolo[1,5-a]pyrimidine-3-carboxamide | 325 |
| 61 | 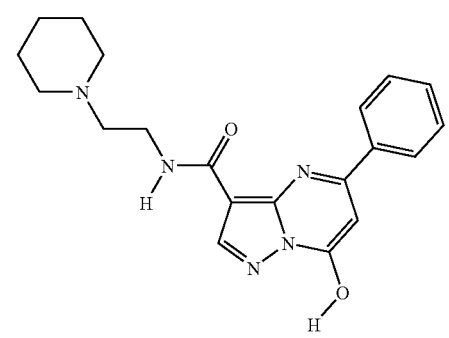 [SMILES: O=C(NCCN1CCCCC1)c1cnn2c(O)cc(-c3ccccc3)nc12] | 7-hydroxy-5-phenyl-N-(2-piperidin-1-ylethyl)pyrazolo[1,5-a]pyrimidine-3-carboxamide | 366 |
| 62 | 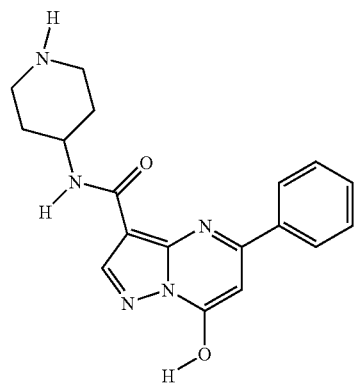 [SMILES: O=C(NC1CCNCC1)c1cnn2c(O)cc(-c3ccccc3)nc12] | 7-hydroxy-5-phenyl-N-piperidin-4-ylpyrazolo[1,5-a]pyrimidine-3-carboxamide | 338 |

TABLE 1-continued

| Cpd. No. | Structure | IUPAC Name | MS |
| --- | --- | --- | --- |
| 63 | 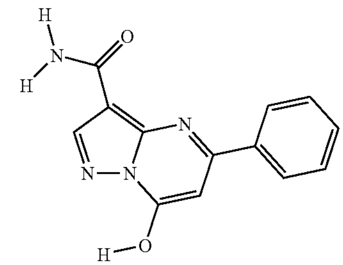 [SMILES: NC(=O)c1cnn2c(O)cc(-c3ccccc3)nc12] | 7-hydroxy-5-phenylpyrazolo[1,5-a]pyrimidine-3-carboxamide | 255 |
| 64 | 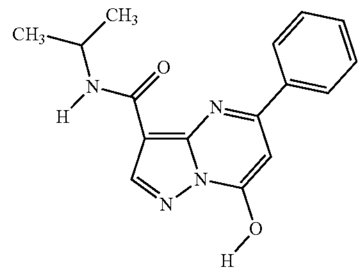 [SMILES: CC(C)NC(=O)c1cnn2c(O)cc(-c3ccccc3)nc12] | 7-hydroxy-N-(1-methylethyl)-5-phenylpyrazolo[1,5-a]pyrimidine-3-carboxamide | 297 |
| 65 | 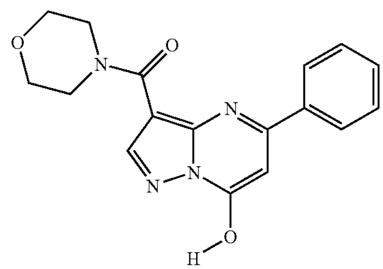 [SMILES: O=C(c1cnn2c(O)cc(-c3ccccc3)nc12)N1CCOCC1] | 3-(morpholin-4-ylcarbonyl)-5-phenylpyrazolo[1,5-a]pyrimidin-7-ol | 325 |
| 66 | 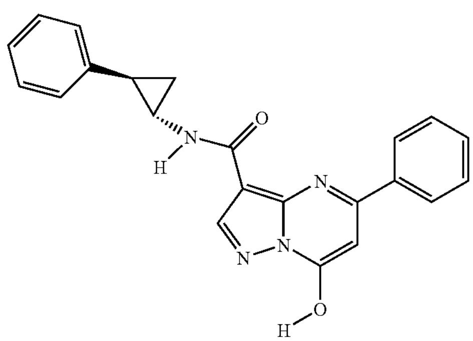 [SMILES: O=C(N[C@H]1C[C@@H]1c1ccccc1)c1cnn2c(O)cc(-c3ccccc3)nc12] | 7-hydroxy-5-phenyl-N-[(1S,2R)-2-phenylcyclopropyl]pyrazolo[1,5-a]pyrimidine-3-carboxamide | 371 |
| 67 | 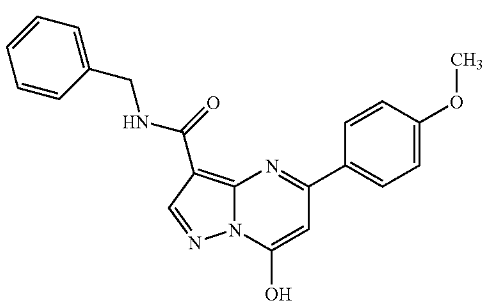 [SMILES: COc1ccc(-c2cc(O)n3ncc(C(=O)NCc4ccccc4)c3n2)cc1] | 7-hydroxy-5-[4-(methyloxy)phenyl]-N-(phenylmethyl)pyrazolo[1,5-a]pyrimidine-3-carboxamide | 375 |

TABLE 1-continued

| Cpd. No. | Structure | IUPAC Name | MS |
|---|---|---|---|
| 68 | 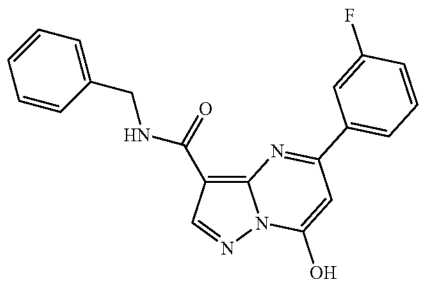 [SMILES: O=C(NCc1ccccc1)c1cnn2c(O)cc(-c3cccc(F)c3)nc12] | 5-(3-fluorophenyl)-7-hydroxy-N-(phenylmethyl)pyrazolo[1,5-a]pyrimidine-3-carboxamide | 363 |
| 69 | 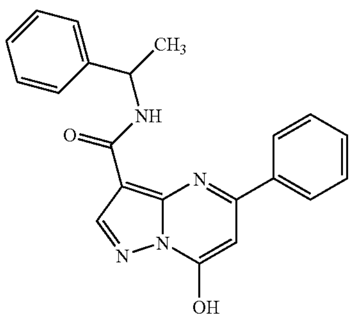 [SMILES: CC(NC(=O)c1cnn2c(O)cc(-c3ccccc3)nc12)c1ccccc1] | 7-hydroxy-5-phenyl-N-(1-phenylethyl)pyrazolo[1,5-a]pyrimidine-3-carboxamide | 359 |
| 70 | 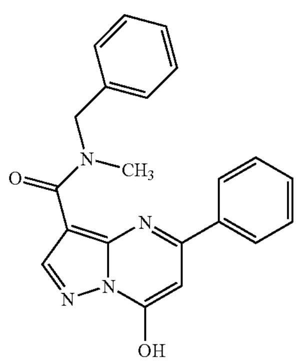 [SMILES: CN(Cc1ccccc1)C(=O)c1cnn2c(O)cc(-c3ccccc3)nc12] | 7-hydroxy-N-methyl-5-phenyl-N-(phenylmethyl)pyrazolo[1,5-a]pyrimidine-3-carboxamide | 359 |
| 71 | 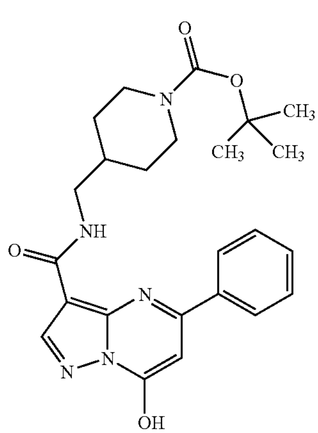 [SMILES: CC(C)(C)OC(=O)N1CCC(CNC(=O)c2cnn3c(O)cc(-c4ccccc4)nc23)CC1] | 1,1-dimethylethyl 4-({[(7-hydroxy-5-phenylpyrazolo[1,5-a]pyrimidin-3-yl)carbonyl]amino}methyl)piperidine-1-carboxylate | 452 |

TABLE 1-continued

| Cpd. No. | Structure | IUPAC Name | MS |
|---|---|---|---|
| 72 | 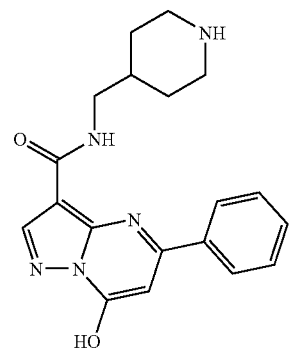 [SMILES: O=C(NCC1CCNCC1)c1cnn2c(O)cc(-c3ccccc3)nc12] | 7-hydroxy-5-phenyl-N-(piperidin-4-ylmethyl)pyrazolo[1,5-a]pyrimidine-3-carboxamide | 352 |
| 73 | 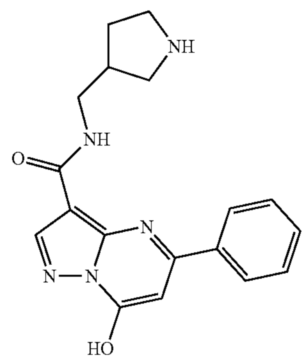 [SMILES: O=C(NCC1CCNC1)c1cnn2c(O)cc(-c3ccccc3)nc12] | 7-hydroxy-5-phenyl-N-(piperidin-3-ylmethyl)pyrazolo[1,5-a]pyrimidine-3-carboxamide | 338 |
| 74 | 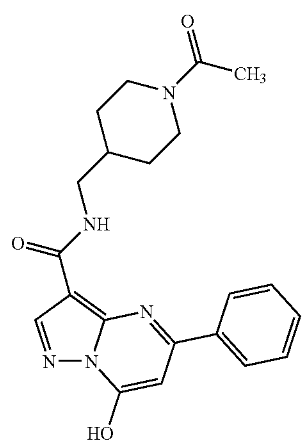 [SMILES: CC(=O)N1CCC(CNC(=O)c2cnn3c(O)cc(-c4ccccc4)nc23)CC1] | N-[(1-acetylpiperidin-4-yl)methyl]-7-hydroxy-5-phenylpyrazolo[1,5-a]pyrimidine-3-carboxamide | 394 |
| 75 | 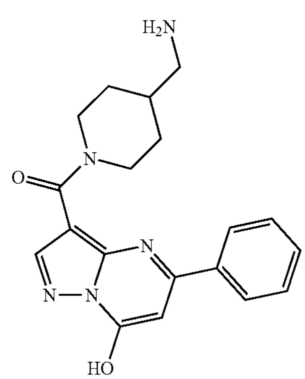 [SMILES: NCC1CCN(C(=O)c2cnn3c(O)cc(-c4ccccc4)nc23)CC1] | 3-{[4-(aminomethyl)piperidin-1-yl]carbonyl}-5-phenylpyrazolo[1,5-a]pyrimidin-7-ol | 352 |

TABLE 1-continued

| Cpd. No. | Structure | IUPAC Name | MS |
|---|---|---|---|
| 76 | 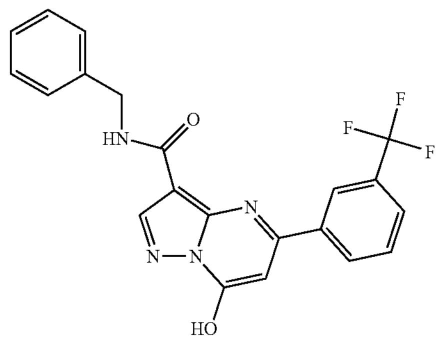 [SMILES: O=C(NCc1ccccc1)c1cnn2c(O)cc(-c3cccc(C(F)(F)F)c3)nc12] | 7-hydroxy-N-(phenylmethyl)-5-[3-(trifluoromethyl)phenyl]pyrazolo[1,5-a]pyrimidine-3-carboxamide | 413 |
| 77 | 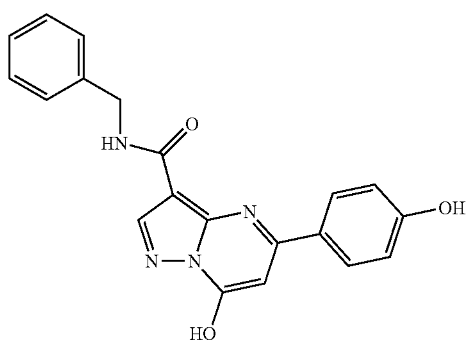 [SMILES: O=C(NCc1ccccc1)c1cnn2c(O)cc(-c3ccc(O)cc3)nc12] | 7-hydroxy-5-(4-hydroxyphenyl)-N-(phenylmethyl)pyrazolo[1,5-a]pyrimidine-3-carboxamide | 361 |
| 78 | 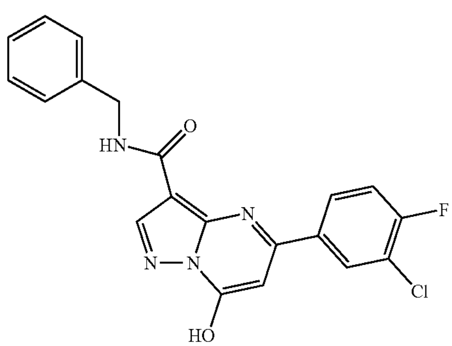 [SMILES: O=C(NCc1ccccc1)c1cnn2c(O)cc(-c3ccc(F)c(Cl)c3)nc12] | 5-(3-chloro-4-fluorophenyl)-7-hydroxy-N-(phenylmethyl)pyrazolo[1,5-a]pyrimidine-3-carboxamide | 398 |
| 79 | 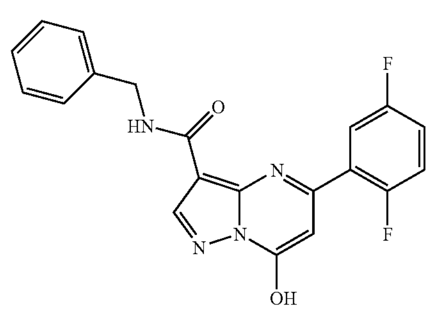 [SMILES: O=C(NCc1ccccc1)c1cnn2c(O)cc(-c3cc(F)ccc3F)nc12] | 5-(2,5-difluorophenyl)-7-hydroxy-N-(phenylmethyl)pyrazolo[1,5-a]pyrimidine-3-carboxamide | 381 |

TABLE 1-continued

| Cpd. No. | Structure | IUPAC Name | MS |
|---|---|---|---|
| 80 | 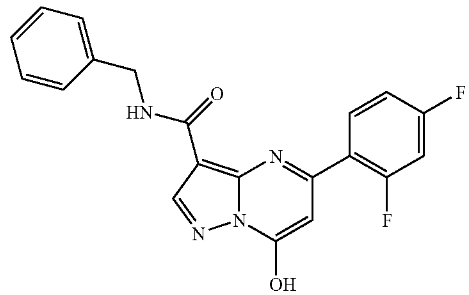 [SMILES: O=C(NCc1ccccc1)c1cnn2c(O)cc(-c3ccc(F)cc3F)nc12] | 5-(2,4-difluorophenyl)-7-hydroxy-N-(phenylmethyl)pyrazolo[1,5-a]pyrimidine-3-carboxamide | 381 |
| 81 | 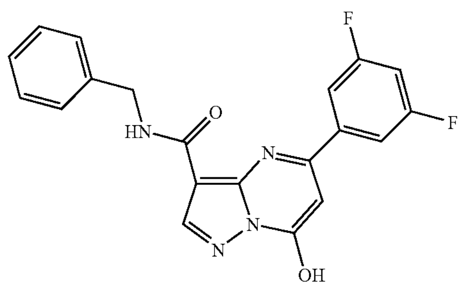 [SMILES: O=C(NCc1ccccc1)c1cnn2c(O)cc(-c3cc(F)cc(F)c3)nc12] | 5-(3,5-difluorophenyl)-7-hydroxy-N-(phenylmethyl)pyrazolo[1,5-a]pyrimidine-3-carboxamide | 381 |
| 82 | 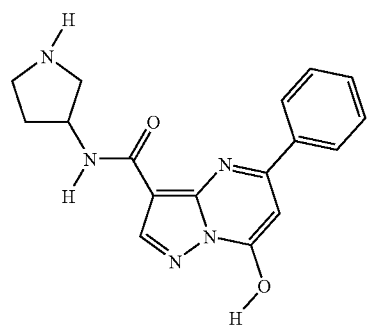 [SMILES: O=C(NC1CCNC1)c1cnn2c(O)cc(-c3ccccc3)nc12] | 7-hydroxy-5-phenyl-N-pyrrolidin-3-ylpyrazolo[1,5-a]pyrimidine-3-carboxamide | 324 |
| 83 | 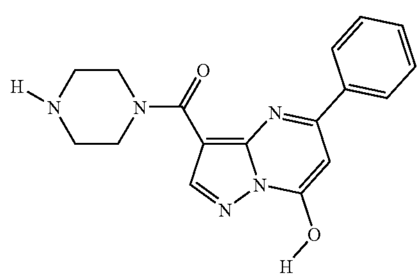 [SMILES: O=C(c1cnn2c(O)cc(-c3ccccc3)nc12)N1CCNCC1] | 5-phenyl-3-(piperazin-1-ylcarbonyl)pyrazolo[1,5-a]pyrimidin-7-ol | 324 |
| 84 | 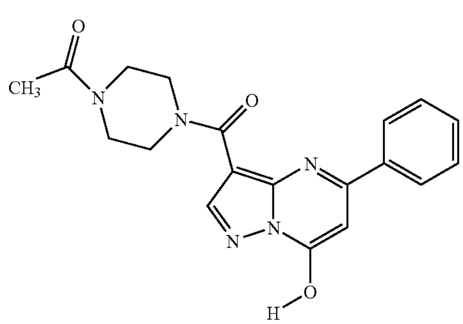 [SMILES: CC(=O)N1CCN(C(=O)c2cnn3c(O)cc(-c4ccccc4)nc23)CC1] | 3-[(4-acetylpiperazin-1-yl)carbonyl]-5-phenylpyrazolo[1,5-a]pyrimidin-7-ol | 366 |

TABLE 1-continued

| Cpd. No. | Structure | IUPAC Name | MS |
|---|---|---|---|
| 85 | 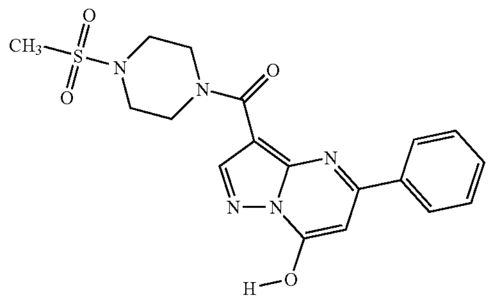 [SMILES: CS(=O)(=O)N1CCN(C(=O)c2cnn3c(O)cc(-c4ccccc4)nc23)CC1] | 3-{[4-(methylsulfonyl)piperazin-1-yl]carbonyl}-5-phenylpyrazolo[1,5-a]pyrimidin-7-ol | 402 |
| 86 | 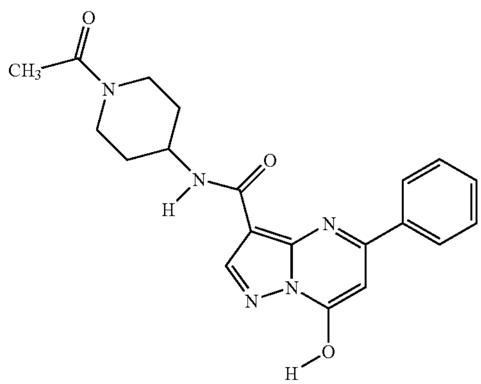 [SMILES: CC(=O)N1CCC(NC(=O)c2cnn3c(O)cc(-c4ccccc4)nc23)CC1] | N-(1-acetylpiperidin-4-yl)-7-hydroxy-5-phenylpyrazolo[1,5-a]pyrimidine-3-carboxamide | 380 |
| 87 | 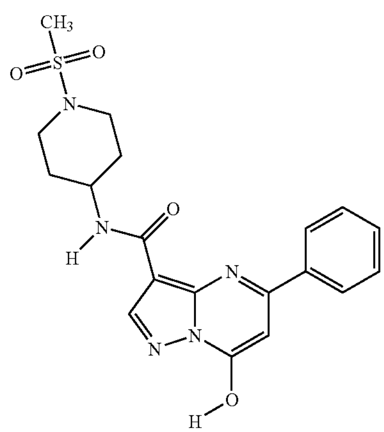 [SMILES: CS(=O)(=O)N1CCC(NC(=O)c2cnn3c(O)cc(-c4ccccc4)nc23)CC1] | 7-hydroxy-N-[1-(methylsulfonyl)piperidin-4-yl]-5-phenylpyrazolo[1,5-a]pyrimidine-3-carboxamide | 416 |
| 88 | 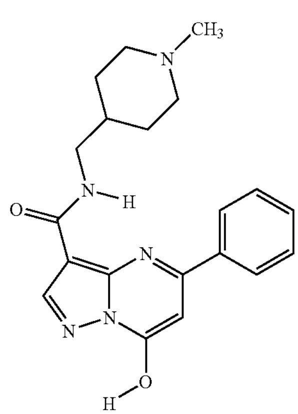 [SMILES: CN1CCC(CNC(=O)c2cnn3c(O)cc(-c4ccccc4)nc23)CC1] | 7-hydroxy-N-[(1-methylpiperidin-4-yl)methyl]-5-phenylpyrazolo[1,5-a]pyrimidine-3-carboxamide | 366 |

TABLE 1-continued

| Cpd. No. | Structure | IUPAC Name | MS |
|---|---|---|---|
| 89 | 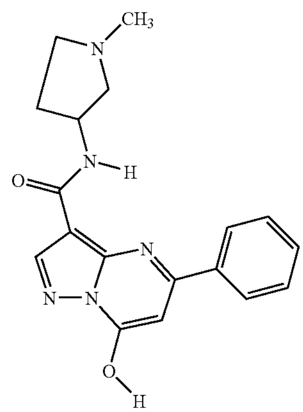 [SMILES: CN1CCC(NC(=O)c2cnn3c(O)cc(-c4ccccc4)nc23)C1] | 7-hydroxy-N-(1-methylpyrrolidin-3-yl)-5-phenylpyrazolo[1,5-a]pyrimidine-3-carboxamide | 338 |
| 90 | 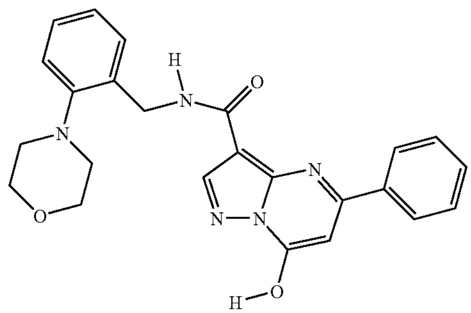 [SMILES: O=C(NCc1ccccc1N1CCOCC1)c1cnn2c(O)cc(-c3ccccc3)nc12] | 7-hydroxy-N-[(2-morpholin-4-ylphenyl)methyl]-5-phenylpyrazolo[1,5-a]pyrimidine-3-carboxamide | 430 |
| 91 | 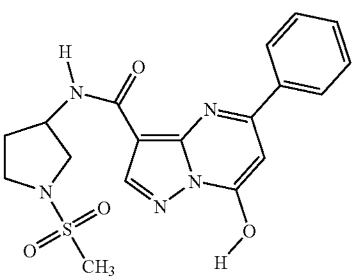 [SMILES: CS(=O)(=O)N1CCC(NC(=O)c2cnn3c(O)cc(-c4ccccc4)nc23)C1] | 7-hydroxy-N-[1-(methylsulfonyl)pyrrolidin-3-yl]-5-phenylpyrazolo[1,5-a]pyrimidine-3-carboxamide | 402 |
| 92 | 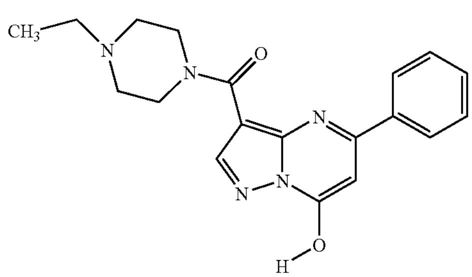 [SMILES: CCN1CCN(C(=O)c2cnn3c(O)cc(-c4ccccc4)nc23)CC1] | 3-[(4-ethylpiperazin-1-yl)carbonyl]-5-phenylpyrazolo[1,5-a]pyrimidin-7-ol | 352 |
| 93 | 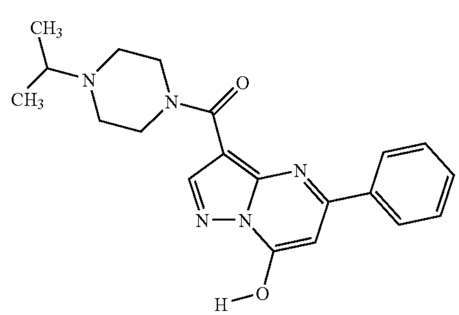 [SMILES: CC(C)N1CCN(C(=O)c2cnn3c(O)cc(-c4ccccc4)nc23)CC1] | 3-{[4-(1-methylethyl)piperazin-1-yl]carbonyl}-5-phenylpyrazolo[1,5-a]pyrimidin-7-ol | 366 |

TABLE 1-continued

| Cpd. No. | Structure | IUPAC Name | MS |
|---|---|---|---|
| 94 | 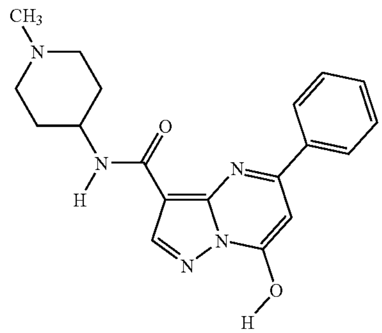 [SMILES: CN1CCC(NC(=O)c2cnn3c(O)cc(-c4ccccc4)nc23)CC1] | 7-hydroxy-N-(1-methylpiperidin-4-yl)-5-phenylpyrazolo[1,5-a]pyrimidine-3-carboxamide | 352 |
| 95 | 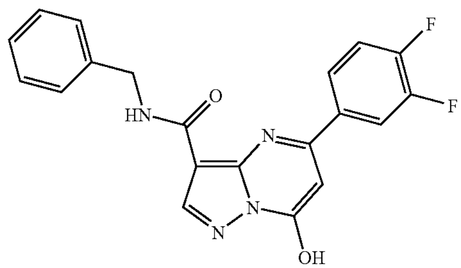 [SMILES: O=C(NCc1ccccc1)c1cnn2c(O)cc(-c3ccc(F)c(F)c3)nc12] | 5-(3,4-difluorophenyl)-7-hydroxy-N-(phenylmethyl)pyrazolo[1,5-a]pyrimidine-3-carboxamide | 381 |
| 96 | 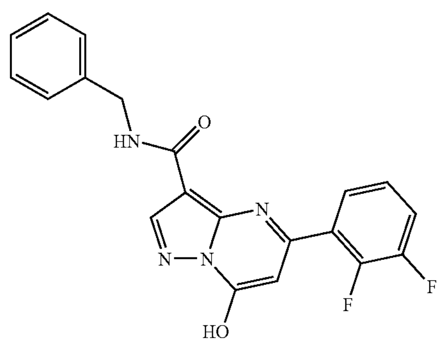 [SMILES: O=C(NCc1ccccc1)c1cnn2c(O)cc(-c3cccc(F)c3F)nc12] | 5-(2,3-difluorophenyl)-7-hydroxy-N-(phenylmethyl)pyrazolo[1,5-a]pyrimidine-3-carboxamide | 381 |
| 97 | 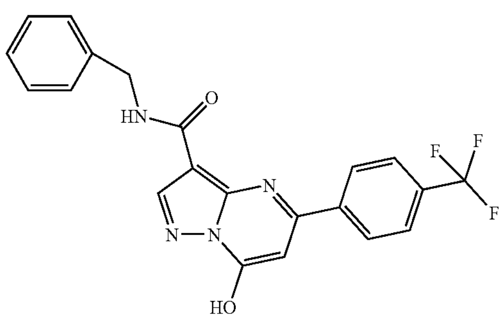 [SMILES: O=C(NCc1ccccc1)c1cnn2c(O)cc(-c3ccc(C(F)(F)F)cc3)nc12] | 7-hydroxy-N-(phenylmethyl)-5-[4-(trifluoromethyl)phenyl]pyrazolo[1,5-a]pyrimidine-3-carboxamide | 413 |
| 98 | 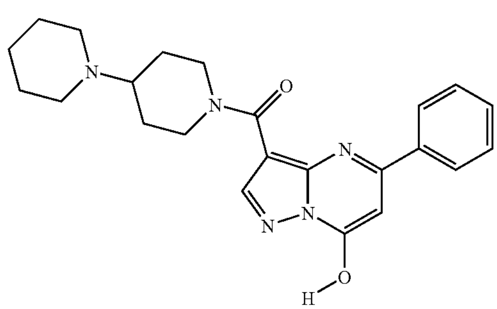 [SMILES: O=C(c1cnn2c(O)cc(-c3ccccc3)nc12)N1CCC(N2CCCCC2)CC1] | 3-(1,4'-bipiperidin-1'-ylcarbonyl)-5-phenylpyrazolo[1,5-a]pyrimidin-7-ol | 406 |

TABLE 1-continued

| Cpd. No. | Structure | IUPAC Name | MS |
|---|---|---|---|
| 99 | 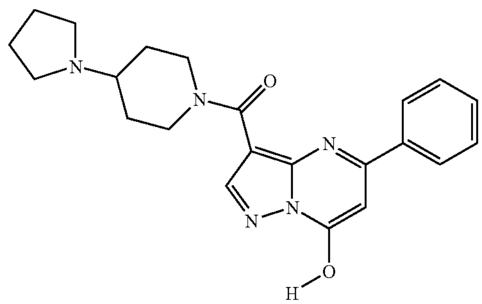 [SMILES: O=C(c1cnn2c(O)cc(-c3ccccc3)nc12)N1CCC(N2CCCC2)CC1] | 5-phenyl-3-[(4-pyrrolidin-1-ylpiperidin-1-yl)carbonyl]pyrazolo[1,5-a]pyrimidin-7-ol | 392 |
| 100 | 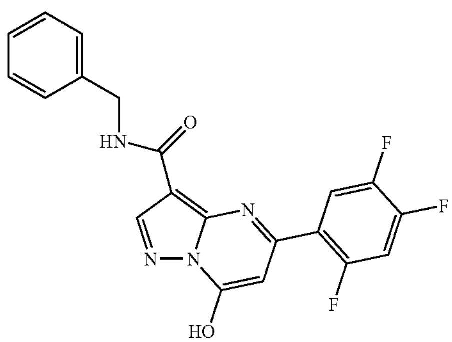 [SMILES: O=C(NCc1ccccc1)c1cnn2c(O)cc(-c3cc(F)c(F)cc3F)nc12] | 7-hydroxy-N-(phenylmethyl)-5-(2,4,5-trifluorophenyl)pyrazolo[1,5-a]pyrimidine-3-carboxamide | 399 |
| 101 | 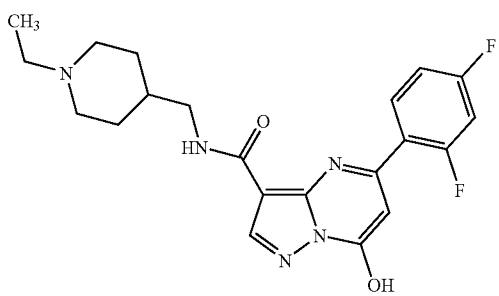 [SMILES: CCN1CCC(CNC(=O)c2cnn3c(O)cc(-c4ccc(F)cc4F)nc23)CC1] | 5-(2,4-difluorophenyl)-N-[(1-ethylpiperidin-4-yl)methyl]-7-hydroxypyrazolo[1,5-a]pyrimidine-3-carboxamide | 416 |
| 102 | 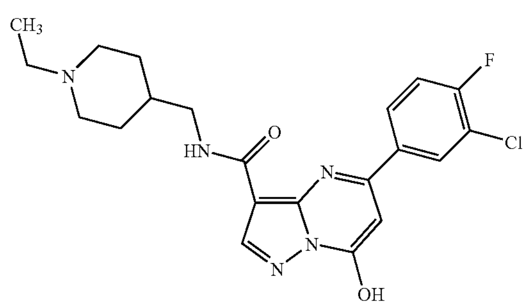 [SMILES: CCN1CCC(CNC(=O)c2cnn3c(O)cc(-c4ccc(F)c(Cl)c4)nc23)CC1] | 5-(3-chloro-4-fluorophenyl)-N-[(1-ethylpiperidin-4-yl)methyl]-7-hydroxypyrazolo[1,5-a]pyrimidine-3-carboxamide | 432 |

TABLE 1-continued

| Cpd. No. | Structure | IUPAC Name | MS |
|---|---|---|---|
| 103 | 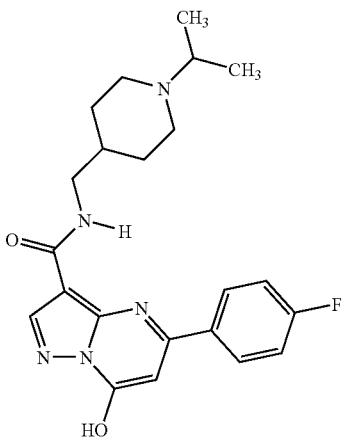 [SMILES: CC(C)N1CCC(CNC(=O)c2cnn3c(O)cc(-c4ccc(F)cc4)nc23)CC1] | 5-(4-fluorophenyl)-7-hydroxy-N-{[1-(1-methylethyl)piperidin-4-yl]methyl}pyrazolo[1,5-a]pyrimidine-3-carboxamide | 412 |
| 104 | 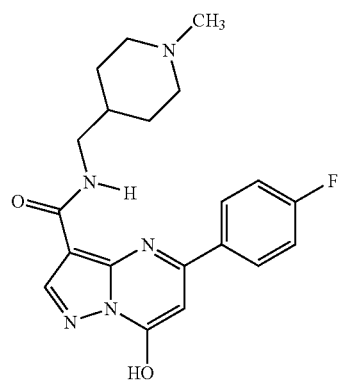 [SMILES: CN1CCC(CNC(=O)c2cnn3c(O)cc(-c4ccc(F)cc4)nc23)CC1] | 5-(4-fluorophenyl)-7-hydroxy-N-[(1-methylpiperidin-4-yl)methyl]pyrazolo[1,5-a]pyrimidine-3-carboxamide | 384 |
| 105 | 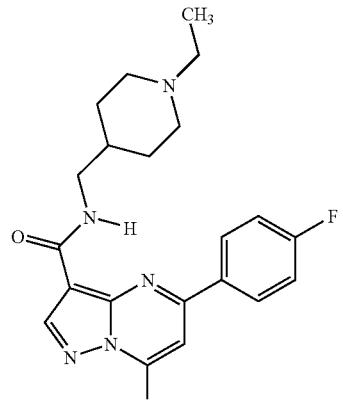 | N-[(1-ethylpiperidin-4-yl)methyl]-5-(4-fluorophenyl)-7-hydroxypyrazolo[1,5-a]pyrimidine-3-carboxamide | 398 |
| 106 | 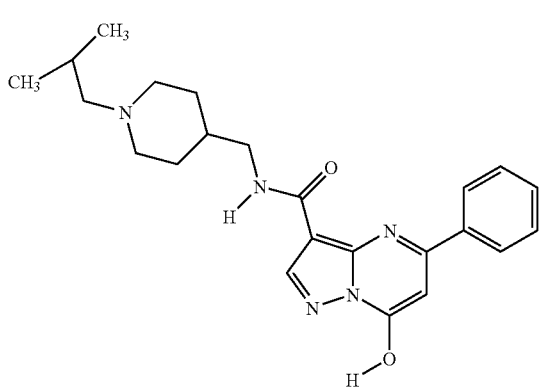 [SMILES: CC(C)CN1CCC(CNC(=O)c2cnn3c(O)cc(-c4ccccc4)nc23)CC1] | 7-hydroxy-N-{[1-(2-methylpropyl)piperidin-4-yl]methyl}-5-phenylpyrazolo[1,5-a]pyrimidine-3-carboxamide | 408 |

TABLE 1-continued

| Cpd. No. | Structure | IUPAC Name | MS |
|---|---|---|---|
| 107 | 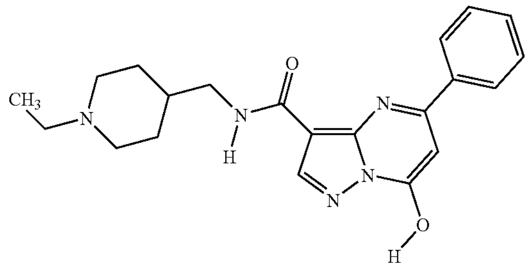 [SMILES: CCN1CCC(CNC(=O)c2cnn3c(O)cc(-c4ccccc4)nc23)CC1] | N-[(1-ethylpiperidin-4-yl)methyl]-7-hydroxy-5-phenylpyrazolo[1,5-a]pyrimidine-3-carboxamide | 380 |
| 108 | 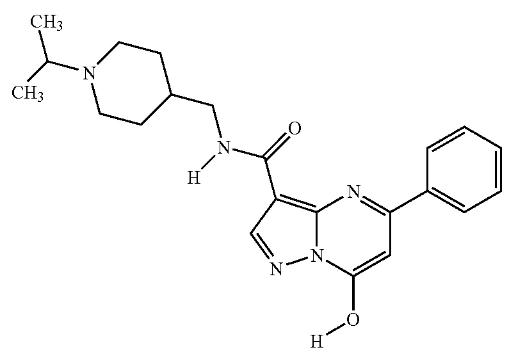 [SMILES: CC(C)N1CCC(CNC(=O)c2cnn3c(O)cc(-c4ccccc4)nc23)CC1] | 7-hydroxy-N-{[1-(1-methylethyl)piperidin-4-yl]methyl}-5-phenylpyrazolo[1,5-a]pyrimidine-3-carboxamide | 394 |
| 109 | 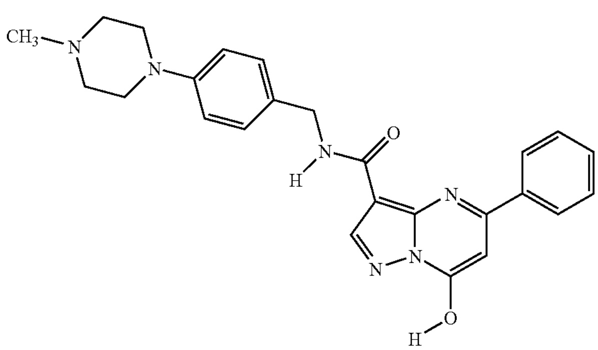 [SMILES: CN1CCN(c2ccc(CNC(=O)c3cnn4c(O)cc(-c5ccccc5)nc34)cc2)CC1] | 7-hydroxy-N-{[4-(4-methylpiperazin-1-yl)phenyl]methyl}-5-phenylpyrazolo[1,5-a]pyrimidine-3-carboxamide | 442 |
| 110 | 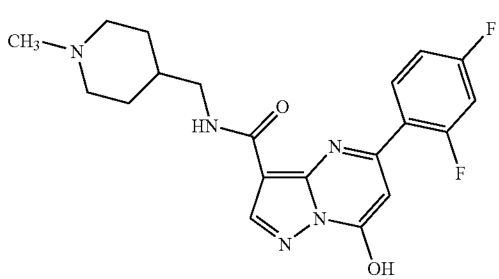 [SMILES: CN1CCC(CNC(=O)c2cnn3c(O)cc(-c4ccc(F)cc4F)nc23)CC1] | 5-(2,4-difluorophenyl)-7-hydroxy-N-[(1-methylpiperidin-4-yl)methyl]pyrazolo[1,5-a]pyrimidine-3-carboxamide | 402 |

TABLE 1-continued

| Cpd. No. | Structure | IUPAC Name | MS |
|---|---|---|---|
| 111 | 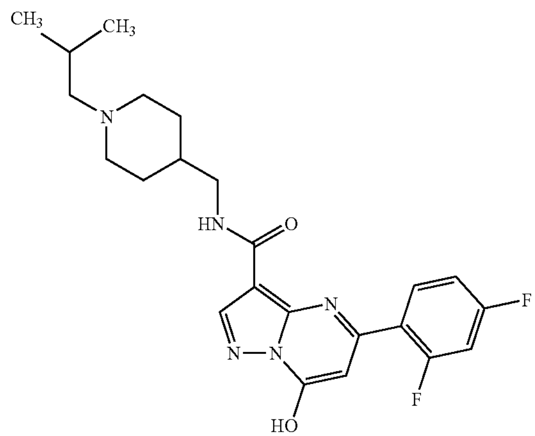 [SMILES: CC(C)CN1CCC(CNC(=O)c2cnn3c(O)cc(-c4ccc(F)cc4F)nc23)CC1] | 5-(2,4-difluorophenyl)-7-hydroxy-N-{[1-(2-methylpropyl)piperidin-4-yl]methyl}pyrazolo[1,5-a]pyrimidine-3-carboxamide | 444 |
| 112 | 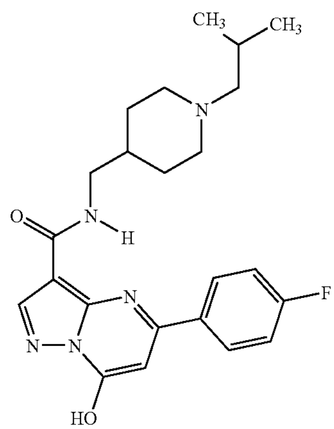 [SMILES: CC(C)CN1CCC(CNC(=O)c2cnn3c(O)cc(-c4ccc(F)cc4)nc23)CC1] | 5-(4-fluorophenyl)-7-hydroxy-N-{[1-(2-methylpropyl)piperidin-4-yl]methyl}pyrazolo[1,5-a]pyrimidine-3-carboxamide | 426 |
| 113 | 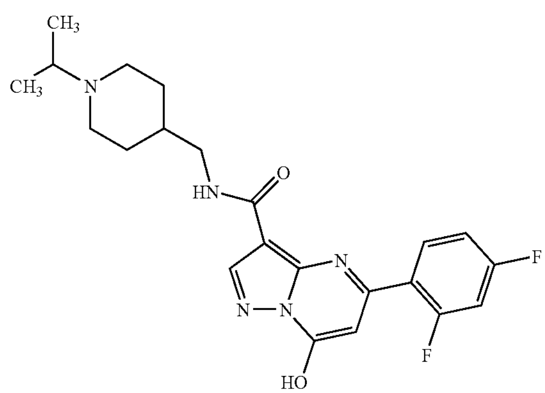 [SMILES: CC(C)N1CCC(CNC(=O)c2cnn3c(O)cc(-c4ccc(F)cc4F)nc23)CC1] | 5-(2,4-difluorophenyl)-7-hydroxy-N-{[1-(1-methylethyl)piperidin-4-yl]methyl}pyrazolo[1,5-a]pyrimidine-3-carboxamide | 430 |
| 114 | 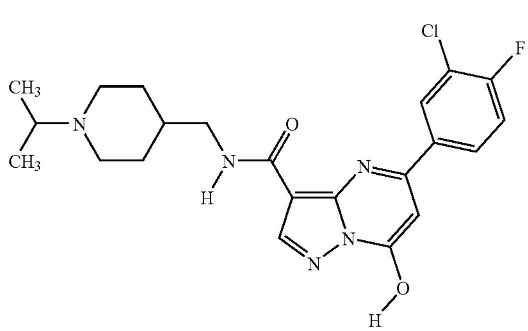 [SMILES: CC(C)N1CCC(CNC(=O)c2cnn3c(O)cc(-c4ccc(F)c(Cl)c4)nc23)CC1] | 5-(3-chloro-4-fluorophenyl)-7-hydroxy-N-{[1-(1-methylethyl)piperidin-4-yl]methyl}pyrazolo[1,5-a]pyrimidine-3-carboxamide | 446 |

TABLE 1-continued

| Cpd. No. | Structure | IUPAC Name | MS |
|---|---|---|---|
| 115 | 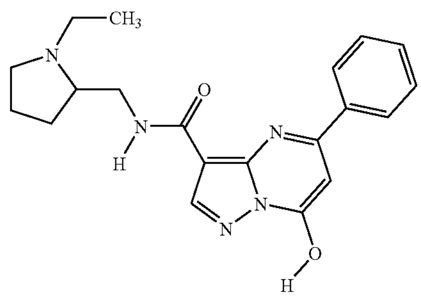 [SMILES: CCN1CCCC1CNC(=O)c1cnn2c(O)cc(-c3ccccc3)nc12] | N-[(1-ethylpyrrolidin-2-yl)methyl]-7-hydroxy-5-phenylpyrazolo[1,5-a]pyrimidine-3-carboxamide | 366 |
| 116 | 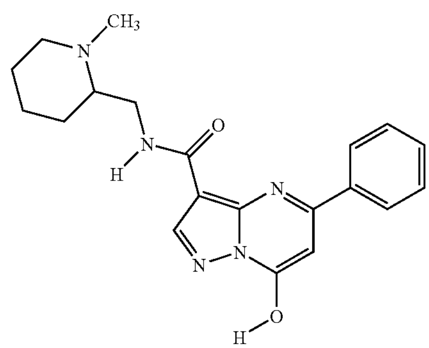 [SMILES: CN1CCCCC1CNC(=O)c1cnn2c(O)cc(-c3ccccc3)nc12] | 7-hydroxy-N-[(1-methylpiperidin-2-yl)methyl]-5-phenylpyrazolo[1,5-a]pyrimidine-3-carboxamide | 366 |
| 117 | 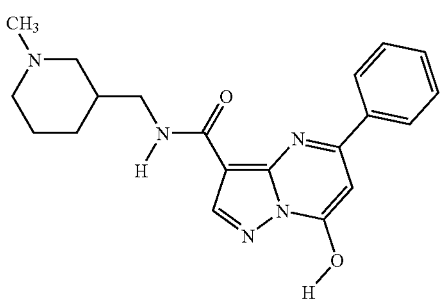 [SMILES: CN1CCCC(CNC(=O)c2cnn3c(O)cc(-c4ccccc4)nc23)C1] | 7-hydroxy-N-[(1-methylpiperidin-3-yl)methyl]-5-phenylpyrazolo[1,5-a]pyrimidine-3-carboxamide | 366 |
| 118 | 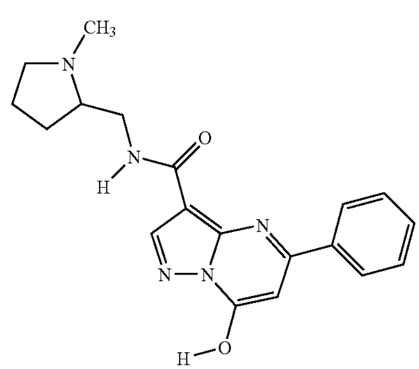 [SMILES: CN1CCCC1CNC(=O)c1cnn2c(O)cc(-c3ccccc3)nc12] | 7-hydroxy-N-[(1-methylpiperidin-2-yl)methyl]-5-phenylpyrazolo[1,5-a]pyrimidine-3-carboxamide | 352 |

TABLE 1-continued

| Cpd. No. | Structure | IUPAC Name | MS |
|---|---|---|---|
| 119 | 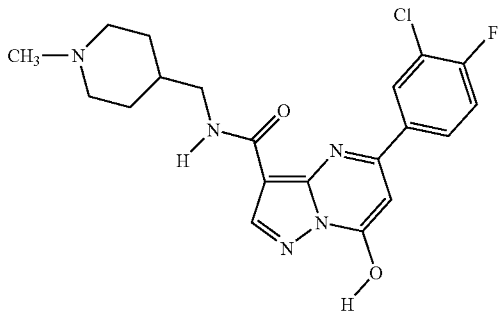 [SMILES: CN1CCC(CNC(=O)c2cnn3c(O)cc(-c4ccc(F)c(Cl)c4)nc23)CC1] | 5-(3-chloro-4-fluorophenyl)-7-hydroxy-N-[(1-methylpiperidin-4-yl)methyl]pyrazolo[1,5-a]pyrimidine-3-carboxamide | 418 |
| 120 | 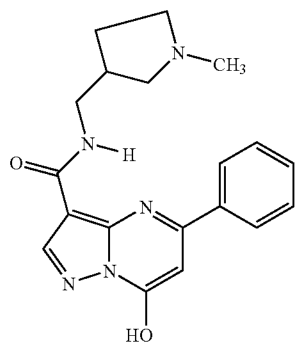 [SMILES: CN1CCC(CNC(=O)c2cnn3c(O)cc(-c4ccccc4)nc23)C1] | 7-hydroxy-N-[(1-methylpyrrolidin-3-yl)methyl]-5-phenylpyrazolo[1,5-a]pyrimidine-3-carboxamide | 352 |
| 121 | 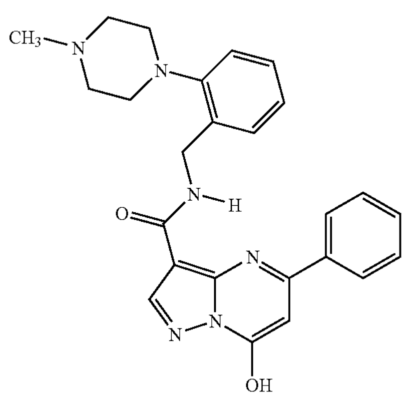 [SMILES: CN1CCN(c2ccccc2CNC(=O)c2cnn3c(O)cc(-c4ccccc4)nc23)CC1] | 7-hydroxy-N-{[2-(4-methylpiperazin-1-yl)phenyl]methyl}-5-phenylpyrazolo[1,5-a]pyrimidine-3-carboxamide | 443 |
| 122 | 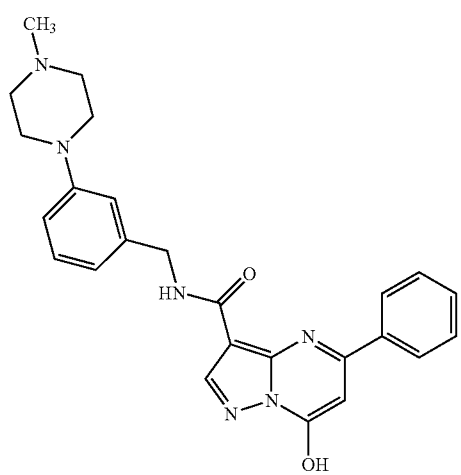 [SMILES: CN1CCN(c2cccc(CNC(=O)c3cnn4c(O)cc(-c5ccccc5)nc34)c2)CC1] | 7-hydroxy-N-{[3-(4-methylpiperazin-1-yl)phenyl]methyl}-5-phenylpyrazolo[1,5-a]pyrimidine-3-carboxamide | 443 |

Abbreviations and Definitions

The following abbreviations and terms have the indicated meanings throughout:

| Abbreviation: | Meaning: |
| --- | --- |
| Ac | Acetyl |
| ° C. | degrees Celsius |
| CBZ | CarboBenZoxy = benzyloxycarbonyl |
| D | Doublet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| l or L | liter(s) |
| M | molar or molarity |
| M | Multiplet |
| Me | Methyl |
| Mesyl | Methanesulfonyl |
| Mg or mg | milligram(s) |
| MHz | megahertz (frequency) |
| Min | minute(s) |
| mL | milliliter(s) |
| mM | Millimolar |
| Mmol | millimole(s) |
| Mol or mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| Ph | Phenyl |
| PhOH | Phenol |
| PPTS | Pyridinium p-toluenesulfonate |
| Q | Quartet |
| RT or rt | Room temperature |
| Sat'd | Saturated |
| S | Singlet |
| t | Triplet |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| uL | microliter(s) |
| uM | Micromole(s) or micromolar |
| LS/MSD | A type of Liquid Chromatography Mass Spectrometer |
| PPh₃ | Triphenylphosphine |

Definitions

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, "-----" means a single or double bond. When a group is depicted removed from its parent formula, the " $\sim\!\!\sim\!\!\sim$ " symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

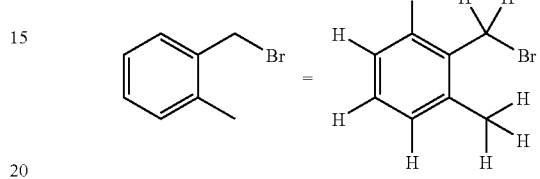

If a group "R" is depicted as "floating" on a ring system, as for example in the formula:

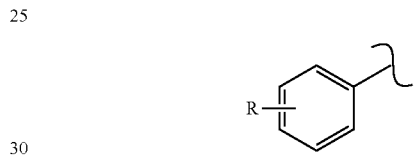

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

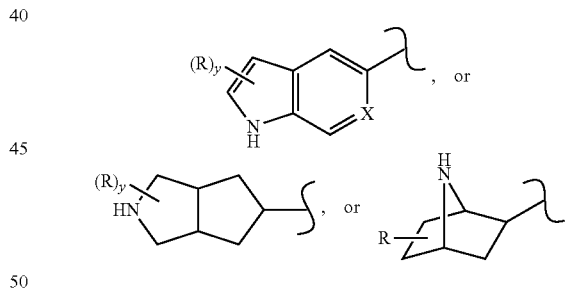

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

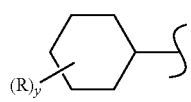

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

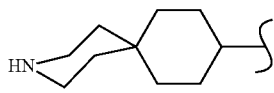

"($C_1$-$C_6$)alkyl" is intended to mean $C_1$-$C_6$ linear or branched structures and combinations thereof, inclusively. For example, "$C_6$ alkyl" can refer to an n-hexyl, iso-hexyl, and the like. "($C_1$-$C_6$)alkyl" is intended to include "($C_1$-$C_3$)alkyl. Examples of ($C_1$-$C_6$)alkyl groups include methyl, ethyl, propyl, isopropyl, butyl, s-butyl, t-butyl, isobutyl, pentyl, hexyl and the like. In this application, alkyl refers to alkanyl, alkenyl, and alkynyl residues (and combinations thereof); it is intended to include vinyl, alkyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"($C_3$-$C_{10}$)cycloalkyl" means a non-aromatic mono- or multicyclic ring system comprising about 3 to 10 carbon atoms. ($C_3$-$C_{10}$)cycloalkyl is intended to include ($C_5$-$C_6$)cycloalkyl. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkylene" is a subset of alkyl and refers to straight or branched chain divalent group consisting solely of carbon and hydrogen atoms, containing no unsaturation and having from one to six carbon atoms, for example, methylene, ethylene, propylene, n-butylene and the like. Alkylene refers to the same residues as alkyl, but having two points of attachment and, specifically, fully saturated. Examples of alkylene include ethylene (—$CH_2CH_2$—), propylene (—$CH_2CH_2CH_2$—), and dimethylpropylene (—$CH_2C(CH_3)_2CH_2$—).

"Alkylidene" is a subset of alkyl and refers to a straight or branched chain unsaturated divalent group consisting solely of carbon and hydrogen atoms, having from two to six carbon atoms, for example, ethylidene, propylidene, n-butylidene, and the like. Alkylidene refers to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"($C_1$-$C_6$)alkoxy" refers to the group O—($C_1$-$C_6$)alkyl, wherein the term "($C_1$-$C_6$)alkyl" is as defined hereinabove. "($C_1$-$C_6$)alkoxy" is intended to include ($C_1$-$C_3$)alkoxy. Examples include methoxy, ethoxy, propoxy, isopropoxy, and the like.

"($C_5$-$C_{10}$)aryl" means a monovalent five- to ten-membered mono- or multicyclic ring, wherein the monocyclic ring is aromatic and at least one of the rings in the multicyclic ring is aromatic. "($C_5$-$C_{10}$)aryl" is intended to include "($C_5$-$C_6$)aryl. Representative non-limiting examples of aryl include phenyl, naphthyl, and indanyl, and the like.

"Arylalkyl" means a residue in which an aryl moiety, as defined above, is attached to a parent structure via one of an alkylene, alkylidene, or alkylidyne group. Non-limiting examples include benzyl, phenethyl, phenylvinyl, phenylalkyl and the like.

"—($C_1$-$C_6$)alkyl-($C_5$-$C_{10}$)aryl," is intended to mean a ($C_5$-$C_{10}$)aryl moiety attached to a parent structure via ($C_1$-$C_6$) alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include —$CH_2F$, —$CHCl_2$ or —$CF_3$.

"Heteroatom" refers to O, S, N, or P.

"(4-10 membered)heterocycloalkyl" refers to a stable four- to ten-membered ring substituent that consists of carbon atoms and from one to five heteroatoms selected from the nitrogen, phosphorus, oxygen and sulfur. For purposes of this invention, the heterocycloalkyl substituent can be a monocyclic or a multicyclic ring system, which can include fused or bridged ring systems as well as spirocyclic systems.

"(5-10 membered)heteroaryl" refers to a stable five- to ten-membered ring substituent that consists of carbon atoms and from one to five heteroatoms selected from the nitrogen, phosphorus, oxygen and sulfur. For purposes of this invention, the heteroaryl substituent can be a monocyclic or a multicyclic ring system, which can include fused or bridged ring systems as well as spirocyclic systems.

In the above heteroaryl and heterocycloalkyl substituents, the nitrogen, phosphorus, carbon or sulfur atoms can be optionally oxidized to various oxidation states. In a specific example, the group —S(O)$_{0-2}$—, refers to —S-(sulfide), —S(O)-(sulfoxide), and —SO$_2$-(sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

Non-limiting examples of (4-10 membered)heterocycloalkyl and (5-10 membered)heteroaryl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

Representative examples of "(5-10 membered)heteroaryl" include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

When a group is referred to as "—(C$_1$-C$_6$)alkyl-(4-10 membered)heterocycloalkyl" the heterocycloalkyl is attached to a parent structure via one of an alkylene, alkylidene, or alkylidyne group. Examples include (4-methylpiperazin-1-yl)methyl, (morpholin-4-yl)methyl, (pyridine-4-yl) methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group can be optionally substituted.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," both the "C$_{1-8}$ alkyl" portion and the "aryl" portion of the molecule can or can not be substituted. A list of exemplary optional substitutions is presented below in the definition of "substituted."

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

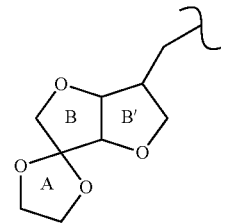

"Substituted" alkyl, aryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—CO$_2$H), carboalkoxy (that is, aryloxy or —OC(=O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that can or can not have one or more substituents, and each of the substituents can or can not have one or more substituents. But, the substituents of the substituents can not be substituted.

Some of the compounds of the invention can have imino, amino, oxo or hydroxy substituents off aromatic heterocyclyl systems. For purposes of this disclosure, it is understood that such imino, amino, oxo or hydroxy substituents can exist in their corresponding tautomeric form; i.e., amino, imino, hydroxy or oxo, respectively.

The compounds of the invention, or their pharmaceutically acceptable salts, can have asymmetric carbon atoms, oxidized sulfur atoms or quaternized nitrogen atoms in their structure.

The compounds of the invention and their pharmaceutically acceptable salts can exist as single stereoisomers, racemates, and as mixtures of enantiomers and diastereomers. The compounds can also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners can be bound to the particular group at one end, and the other partner is necessarily bound to the other end of the particular group, unless stated explicitly otherwise. Stated another way, divalent groups are not to be construed as limited to the depicted orientation, for example "—OCH$_2$—" is meant to mean not only "—OCH$_2$—" as drawn, but also "—CH$_2$O—."

In addition to the various embodiments recited hereinabove, also encompassed by this invention are combinations of the embodiments described herein.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular CK2-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In the second aspect, the invention provides pharmaceutical compositions comprising an inhibitor of CK2 according to the invention and a pharmaceutically acceptable carrier, excipient, or diluent. In certain other preferred embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example CK2, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, CK2 may be done in a number of ways. In one example, the candidate agent (the compound of the invention) is labeled, for example, with a fluorescent or radioactive moiety and binding determined directly. For example, this may be done by attaching all or a portion of the CK2 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, CK2 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to CK2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to CK2 protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to CK2 and thus is capable of binding to, and potentially modulating, the activity of the CK2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to CK2 with a higher affinity. Thus, if the candidate agent is labeled, the presence of the label on the support, coupled with a lack of competitor binding, may indicate the candidate agent is capable of binding to CK2.

It may be of value to identify the binding site of CK2. This can be done in a variety of ways. In one embodiment, once CK2 is identified as binding to the candidate agent, the CK2 is fragmented or modified and the assays repeated to identify the necessary components for binding.

Modulation is tested by screening for candidate agents capable of modulating the activity of CK2 comprising the steps of combining a candidate agent with CK2, as above, and determining an alteration in the biological activity of the CK2. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native CK2, but cannot bind to modified CK2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular CK2-ligand complexes, and their corresponding x-ray structure coordinates can be used to reveal new structural information useful for understanding the biological activity of CK2 kinases as described herein. As well, the key structural features of the aforementioned proteins, particularly, the shape of the ligand binding site, are useful in methods for designing or identifying selective modulators of CK2 kinases and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of CK2 kinases. Such methods may be characterized by the following aspects: a) introducing into a suitable computer program, information defining a ligand binding domain of a CK2 kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for CK2 kinase modulation, and determining whether said candidate agent modulates CK2 kinase activity in the assay. Such methods may also include administering the candidate agent, determined to modulate CK2 kinase activity, to a mammal suffering from a condition treatable by CK2 kinase modulation, such as those described above.

Also, one skilled in the art would appreciate that compounds of the invention can be used in a method of evaluating the ability of a test agent to associate with a molecule or molecular complex comprising a ligand binding domain of a CK2 kinase. Such a method may be characterized by the following aspects: a) creating a computer model of a CK2 kinase binding pocket using structure coordinates obtained from suitable x-ray quality crystals of the CK2 kinase, b) employing computational algorithms to perform a fitting operation between the test agent and the computer model of the binding pocket, and c) analyzing the results of the fitting operation to quantify the association between the test agent and the computer model of the binding pocket.

Synthetic Procedures

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] or [M+Na] ion (positive mode) or [M−1] ion (negative mode). $^1$H-NMR data for compounds was taken with a Varian AS400 Spectrometer (400 MHz, available from Varian GmbH, Darmstadt, Germany).

Synthesis of Compounds:

Compounds of the invention may generally be prepared by the sequence outlined in Scheme 1 starting from the condensation of commercially available ethyl 5-amino-1H-pyrazole-4-carboxylate (1) ($R_7$=H) with a ketoester (2) to give a 7-hydroxy-pyrazolo[1,5-a]pyrimidine-3-carboxylate (3). One such method that is useful for carrying

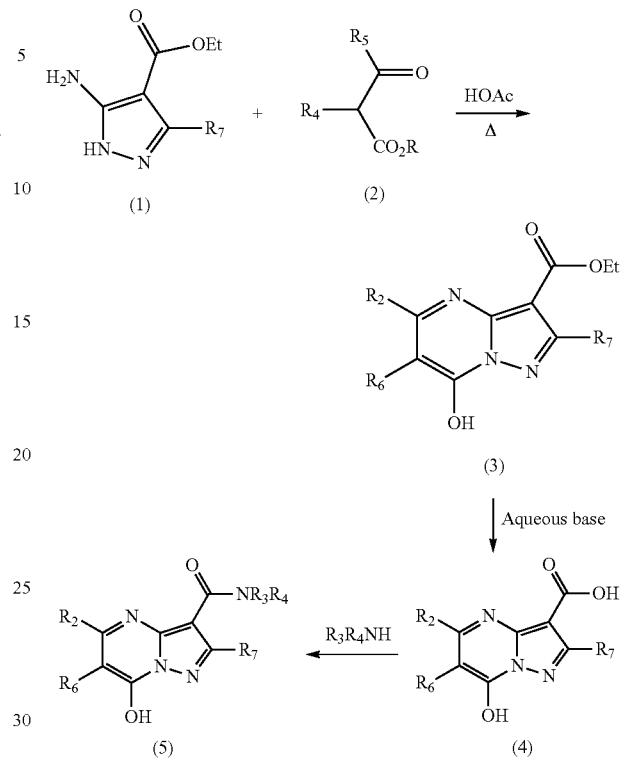

Scheme 1 out the condensation involves heating the components together in acetic acid. Hydrolysis of the carboxylic ester (3) to give the corresponding acid is readily carried out under standard conditions to afford carboxylic acid (4). Thus, heating (3) in an aqueous methanol solution in the presence of a base such as an alkali metal hydroxide followed by removal of the methanol and acidification with aqueous mineral acid generally results in precipitation or crystallization of the desired carboxylic acid, which may be isolated using simple filtration techniques. Introduction then of the 3-position carboxamide to give compounds of the invention represented by (5) may be carried out using straightforward amide coupling methodologies that are well known in the art.

Compounds of the invention wherein the 2-position is substituted by an aminoalkyl group ($R_3$=NHR$_6$ or NR$_6$R$_7$) may be prepared by making use of methods known in the art, see: Zaki, M. E. A.; Fathalla, O. A. Synthesis of new pyrazolo[1,5-a]pyrimidines and pyrazolo[1,5-a]triazines utilizing ketene S,S acetals. Indian Journal of Heterocyclic Chemistry (1997), 7(2), 113-118. As outlined in Scheme 2, ethyl 2-cyano-3,3-bis(methylthio)acrylate (6) may be sequentially reacted with an amine of choice to give

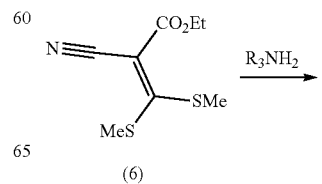

Scheme 2

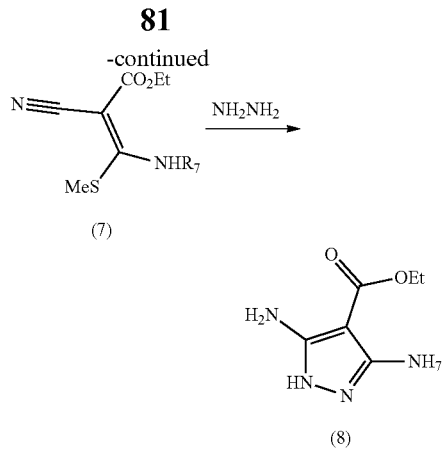

an intermediate such as (7) followed then by cyclization to afford the suitably functionalized 3,5-diaminopyrazole carboxylate (8). The diaminopyrazole thus obtained may be carried forward in the usual manner as illustrated in scheme 1. Alternatively, compounds of the invention where the 2-position is alkyl substituted ($R_3$=alkyl) can be prepared analogously from the appropriate 3-alkyl-5-aminopyrazole carboxylate. The preparation of such intermediates is well established, see: 1) Baba, Hideo; Hori, Isaburo; Hayashi, Toshio; Midorikawa, Hiroshi. Reactions of α-cyano-β-methoxy-β-alkylacrylic esters with hydrazine and hydroxylamine. Bulletin of the Chemical Society of Japan (1969), 42(6), 1653-9. 2) Alberola, A.; Antolin, L. F.; Gonzalez, A. M.; Laguna, M. A.; Pulido, F. J. Base-induced ring cleavage of 4-functionalized 3-unsubstituted isoxazoles. Synthesis of 5-amino azoles and 4-cyano azoles. Journal of Heterocyclic Chemistry (1986), 23(4), 1035-8. 3) Huppatz, John L. Systemic fungicides. The synthesis of pyrazolo[1,5-a]pyrimidine analogs of carboxin. Australian Journal of Chemistry (1985), 38(1), 221-30.

The following examples serve to provide further appreciation of the invention, but are not meant in any way to restrict the effective scope of the invention.

EXAMPLE 1

5-phenyl-3-[(4-phenylpiperazin-1-yl)carbonyl]pyrazolo[1,5-α]pyrimidin-7-ol hydrochloride (Compound 33)

Step 1: Commercially available ethyl 5-amino-1H-pyrazole-4-carboxylate (5.0 g, 32 mmol) was taken into glacial acetic acid (3.2 mL) followed by addition of ethyl 3-oxo-3-phenylpropanoate (6.1 mL, 35 mmol) and the mixture was refluxed for 12 h. The mixture was allowed to cool to room temperature and concentrated in vacuo. The crude solid was recrystallized (ethanol) and collected to yield 3.1 g (61%) of crystalline ethyl 7-hydroxy-5-phenylpyrazolo[1,5-a]pyrimidine-3-carboxylate. $^1$H NMR (400 MHz, $d_6$-DMSO): 11.75 (s, 1H), 8.28 (s, 1H), 7.80 (m, 2H), 7.61 (m, 3H), 6.28 (s, 1H), 4.31 (q, 2H), 1.34 (t, 3H).

Step 2: Ethyl 7-hydroxy-5-phenylpyrazolo[1,5-a]pyrimidine-3-carboxylate (3.1 g, 11 mmol) was taken into 27 mL methanol and 2 M aqueous lithium hydroxide (27 mL) and heated in an 80° C. oil bath for 4 h. The solution was allowed to cool to room temperature and concentrated in vacuo to remove methanol. The subsequent basic aqueous mixture was washed with ethyl acetate (10% methanol) and then acidified to pH 3 using concentrated hydrochloric acid. A solid formed and was collected via vacuum filtration to yield 2.2 g (79%) of crystalline 7-hydroxy-5-phenylpyrazolo[1,5-c]pyrimidine-3-carboxylic acid. $^1$H NMR (400 MHz, $d_6$-DMSO): 8.21 (s, 1H), 7.76 (m, 2H), 7.57 (m, 3H), 6.24 (s, 1H).

Step 3: 7-Hydroxy-5-phenylpyrazolo[1,5-a]pyrimidine-3-carboxylic acid (0.075 g, 0.29 mmol) was taken up in a solution of 0.35 M HOAt in DMF (1.0 mL, 0.35 mmol), followed by addition of 0.29 M HATU in DMF (1.0 mL, 0.29 mmol). N-Methylmorpholine (0.064 mL, 0.58 mmol) was added and the mixture was stirred for 15 min. at room temperature. 1-Phenylpiperazine (0.054 mL, 0.35 mmol) was added and the resultant mixture was stirred at 60° C. for 12 h. The solution was allowed to cool to room temperature and the solvent was removed in vacuo. The residue was partitioned between ethyl acetate (10% methanol) and 0.5 M aqueous hydrochloric acid, resulting in a white solid, which was collected via vacuum filtration and dried to give 0.052 g (41%) of 5-phenyl-3-[(4-phenylpiperazin-1-yl)carbonyl]pyrazolo[1,5-a]pyrimidin-7-ol hydrochloride. $^1$H NMR (400 MHz, $d_6$-DMSO): 12.15 (s, 1H), 8.21 (s, 1H), 7.80 (m, 2H), 7.58 (m, 3H), 7.31 (m, 2H), 7.20 (m, 2H), 6.97 (m, 1H), 6.20 (s, 1H), 3.89 (m, 4H), 3.34 (m, 41-1). MS (EI) for $C_{23}H_{21}N_5O_2$: 400 ($MH^+$).

Using the same or analogous synthetic techniques described in Example 1 and/or substituting with alternative reagents, the compounds shown in Table 2 were prepared.

EXAMPLE 2

N-(biphenyl-4-ylmethyl)-7-hydroxy-5-methylpyrazolo[1,5-a]pyrimidine-3-carboxamide N-(biphenyl-4-ylmethyl)-7-hydroxy-5-methylpyrazolo[1,5-a]pyrimidine-3-carboxamide was prepared according to the method of Example 1 by replacing ethyl 3-oxo-3-phenyl-propionate with commercially available ethyl acetoacetate in step 1, and replacing of 1-phenylpiperazine with commercially available 4-phenylbenzylamine in step 3. $^1$H NMR (400 MHz, $d_6$-DMSO): 11.74 (s, 1H), 8.97 (t, 1H), 8.40 (s, 1H), 7.63-7.66 (m, 4H), 7.45 (q, 4H), 7.34-7.37 (m, 1H), 5.76 (s, 1H), 4.52 (d, 2H), 2.38 (s, 3H).

EXAMPLE 3

N-[(2-bromophenyl)methyl]-7-hydroxy-5-methylpyrazolo[1,5-a]pyrimidine-3-carboxamide N-[(2-bromophenyl)methyl]-7-hydroxy-5-methylpyrazolo[1,5-a]pyrimidine-3-carboxamide was prepared according to the method of Example 1 by replacing ethyl 3-oxo-3-phenylpropionate with commercially available ethyl acetoacetate in step 1, and replacing of 1-phenylpiperazine with commercially available 2-bromobenzylamine in step 3. $^1$H NMR (400 MHz, $d_6$-DMSO): 11.74 (s, 1H), 8.96 (t, 1H), 8.44 (s, 1H), 7.63 (d, 1H), 7.36-7.41 (m, 2H), 7.21-7.25 (m, 1H), 5.77 (s, 1H), 4.53 (d, 2H), 2.37 (s, 3H).

EXAMPLE 4

7-hydroxy-5-methyl-N-[(3-nitrophenyl)methyl]pyrazolo[1,5-a]pyrimidine-3-carboxamide 7-hydroxy-5-methyl-N-[(3-nitrophenyl)methyl]pyrazolo[1,5-a]pyrimidine-3-carboxamide was prepared according to the method of Example 1 by replacing ethyl 3-oxo-3-phenyl-propionate with commercially available ethyl acetoacetate in step 1, and replacing 1-phenylpiperazine with commercially available 3-nitrobenzylamine in step 3.

$^1$H NMR (400 MHz, d$_6$-DMSO): 11.75 (s, 1H), 9.08 (t, 1H), 8.38 (s, 1H), 8.21 (t, 1H), 8.12-8.15 (m, 1H), 7.81 (d, 1H), 7.66 (t, 1H), 5.77 (s, 1H), 4.60 (d, 2H), 2.37 (s, 3H).

EXAMPLE 5

N-[(3-bromophenyl)methyl]-7-hydroxy-5-methylpyrazolo[1,5-a]pyrimidine-3-carboxamide N-[(3-bromophenyl)methyl]-7-hydroxy-5-methylpyrazolo[1,5-a]pyrimidine-3-carboxamide was prepared according to the method of Example 1 by replacing ethyl 3-oxo-3-phenylpropionate with commercially available ethyl acetoacetate in step 1, and replacing 1-phenylpiperazine with commercially available 3-bromobenzylamine in step 3. $^1$H NMR (400 MHz, d$_6$-DMSO): 11.70 (s, 1H), 8.93 (t, 1H), 8.34 (s, 1H), 7.51 (s, 1H), 7.43 (d, 1H), 7.27-7.34 (m, 2H), 5.74 (s, 1H), 4.46 (d, 2H), 2.37 (s, 3H).

EXAMPLE 6

7-hydroxy-5-methyl-N-[(2-nitrophenyl)methyl]pyrazolo[1,5-a]pyrimidine-3-carboxamide 7-hydroxy-5-methyl-N-[(2-nitrophenyl)methyl]pyrazolo[1,5-a]pyrimidine-3-carboxamide was prepared according to the method of Example 1 by replacing ethyl 3-oxo-3-phenylpropionate with commercially available ethyl acetoacetate in step 1, and replacing 1-phenylpiperazine with commercially available 2-nitrobenzylamine in step 3.
$^1$H NMR (400 MHz, d$_5$-DMSO): 11.68 (s, 1H), 9.00 (t, 1H), 8.39 (s, 1H), 8.02 (dd, 1H), 7.72 (td, 1H), 7.59 (d, 1H), 7.52 (t, 1H), 5.75 (s, 1H), 4.74 (d, 2H), 2.35 (s, 3H).

EXAMPLE 7

7-hydroxy-N-[(4-iodophenyl)methyl]-5-methylpyrazolo[1,5-a]pyrimidine-3-carboxamide (Compound 12)

7-hydroxy-N-[(4-iodophenyl)methyl]-5-methylpyrazolo[1,5-a]pyrimidine-3-carboxamide was prepared according to the method of Example 1 by replacing of ethyl 3-oxo-3-phenylpropionate with commercially available ethyl acetoacetate in step 1 and replacing 1-phenylpiperazine with commercially available 4-iodobenzylamine in step 3.
$^1$H NMR (400 MHz, d$_6$-DMSO): 11.72 (s, 1H), 8.94 (t, 1H), 8.36 (s, 1H), 7.70 (d, 2H), 7.15 (d, 2H), 5.76 (s, 1H), 4.43 (d, 2H), 2.37 (s, 3H).

EXAMPLE 8

7-hydroxy-5-methyl-N-{[2-(methylthio)phenyl]methyl}pyrazolo[1,5-a]pyrimidine-3-carboxamide (Compound 13)

7-hydroxy-5-methyl-N-{[2-(methylthio)phenyl]methyl}pyrazolo[1,5-a]pyrimidine-3-carboxamide was prepared according to the method of example 1 by replacing ethyl 3-oxo-3-phenylpropionate with commercially available ethyl acetoacetate in step 1, and replacing 1-phenylpiperazine with commercially available 2-nitrobenzylamine in step 3. $^1$H NMR (400 MHz, d$_6$-DMSO): 11.72 (s, 1H), 8.94 (t, 1H), 8.36 (s, 1H), 7.70 (d, 2H), 7.15 (d, 2H), 5.76 (s, 1H), 4.43 (d, 2H), 2.37 (s, 3H).

EXAMPLE 9

7-hydroxy-5-methyl-N-{[3-(phenyloxy)phenyl]methyl}pyrazolo[1,5-a]pyrimidine-3-carboxamide (Compound 14)

7-hydroxy-5-methyl-N-{[3-(phenyloxy)phenyl]methyl}pyrazolo[1,5-a]pyrimidine-3-carboxamide was prepared according to the method of Example 1 by replacing ethyl 3-oxo-3-phenylpropionate with commercially available ethyl acetoacetate in step 1 and replacing 1-phenylpiperazine with commercially available 3-(phenyloxy)benzylamine in step 3.
$^1$H NMR (400 MHz, d$_6$-DMSO): 11.72 (s, 1H), 8.93 (t, 1H), 8.36 (s, 1H), 7.33-7.40 (m, 3H), 7.11-7.14 (m, 2H), 6.98-7.01 (m, 3H), 6.88 (dd, 1H), 5.76 (s, 1H0, 4.47 (d, 2H), 2.38 (s, 3H).

EXAMPLE 10

7-hydroxy-5-methyl-N-{[4-(phenyloxy)phenyl]methyl}pyrazolo[1,5-a]pyrimidine-3-carboxamide (Compound 15)

7-hydroxy-5-methyl-N-{[4-(phenyloxy)phenyl]methyl}pyrazolo[1,5-a]pyrimidine-3-carboxamide was prepared according to the method of example 1 by replacing ethyl 3-oxo-3-phenylpropionate with commercially available ethyl acetoacetate in step 1 and replacing 1-phenylpiperazine with commercially available 4-(phenyloxy)benzylamine in step 3.
$^1$H NMR (400 MHz, d$_6$-DMSO): 11.74 (s, 1H), 8.93 (t, 1H), 8.39 (s, 1H), 7.36-7.41 (m, 4H), 7.10-7.14 (m, 1H), 6.97-7.02 (m, 4H), 5.76 (s, 1H), 4.47 (d, 2H), 2.39 (s, 3H).

EXAMPLE 11

7-hydroxy-N-{[3-(4-methylpiperazin-1-yl)phenyl]methyl}-5-phenylpyrazolo[1,5-a]pyrimidine-3-carboxamide (Example 130)

7-hydroxy-N-{[3-(4-methylpiperazin-1-yl)phenyl]methyl}-5-phenylpyrazolo[1,5-a]pyrimidine-3-carboxamide was prepared according to the method of Example 1 by replacing 1-phenylpiperazine with commercially available 3-(1-methylpiperazin-4-yl)benzylamine in step 3. $^1$H NMR (400 MHz, d$_6$-DMSO): 11.36-11.22 (br. s, 1H), 10.82-10.67 (br. s, 1H), 9.10-9.03 (m, 1H), 8.49 (s, 1H), 7.83-7.78 (m, 2H), 7.64-7.54 (m, 3H), 7.25-7.17 (m, 1H), 6.98 (s, 1H), 6.92-6.81 (m, 2H), 6.28 (s, 1H), 4.49-4.42 (m, 2H), 3.86-3.64 (m, 2H), 3.52-3.42 (m, 2H), 3.19-2.99 (m, 4H), 2.79 (m, 3H).

EXAMPLE 12

7-hydroxy-5-phenyl-N-(phenylmethyl)pyrazolo[1,5-a]pyrimidine-3-carboxamide (Compound 16)

7-hydroxy-5-phenyl-N-(phenylmethyl)pyrazolo[1,5-a]pyrimidine-3-carboxamide was prepared according to the method of Example 1 by replacing 1-phenylpiperazine with commercially available benzylamine in step 3. $^1$H NMR (400 MHz, d$_6$-DMSO): 11.33 (broad s, 1H), 9.05 (t, 1H), 8.46 (s, 1H), 7.83 (dd, 2H), 7.61 (m, 3H), 7.34 (m, 5H), 6.30 (s, 1H), 4.52 (d, 2H).

EXAMPLE 13

5-ethyl-7-hydroxy-N-(phenylmethyl)pyrazolo[1,5-a]pyrimidine-3-carboxamide (Compound 17)

5-ethyl-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-oxopentanoate in step 1 and by replacing 1-phenylpiperazine with commercially available benzylamine in step 3.

$^1$H NMR (400 MHz, $d_6$-DMSO): 11.61 (s, 1H), 8.95-8.89 (m, 1H), 8.38 (s, 1H), 7.34-7.28 (m, 4H), 7.26-7.20 (m, 1H), 5.75-5.73 (m, 1H), 4.48-4.44 (m, 2H), 2.71 (q, 2H), 1.16 (t, 3H).

EXAMPLE 14

7-hydroxy-5-methyl-N-[(3-methylphenyl)methyl]pyrazolo[1,5-a]pyrimidine-3-carboxamide (Compound 18)

7-hydroxy-5-methyl-N-[(3-methylphenyl)methyl]pyrazolo[1,5-a]pyrimidine-3-carboxamide was prepared according to the method of Example 1 by replacing ethyl 3-oxo-3-phenylpropionate with commercially available ethyl acetoacetate in step 1 and by replacing 1-phenylpiperazine with commercially available 3-methylbenzylamine in step 3.

$^1$H NMR (400 MHz, $d_6$-DMSO): 11.72 (s, 1H), 8.89 (t, 1H), 8.38 (s, 1H), 7.22 (t, 1H), 7.12-7.17 (m, 2H), 7.06 (d, 1H), 5.76 (s, 1H), 4.44 (d, 2H), 2.38 (s, 3H), 2.29 (s, 3H).

EXAMPLE 15

7-hydroxy-N-[3-iodophenyl)methyl]-5-methylpyrazolo[1,5-a]pyrimidine-3-carboxamide (Compound 19)

7-hydroxy-N-[(3-iodophenyl)methyl]-5-methylpyrazolo[1,5-a]pyrimidine-3-carboxamide was prepared according to the method of example 1 by replacing ethyl 3-oxo-3-phenylpropionate with commercially available ethyl acetoacetate in step 1 and by replacing 1-phenylpiperazine with commercially available 3-iodobenzylamine in step 3.

$^1$H NMR (400 MHz, $d_6$-DMSO): 11.74 (s, 1H), 8.94 (t, 1H), 8.37 (s, 1H), 7.71 (s, 1H), 7.62 (d, 1H), 7.36 (d, 1H), 7.15 (t, 1H), 5.76 (s, 1H), 4.43 (d, 2H), 2.38 (s, 3H).

EXAMPLE 16

7-hydroxy-5-methyl-N-{[3-(trifluoromethyl)phenyl]methyl}pyrazolo[1,5-a]pyrimidine-3-carboxamide (Compound 20)

7-hydroxy-5-methyl-N-{[3-(trifluoromethyl)phenyl]methyl}pyrazolo[1,5-a]pyrimidine-3-carboxamide was prepared according to the method of example one by replacing ethyl 3-oxo-3-phenylpropionate with commercially available ethyl acetoacetate in step one and by replacing 1-phenylpiperazine with commercially available 3-trifluoromethylbenzylamine in step 3. $^1$H NMR (400 MHz, $d_6$-DMSO): 11.74 (s, 1H), 9.02 (t, 1H), 8.38 (s, 1H), 7.57-7.69 (m, 4H), 5.76 (s, 1H), 4.56 (d, 2H), 2.37 (s, 3H).

EXAMPLE 17

7-hydroxy-5-(1-methylethyl)-N-(phenylmethyl)pyrazolo[1,5-a]pyrimidine-3-carboxamide (Compound 21)

7-hydroxy-5-(1-methylethyl)-N-(phenylmethyl)pyrazolo[1,5-a]pyrimidine-3-carboxamide was prepared according to the method of example 1 by replacing ethyl 3-oxo-3-phenylpropionate with commercially available ethyl 5-methyl-3-oxohexanoate in step 1 and by replacing 1-phenylpiperazine with commercially available benzylamine in step 3. $^1$H NMR (400 MHz, $d_6$-DMSO): 11.40 (s, 1H), 8.95-8.90 (m, 1H), 8.38 (s, 1H), 7.34-7.30 (m, 4H), 7.27-7.21 (m, 1H), 5.77-5.76 (m, 1H), 4.49-4.46 (m, 2H), 3.27-3.18 (m, 1H), 1.22 (d, 6H).

EXAMPLE 18

7-hydroxy-N-(phenylmethyl)-5-pyridin-2-ylpyrazolo[1,5-a]pyrimidine-3-carboxamide (Compound 22)

7-hydroxy-N-(phenylmethyl)-5-pyridin-2-ylpyrazolo[1,5-a]pyrimidine-3-carboxamide was prepared according to the method of Example 1 by replacing ethyl 3-oxo-3-phenylpropionate with commercially available ethyl picolinoylacetate in step 1, and by replacing 1-phenylpiperazine with commercially available benzylamine in step 3.

$^1$N NMR (400 MHz, $d_6$-DMSO): 11.74 (s, 1H), 9.10-9.04 (m, 1H), 8.83-8.80 (m, 1H), 8.47-8.41 (m, 2H), 8.10-8.04 (m, 1H), 7.67-7.62 (m, 1H), 7.36-7.30 (m, 4H), 7.28-7.21 (m, 1H), 6.94 (s, 1H), 4.52-4.48 (m, 2H).

EXAMPLE 19

N-cyclohexyl-7-hydroxy-5-methylpyrazolo[1,5-a]pyrimidine-3-carboxamide (Compound 23)

N-cyclohexyl-7-hydroxy-5-methylpyrazolo[1,5-a]pyrimidine-3-carboxamide was prepared according to the method of Example 1 by replacing ethyl 3-oxo-3-phenylpropionate with commercially available ethyl acetoacetate in step 1, and by replacing 1-phenylpiperazine with commercially available cyclohexylamine in step 3.

$^1$H NMR (400 MHz, $d_6$-DMSO): 8.72 (d, 1H), 7.85 (s, 1H), 5.39 (s, 1H), 3.77-3.84 (m, 1H), 2.93-2.99 (m, 1H), 2.20 (s, 3H), 1.52-1.88 (m, 4H), 1.06-1.42 (m, 5H).

EXAMPLE 20

7-hydroxy-5,6-dimethyl-N-(phenylmethyl)pyrazolo[1,5-a]pyrimidine-3-carboxamide (Compound 24)

7-hydroxy-5,6-dimethyl-N-(phenylmethyl)pyrazolo[1,5-a]pyrimidine-3-carboxamide was prepared according to the method of Example 1 by replacing ethyl 3-oxo-3-phenylpropionate with commercially available ethyl 2-methylacetoacetate in step 1 and by replacing 1-phenylpiperazine with commercially available benzylamine in step 3.

$^1$H NMR (400 MHz, $d_6$-DMSO): 11.45 (s, 1H), 8.93-8.86 (m, 1H), 8.39 (s, 1H), 7.37-7.31 (m, 4H), 7.29-7.22 (m, 1H), 4.51-4.46 (m, 2H), 2.43 (s, 3H), 1.98 (s, 3H).

EXAMPLE 21

5-furan-3-yl-7-hydroxy-N-(phenylmethyl)pyrazolo[1,5-a]pyrimidine-3-carboxamide (Compound 25)

5-furan-3-yl-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-oxo-3-(furan-3-yl)propanoate in step 1, and by replacing 1-phenylpiperazine with commercially available benzylamine in step 3. $^1$H NMR (400 MHz, d$_6$-DMSO): 11.08 (s, 1H), 9.07-9.01 (m, 1H), 8.64-8.61 (br. s, 1H), 8.44 (s, 1H), 7.91-7.88 (m, 1H), 7.38-7.32 (m, 4H), 7.30-7.23 (m, 1H), 7.15 (s; 1H), 6.33 (s, 1H), 4.55-4.48 (m, 2H).

EXAMPLE 22

Ethyl N-[(7-hydroxy-5-methylpyrazolo[1,5-a]pyrimidin-3-yl)carbonyl]phenylalaninate (Compound 26)

Ethyl N-[(7-hydroxy-5-methylpyrazolo[1,5-a]pyrimidin-3-yl)carbonyl]-L-phenylalaninate was prepared according to the method of Example 1 by replacing ethyl 3-oxo-3-phenylpropionate with commercially available ethyl acetoacetate in step 1, and by replacing 1-phenylpiperazine with commercially available L-phenylalanine ethyl ester in step 3. $^1$H NMR (400 MHz, d$_6$-DMSO): 11.72 (s, 1H), 8.78 (d, 1H), 8.43 (s, 1H), 7.29 (s, 4H), 7.21 (s, 1H), 5.75 (s, 1H), 4.62 (q, 1H), 4.05-4.10 (m, 2H), 3.06-3.17 (m, 2H), 2.35 (s, 3H), 1.11 (t, 3H).

EXAMPLE 23

Phenylmethyl 7-hydroxy-5-phenylpyrazolo[1,5-a]pyrimidine-3-carboxylate (Compound 27)

Phenylmethyl 7-hydroxy-5-phenylpyrazolo[1,5-a]pyrimidine-3-carboxylate was prepared according to the method of example 1 by replacing 1-phenylpiperazine with commercially available benzyl alcohol in step 3. $^1$H NMR (400 MHz, d$_6$-DMSO): 11.70 (broad s, 1H), 8.33 (s, 1H), 7.73 (d, 2H), 7.62-7.45 (m, 5H), 7.45-7.37 (m, 3H), 6.29 (s, 1H), 5.35 (s, 2H).

EXAMPLE 24

7-hydroxy-N-{[4-(methyloxy)phenyl]methyl}-5-phenylpyrazolo[1,5-a]pyrimidine-3-carboxamide (Compound 28)

7-hydroxy-N-{[4-(methyloxy)phenyl]methyl}-5-phenylpyrazolo[1,5-a]pyrimidine-3-carboxamide was prepared according to the method of example 1 by replacing 1-phenylpiperazine with commercially available 4-methoxybenzylamine in step 3. $^1$H NMR (400 MHz, d$_6$-DMSO): 11.33 (broad s, 1H), 8.98 (t, 1H), 8.43 (s, 1H), 7.83 (dd, 2H), 7.61 (t, 3H), 7.29 (d, 2H), 6.90 (dd, 2H), 6.29 (s, 1H), 4.44 (d, 2H), 3.72 (s, 3H).

EXAMPLE 25

N,N-diethyl-7-hydroxy-5-phenylpyrazolo[1,5-a]pyrimidine-3-carboxamide (Compound 29)

N,N-diethyl-7-hydroxy-5-phenylpyrazolo[1,5-a]pyrimidine-3-carboxamide was prepared according to the method of Example 1 by replacing of 1-phenylpiperazine with commercially available N,N-diethylamine in step 3.

EXAMPLE 26

N-cyclohexyl-7-hydroxy-5-phenylpyrazolo[1,5-a]pyrimidine-3-carboxamide (Compound 30)

N-cyclohexyl-7-hydroxy-5-phenylpyrazolo[1,5-a]pyrimidine-3-carboxamide was prepared according to the method of Example 1 by replacing 1-phenylpiperazine with commercially available cyclohexylamine in step 3.

EXAMPLE 27

N-[3-(dimethylamino)propyl]-7-hydroxy-5-phenylmazolo[1,5-a]pyrimidine-3-carboxamide (Compound 31)

N-[3-(dimethylamino)propyl]-7-hydroxy-5-phenylpyrazolo[1,5-a]pyrimidine-3-carboxamide was prepared according to the method of Example 1 by replacing of 1-phenylpiperazine with commercially available 3-(dimethylamino)propylamine in step 3.
$^1$H NMR (400 MHz, d$_6$-DMSO): 11.25 (broad s, 1H), 8.62 (m, 1H), 8.34 (m, 1H), 7.80 (m, 2H), 7.59 (m, 3H), 6.29 (m, 1H), 3.35 (m, 2H), 3.11 (t, 2H), 2.78 (s, 6H), 1.86 (m, 2H).

EXAMPLE 28

N-ethyl-7-hydroxy-5-phenylpyrazolo[1,5-a]pyrimidine-3-carboxamide (Compound 32)

N-ethyl-7-hydroxy-5-phenylpyrazolo[1,5-a]pyrimidine-3-carboxamide was prepared according to the method of Example 1 by replacing 1-phenylpiperazine with commercially available ethylamine in step 3. $^1$H NMR (400 MHz, d$_6$-DMSO): 11.26 (broad s, 1H), 8.75 (d, 1H), 8.53 (d, 1H), 8.36 (s, 1H), 7.80 (d, 2H), 7.59 (m, 3H), 6.27 (s, 1H), 3.28 (m, 2H), 1.15 (t, 3H).

EXAMPLE 29

N-cyclopentyl-7-hydroxy-5-phenylpyrazolo[1,5-a]pyrimidine-3-carboxamide (Compound 34)

N-cyclopentyl-7-hydroxy-5-phenylpyrazolo[1,5-a]pyrimidine-3-carboxamide was prepared according to the method of Example 1 by replacing 1-phenylpiperazine with commercially available cyclopentylamine in step 3. $^1$H NMR (400 MHz, d$_6$-DMSO): 11.25 (broad s, 1H), 8.43 (s, 1H), 8.29 (d, 1H), 7.82 (dd, 2H), 7.59 (m, 3H), 6.28 (s, 1H), 4.24 (m, 1H), 1.93 (m, 2H), 1.73 (m, 2H), 1.56 (m, 4H).

EXAMPLE 30

7-hydroxy-N-{[2-(methyloxy)phenyl]methyl}-5-phenylpyrazolo[1,5-a]pyrimidine-3-carboxamide (Compound 35)

7-hydroxy-N-{[2-(methyloxy)phenyl]methyl}-5-phenylpyrazolo[1,5-a]pyrimidine-3-carboxamide was prepared according to the method of Example 1 by replacing 1-phenylpiperazine with commercially available 2-methoxybenzylamine in step 3. $^1$H NMR (400 MHz, d$_6$-DMSO): 11.32 (s, 1H), 8.89 (s, 1H), 8.51 (s, 1H), 7.82 (d, 2H), 7.60 (s, 3H), 7.25 (s, 2H), 7.01 (d, 1H), 6.92 (t, 1H), 6.30 (s, 1H), 4.48 (d, 2H), 3.84 (s, 3H).

EXAMPLE 31

7-hydroxy-N-[3-methylphenyl)methyl]-5-phenylpyrazolo[1,5-a]pyrimidine-3-carboxamide (Compound 36)

7-hydroxy-N-[(3-methylphenyl)methyl]-5-phenylpyrazolo[1,5-a]pyrimidine-3-carboxamide was prepared according to the method of Example 1 by replacing 1-phenylpiperazine with commercially available 3-methylbenzylamine in step 3. $^1$H NMR (400 MHz, $d_6$-DMSO): 11.33 (s, 1H), 9.02 (t, 1H), 8.46 (s, 1H), 7.83 (dd, 2H), 7.58-7.62 (m, 3H), 7.23 (t, 1H), 7.15 (d, 2H), 7.07 (d, 1H), 6.30 (s, 1H), 4.47 (d, 2H), 2.29 (s, 3H).

EXAMPLE 32

7-hydroxy-N-[(4-methylphenyl)methyl]-5-phenylpyrazolo[1,5-a]pyrimidine-3-carboxamide (Compound 37)

7-hydroxy-N-[(4-methylphenyl)methyl]-5-phenylpyrazolo[1,5-a]pyrimidine-3-carboxamide was prepared according to the method of Example 1 by replacing 1-phenylpiperazine with commercially available 4-methylbenzylamine in step 3.
$^1$H NMR (400 MHz, $d_6$-DMSO): 11.32 (s, 1H), 9.00 (t, 1H), 8.46 (s, 1H), 7.83 (d, 2H), 7.60 (d, 3H), 7.24 (d, 2H), 7.15 (d, 2H), 6.30 (s, 1H), 4.46 (d, 2H), 2.28 (s, 3H).

EXAMPLE 33

7-hydroxy-N-[(2-methylphenyl)methyl]-5-phenylpyrazolo[1,5-a]pyrimidine-3-carboxamide (Compound 38)

7-hydroxy-N-[(2-methylphenyl)methyl]-5-phenylpyrazolo[1,5-a]pyrimidine-3-carboxamide was prepared according to the method of Example 1 by replacing 1-phenylpiperazine with commercially available 2-methylbenzylamine in step 3. $^1$H NMR (400 MHz, $d_6$-DMSO): 11.31 (s, 1H), 8.91 (t, 1H), 8.50 (s, 1H), 7.82 (d, 2H), 7.60 (d, 3H), 7.30 (s, 1H), 7.19 (s, 3H), 6.30 (s, 1H), 4.49 (d, 2H), 2.34 (s, 3H).

EXAMPLE 34

N-[(2-bromophenyl)methyl]-7-hydroxy-5-phenylpyrazolo[1,5-a]pyrimidine-3-carboxamide (Compound 39)

N-[(2-bromophenyl)methyl]-7-hydroxy-5-phenylpyrazolo[1,5-a]pyrimidine-3-carboxamide was prepared according to the method of Example 1 by replacing 1-phenylpiperazine with commercially available 2-bromobenzylamine in step 3. $^1$H NMR (400 MHz, $d_6$-DMSO): 11.35 (s, 1H), 9.09 (t, 1H), 8.51 (s, 1H), 7.82 (d, 2H), 7.65 (d, 1H), 7.58-7.61 (m, 3H), 7.37-7.43 (m, 2H), 6.30 (s, 1H), 4.55 (d, 2H).

EXAMPLE 35

N-[(3-bromophenyl)methyl]-7-hydroxy-5-phenylpyrazolo[1,5-a]pyrimidine-3-carboxamide (Compound 40)

N-[(3-bromophenyl)methyl]-7-hydroxy-5-phenylpyrazolo[1,5-a]pyrimidine-3-carboxamide was prepared according to the method of Example 1 by replacing 1-phenylpiperazine with commercially available 3-bromobenzylamine in step 3. $^1$H NMR (400 MHz, $d_6$-DMSO): 11.35 (s, 1H), 9.08 (t, 1H), 8.45 (s, 1H), 7.81-7.83 (m, 2H), 7.59-7.61 (m, 3H), 7.55 (s, 1H), 7.47 (d, 1H), 7.30-7.38 (m, 2H), 6.29 (s, 1H), 4.51 (d, 2H)

EXAMPLE 36

N-[(4-bromophenyl)methyl]-7-hydroxy-5-phenylpyrazolo[1,5-a]pyrimidine-3-carboxamide (Compound 41)

bromophenyl)methyl]-7-hydroxy-5-phenylpyrazolo[1,5-a]pyrimidine-3-carboxamide was prepared according to the method of Example 1 by replacing 1-phenylpiperazine with commercially available 4-bromobenzylamine in step 3. $^1$H NMR (400 MHz, $d_6$-DMSO): 11.33 (s, 1H), 9.08 (t, 1H), 8.44 (s, HD, 7.82 (dd, 2H), 7.54-7.62 (m, 5H), 7.32 (d, 2H), 6.30 (s, 1H), 4.47 (d, 2H).

EXAMPLE 37

5-(4-fluorophenyl)-7-hydroxy-N-(phenylmethyl)pyrazolo[1,5-a]pyrimidine-3-carboxamide (Compound 42)

luorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 4-fluorobenzoylacetate in step 1, and replacing 1-phenylpiperazine with commercially available benzylamine in step 3.
$^1$H NMR (400 MHz, $d_6$-DMSO): 11.42 (s, 1H), 9.07-9.01 (m, 1H), 8.46 (s, 1H), 7.99-7.84 (m, 2H), 7.47-7.22 (m, 7H), 6.27 (s, 1H), 4.54-4.47 (m, 2H).

EXAMPLE 38

5-(2-fluorophenyl)-7-hydroxy-N-(phenylmethyl)pyrazolo[1,5-a]pyrimidine-3-carboxamide (Compound 43)

5-(2-fluorophenyl)-7-hydroxy-N-(phenylmethyl)pyrazolo[1,5-a]pyrimidine-3-carboxamide was prepared according to the method of Example 1 by replacing ethyl 3-oxo-3-phenyl-propionate with commercially available ethyl 2-fluorobenzoylacetate in step 11, and replacing 1-phenylpiperazine with commercially available benzylamine in step 3.
$^1$H NMR (400 MHz, $d_6$-DMSO): 11.94 (s, 1H), 9.04-8.98 (m, 1H), 8.48 (s, 1H), 7.80-7.58 (m, 2H), 7.46-7.30 (m, 6H), 7.29-7.22 (m, 1H), 6.16 (s, 1H), 4.53-4.46 (m, 2H).

EXAMPLE 39

7-hydroxy-N-(2-morpholin-4-ylethyl)-5-phenylpyrazolo[1,5-a]pyrimidine-3-carboxamide (Compound 44)

7-hydroxy-N-(2-morpholin-4-ylethyl)-5-phenylpyrazolo[1,5-a]pyrimidine-3-carboxamide was prepared according to the method of Example 1 by replacing 1-phenylpiperazine with commercially available 2-morpholin-4-ylethylamine in step 3.
$^1$H NMR (400 MHz, $d_6$-DMSO): 8.73 (t, 1H), 8.32 (broad s, 1H), 7.79 (d, 2H), 7.59 (m, 3H), 6.27 (s, 1H), 3.98-3.53 (m, 8H), 3.33 (t, 2H), 3.17 (m, 2H).

EXAMPLE 40

3-[(4-methylpiperazin-1-yl)carbonyl]-5-phenylpyrazolo[1,5-a]pyrimidin-7-ol (Compound 45)

3-[(4-methylpiperazin-1-yl)carbonyl]-5-phenylpyrazolo[1,5-a]pyrimidin-7-ol was prepared according to the method of Example 1 by replacing 1-phenylpiperazine with commercially available 4-methylpiperazine in step 3. $^1$H NMR (400 MHz, $d_6$-DMSO): 7.97 (m, 3H), 7.48 (m, 3H), 6.09 (s, 1H), 3.35 (s, 3H), 3.09 (m, 7H), 2.69 (m, 2H), 2.50 (m, 2H).

EXAMPLE 41

7-hydroxy-N-methyl-5-phenylpyrazolo[1,5-a]pyrimidine-3-carboxamide (Compound 46)

7-hydroxy-N-methyl-5-phenylpyrazolo[1,5-a]pyrimidine-3-carboxamide was prepared according to the method of Example 1 by replacing 1-phenylpiperazine with commercially available methylamine in step 3. $^1$H NMR (400 MHz, $d_6$-DMSO): 11.32 (broad s, 1H), 8.46 (m, 1H), 8.35, (s, 1H), 7.84 (dd, 2H), 7.61 (m, 3H), 6.29 (s, 1H), 2.81 (d, 3H).

EXAMPLE 42

5-phenyl-3-(piperidin-1-ylcarbonyl)pyrazolo[1,5-a]pyrimidin-7-ol (Compound 47)

5-phenyl-3-(piperidin-1-ylcarbonyl)pyrazolo[1,5-a]pyrimidin-7-ol was prepared according to the method of Example 1 by replacing 1-phenylpiperazine with commercially available piperidine in step 3. $^1$H NMR (400 MHz, $d_6$-DMSO): 12.05 (broad s, 1H), 8.15 (s, 1H), 7.81 (dd, 2H), 7.61 (m, 3H), 6.21 (s, 1H), 3.61 (m, 4H), 1.64 (m, 6H).

EXAMPLE 43

3-(3,4-dihydroisoquinolin-2(1H)-ylcarbonyl)-5-phenylpyrazolo[1,5-a]pyrimidin-7-ol (Compound 48)

3-(3,4-dihydroisoquinolin-2(1H)-ylcarbonyl)-5-phenylpyrazolo[1,5-a]pyrimidin-7-ol was prepared according to the method of Example 1 by replacing 1-phenylpiperazine with commercially available 1,2,3,4-tetrahydroisoquinoline in step 3. $^1$H NMR (400 MHz, $d_6$-DMSO): 12.00 (broad s, 1H), 8.33 (s, 1H), 7.81 (dd, 2H), 7.59 (m, 3H), 7.27 (m, 1H), 7.21 (m, 3H), 6.26 (s, 1H), 4.86 (m, 2H), 3.89 (t, 2H), 2.93 (t, 2H).

EXAMPLE 44

7-hydroxy-N-(3-morpholin-4-ylpropyl)-5-phenylpyrazolo[1,5-a]pyrimidine-3-carboxamide (Compound 49)

7-hydroxy-N-(3-morpholin-4-ylpropyl)-5-phenylpyrazolo[1,5-a]pyrimidine-3-carboxamide was prepared according to the method of Example 1 by replacing 1-phenylpiperazine with commercially available 3-morpholin-4-ylpropylamine in step 3.
$^1$H NMR (400 MHz, $d_6$-DMSO): 11.15 (broad s, 1H), 8.74 (dd, 1H), 8.63 (m, 1H), 8.51 (d, 1H), 8.34 (s, 1H), 7.80 (m, 2H), 7.58 (m, 2H), 6.29 (s, 1H), 3.96 (m, 2H), 3.45 (m, 6H), 3.16 (m, 2H), 3.07 (m, 2H), 1.90 (m, 2H).

EXAMPLE 45

7-hydroxy-N-methyl-N-(1-methylpiperidin-4-yl)-5-phenylpyrazolo[1,5-a]pyrimidine-3-carboxamide (Compound 50)

7-hydroxy-N-methyl-N-(1-methylpiperidin-4-yl)-5-phenylpyrazolo[1,5-a]pyrimidine-3-carboxamide was prepared according to the method of Example 1 by replacing 1-phenylpiperazine with commercially available N,1-dimethylpiperidin-4-amine in step 3. $^1$H NMR. (400 MHz, $d_6$-DMSO): 9.61 (broad s, 1H), 8.24 (broad s, 1H), 7.79 (dd, 2H), 7.60 (m, 3H), 6.28 (s, 1H), 3.50 (m, 2H), 3.18-3.06 (m, 6H), 2.77 (s, 3H), 2.06 (m, 2H), 2.01 (m, 2H).

EXAMPLE 46

N-cyclopropyl-7-hydroxy-5-phenylpyrazolo[1,5-a]pyrimidine-3-carboxamide (Compound 51)

N-cyclopropyl-7-hydroxy-5-phenylpyrazolo[1,5-a]pyrimidine-3-carboxamide was prepared according to the method of Example 1 by replacing 1-phenylpiperazine with commercially available cyclopropylamine in step 3. $^1$H NMR (400 MHz, $d_6$-DMSO): 11.29 (broad s, 1H), 8.48 (d, 1H), 8.32 (s, 1H), 7.82 (dd, 2H), 7.59 (m, 3H), 6.27 (s, 1H), 2.81 (m, 1H), 0.73 (m, 2H), 0.57 (m, 2H).

EXAMPLE 47

7-hydroxy-N-[(3-endo)-8-methyl-8-azabicyclo[3.2.1]oct-3-yl]-5-phenylpyrazolo[1,5-a]pyrimidine-3-carboxamide (Compound 52)

7-hydroxy-N-[(3-endo)-8-methyl-8-azabicyclo[3.2.1]oct-3-yl]-5-phenylpyrazolo[1,5-a]pyrimidine-3-carboxamide was prepared according to the method of Example 1 by replacing 1-phenylpiperazine with commercially available [(3-endo)-8-methyl-8-azabicyclo[3.2.1]oct-3-yl]amine in step 3. $^1$H NMR (400 MHz, $d_6$-DMSO): 9.20 (broad s, 1H), 9.03 (d, 1H), 7.95 (s, 1H), 7.86 (dd, 2H), 7.43 (m, 3H), 5.97 (s, 1H), 4.17 (m, 1H), 3.86 (broad s, 2H), 2.66 (s, 3H), 2.37 (m, 2H), 2.29 (m, 2H), 2.12 (m, 4H).

EXAMPLE 48

5-[2-bromo-5-(methyloxy)phenyl]-7-hydroxy-N-(phenylmethyl)pyrazolo[1,5-a]pyrimidine-3-carboxamide (Compound 53)

5-[2-bromo-5-(methyloxy)phenyl]-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 2-bromo-5-methoxybenzoylacetate in step 1, and replacing 1-phenylpiperazine with commercially available benzylamine in step 3.

EXAMPLE 49

7-hydroxy-5-phenyl-N-{[4-(phenyloxy)phenyl]methyl}pyrazolo[1,5-a]pyrimidine-3-carboxamide (Compound 54)

7-hydroxy-5-phenyl-N-{[4-(phenyloxy)phenyl]methyl}pyrazolo[1,5-a]pyrimidine-3-carboxamide was prepared according to the method of Example 1 by replacing 1-phenylpiperazine with commercially available 4-phenoxybenzylamine in step 3. $^1$H NMR (400 MHz, d$_6$-DMSO): 11.30 (s, 1H), 9.02 (t, 1H), 8.43 (s, 1H), 7.81 (dd, 2H), 7.58 (d, 3H), 7.33-7.38 (m, 4H), 7.10 (tt, 1H), 6.95-7.00 (m, 4H), 6.28 (s, 1H), 4.48 (d, 2H).

EXAMPLE 50

5-(3-bromophenyl)-7-hydroxy-N-(phenylmethyl) pyrazolo[1,5-a]pyrimidine-3-carboxamide (Compound 55)

5-(3-bromophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-bromobenzoylacetate in step 1 and replacing 1-phenylpiperazine with commercially available benzylamine in step 3.

EXAMPLE 51

7-hydroxy-N-(phenylmethyl)-5-pyridin-4-ylpyrazolo [1,5-a]pyrimidine-3-carboxamide (Compound 56)

7-hydroxy-N-(phenylmethyl)-5-pyridin-4-ylpyrazolo[1,5-a]pyrimidine-3-carboxamide was prepared according to the method of Example 1 by replacing ethyl 3-oxo-3-phenylpropionate with commercially available ethyl isonicotinoylacetate in step 1, and replacing 1-phenylpiperazine with commercially available benzylamine in step 3.

$^1$H NMR (400 MHz, d$_6$-DMSO): 9.05-8.97 (m, 1H), 8.82-8.76 (m, 2H), 8.46-8.37 (br. s, 1H), 7.99-7.83 (m, 2H), 7.40-7.32 (m, 4H), 7.30-7.24 (m, 1H), 6.42 (s, 1H), 4.56-4.49 (m, 2H).

EXAMPLE 52

5-(3-chlorophenyl)-7-hydroxy-N-phenylmethyl) pyrazolo[1,5-a]pyrimidine-3-carboxamide (Compound 57)

5-(3-chlorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-chlorobenzoylacetate in step 1, and replacing 1-phenylpiperazine with commercially available benzylamine in step 3. $^1$H NMR (400 MHz, d$_6$-DMSO): 11.63-11.56 (br. s, 1H), 9.06-9.00 (m, 1H), 8.49-8.45 (br. s, 1H), 7.89-7.86 (m, 1H), 7.78-7.73 (m, 1H), 7.70-7.55 (m, 2H), 7.38-7.31 (m, 4H), 7.29-7.23 (m, 1H), 6.30 (s, 1H), 4.55-4.48 (m, 2H).

EXAMPLE 53

5-(4-chlorophenyl)-7-hydroxy-N-(phenylmethyl) pyrazolo[1,5-a]pyrimidine-3-carboxamide (Compound 58)

5-(4-chlorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 4-chlorobenzoylacetate in step 1, and replacing 1-phenylpiperazine with commercially available benzylamine in step 3. $^1$H NMR (400 MHz, d$_6$-DMSO): 11.52-11.45 (br. s, 1H), 9.07-9.01 (m, 1H), 8.48-8.44 (br. s, 1H), 7.87-7.80 (m, 2H), 7.68-7.61 (m, 2H), 7.38-7.31 (m, 4H), 7.29-7.23 (m, 1H), 6.29 (s, 1H), 4.53-4.48 (m, 2H).

EXAMPLE 54

7-hydroxy-5-phenyl-N-(2-phenylethyl)pyrazolo[1,5-a]pyrimidine-3-carboxamide (Compound 59)

7-hydroxy-5-phenyl-N-(2-phenylethyl)pyrazolo[1,5-a] pyrimidine-3-carboxamide was prepared according to the method of Example 1 by replacing 1-phenylpiperazine with commercially available phenethylamine in step 3. $^1$H NMR (400 MHz, d$_6$-DMSO): 11.32 (broad s, 1H), 8.62 (t, 1H), 8.39 (s, 1H), 7.83 (dd, 2H), 7.61 (m, 3H), 7.27 (m, 5H), 6.29 (s, 1H), 3.49 (m, 2H), 2.88 (t, 2H).

EXAMPLE 55

Ethyl N-[(7-hydroxy-5-phenylpyrazolo[1,5-a]pyrimidin-3-yl)carbonyl]-L-phenylalaninate (Compound 60)

Ethyl N-[(7-hydroxy-5-phenylpyrazolo[1,5-a]pyrimidin-3-yl)carbonyl]-L-phenylalaninate was prepared according to the method of Example 1 by replacing 1-phenylpiperazine with commercially available L-phenylalanine ethyl ester in step 3.

$^1$H NMR (400 MHz, d$_6$-DMSO): 11.29 (broad s, 1H), 8.91 (d, 1H), 8.51 (s, 1H), 7.78 (d, 2H), 7.58 (m, 3H), 7.31 (m, 5H), 6.27 (s, 1H), 4.69 (m, 1H), 4.10 (q, 2H), 3.46 (m, 3H), 3.13 (m, 2H), 1.11 (t, 3H).

EXAMPLE 56

7-hydroxy-N,5-diphenylpyrazolo[1,5-a]pyrimidine-3-carboxamide (Compound 61)

7-hydroxy-N,5-diphenylpyrazolo[1,5-a]pyrimidine-3-carboxamide was prepared according to the method of Example 1 by replacing 1-phenylpiperazine with commercially available aniline in step 3. $^1$H NMR (400 MHz, d$_6$-DMSO): 11.50 (broad s, 1H), 10.19 (broad s, 1H), 8.62 (broad s, 1H), 7.86 (m, 2H), 7.77 (d, 2H), 7.62 (m, 3H), 7.27 (m, 2H), 7.11 (t, 1H), 6.32 (s, 1H).

EXAMPLE 57

N-(cyclopropylmethyl)-7-hydroxy-5-phenylpyrazolo [1,5-a]pyrimidine-3-carboxamide (Compound 62)

N-(cyclopropylmethyl)-7-hydroxy-5-phenylpyrazolo[1,5-a]pyrimidine-3-carboxamide was prepared according to the method of Example 1 by replacing 1-phenylpiperazine with commercially available cyclopropylmethylamine in step 3.

$^1$H NMR (400 MHz, d$_6$-DMSO): 11.29 (broad s, 1H), 8.60 (t, 1H), 8.44 (s, 1H), 7.82 (m, 2H), 7.59 (t, 3H), 6.30 (s, 1H), 3.17 (t, 2H), 1.02 (m, 1H), 0.47 (m, 2H), 0.25 (m, 2H).

EXAMPLE 58

N-(1,1-dimethylethyl)-7-hydroxy-5-phenylpyrazolo [1,5-a]pyrimidine-3-carboxamide (Compound 63)

N-(1,1-dimethylethyl)-7-hydroxy-5-phenylpyrazolo[1,5-a]pyrimidine-3-carboxamide was prepared according to the method of Example 1 by replacing 1-phenylpiperazine with commercially available 1,1-dimethylethylamine in step 3.

$^1$H NMR (400 MHz, $d_6$-DMSO): 11.21 (broad s, 1H), 8.50 (s, 1H), 7.79 (m, 2H), 7.57 (m, 3H), 6.26 (s, 1H), 1.41 (s, 9H).

EXAMPLE 59

7-hydroxy-N-(2-methylpropyl)-5-phenylpyrazolo[1,5-a]pyrimidine-3-carboxamide (Compound 64)

7-hydroxy-N-(2-methylpropyl)-5-phenylpyrazolo[1,5-a]pyrimidine-3-carboxamide was prepared according to the method of Example 1 by replacing 1-phenylpiperazine with commercially available 2-methylpropylamine in step 3. $^1$H NMR (400 MHz, $d_6$-DMSO): 11.24 (broad s, 1H), 8.47 (m, 1H), 8.42 (s, 1H), 7.79 (dd, 2H), 7.59 (m, 3H), 6.28 (s, 1H), 3.10 (t, 2H), 1.83 (m, 1H), 0.92 (d, 6H).

EXAMPLE 60

7-hydroxy-N-(3-methylbutyl)-5-phenylpyrazolo[1,5-a]pyrimidine-3-carboxamide (Compound 65)

7-hydroxy-N-(3-methylbutyl)-5-phenylpyrazolo[1,5-a]pyrimidine-3-carboxamide was prepared according to the method of Example 1 by replacing 1-phenylpiperazine with commercially available 3-methylbutylamine in step 3. $^1$H NMR (400 MHz, $d_6$-DMSO): 11.24 (broad s, 1H), 8.42 (m, 1H), 8.37 (s, 1H), 7.79 (dd, 2H), 7.59 (m, 3H), 6.27 (s, 1H), 3.30 (m, 2H), 1.64 (m, 1H), 1.42 (m, 2H), 0.92 (d, 6H).

EXAMPLE 61

N-(2,2-dimethylpropyl)-7-hydroxy-5-phenylpyrazolo[1,5-a]pyrimidine-3-carboxamide (Compound 66)

N-(2,2-dimethylpropyl)-7-hydroxy-5-phenylpyrazolo[1,5-a]pyrimidine-3-carboxamide was prepared according to the method of Example 1 by replacing 1-phenylpiperazine with commercially available 2,2-dimethylpropylamine in step 3. $^1$H NMR (400 MHz, $d_6$-DMSO): 11.22 (broad s, 1H), 8.50 (s, 1H), 8.33 (m, 1H), 7.79 (m, 2H), 7.57 (m, 3H), 6.28 (s, 1H), 3.12 (d, 2H), 0.92 (s, 9H).

EXAMPLE 62

7-hydroxy-5-phenyl-N-(2-piperidin-1-ylethyl)pyrazolo[1,5-a]pyrimidine-3-carboxamide (Compound 67)

7-hydroxy-5-phenyl-N-(2-piperidin-1-ylethyl)pyrazolo[1,5-a]pyrimidine-3-carboxamide was prepared according to the method of Example 1 by replacing 1-phenylpiperazine with commercially available 2-piperidin-1-ylethylamine in step 3.

$^1$H NMR (400 MHz, $d_6$-DMSO): 11.32 (broad s, 1H), 9.25 (broad s, 1H), 8.74 (m, 1H), 8.36 (s, 1H), 7.81 (m, 2H), 7.62 (m, 3H), 6.31 (s, 1H), 3.64 (m, 2H), 3.55 (d, 2H), 3.25 (m, 2H), 2.94 (m, 2H), 1.85-1.37 (m, 6H).

EXAMPLE 63

7-hydroxy-5-phenyl-N-piperidin-4-ylpyrazolo[1,5-a]pyrimidine-3-carboxamide Compound 68)

7-hydroxy-5-phenyl-N-piperidin-4-ylpyrazolo[1,5-a]pyrimidine-3-carboxamide was prepared according to the method of Example 1 by replacing 1-phenylpiperazine with commercially available 1-N-Boc-4-aminopiperidine in step 3 followed by Boc-deprotection using standard conditions. $^1$H NMR (400 MHz, $d_6$-DMSO): 11.23 (broad s, 1H), 8.87 (broad s, 2H), 8.58 (d, 1H), 8.56 (s, 1H), 7.79 (dd, 2H), 7.58 (m, 3H), 6.29 (s, 1H), 4.04 (m, 1H), 3.34 (d, 2H), 2.99 (m, 2H), 2.00 (m, 2H), 1.79 (m, 2H).

EXAMPLE 64

7-hydroxy-5-phenylpyrazolo[1,5-a]pyrimidine-3-carboxamide (Compound 69)

7-hydroxy-5-phenylpyrazolo[1,5-a]pyrimidine-3-carboxamide was prepared according to the method of Example 1 by replacing 1-phenylpiperazine with commercially available ammonia in step 3. $^1$H NMR (400 MHz, $d_6$-DMSO): 11.25 (broad s, 1H), 8.38 (s, 1H), 7.97 (broad s, 1H), 7.81 (dd, 2H), 7.63 (m, 3H), 7.46 (broad s, 1H), 6.29 (s, 1H).

EXAMPLE 65

7-hydroxy-N-(1-methylethyl)-5-phenylpyrazolo[1,5-a]pyrimidine-3-carboxamide (Compound 70)

7-hydroxy-N-(1-methylethyl)-5-phenylpyrazolo[1,5-a]pyrimidine-3-carboxamide was prepared according to the method of Example 1 by replacing 1-phenylpiperazine with commercially available isopropylamine in step 3. $^1$H NMR (400 MHz, $d_6$-DMSO): 11.27 (broad s, 1H), 8.44 (s, 1H), 8.28 (d, 1H), 7.84 (dd, 2H), 7.60 (m, 3H), 6.29 (s, 1H), 4.13 (m, 1H), 1.20 (d, 6H).

EXAMPLE 66

3-(morpholin-4-ylcarbonyl)-5-phenylpyrazolo[1,5-a]pyrimidin-7-ol (Compound 71)

3-(morpholin-4-ylcarbonyl)-5-phenylpyrazolo[1,5-a]pyrimidin-7-ol was prepared according to the method of Example 1 by replacing 1-phenylpiperazine with commercially available morpholine in step 3. $^1$H NMR (400 MHz, $d_6$-DMSO): 12.11 (broad s, 1H), 8.19 (s, 1H), 7.81 (dd, 2H), 7.61 (m, 3H), 6.21 (s, 1H), 3.66 (m, 8H).

EXAMPLE 67

7-hydroxy-5-phenyl-N-[(1S,2R)-2-phenylcyclopropyl]pyrazolo[1,5-a]pyrimidine-3-carboxamide (Compound 72)

7-hydroxy-5-phenyl-N-[(1S,2R)-2-phenylcyclopropyl]pyrazolo[1,5-a]pyrimidine-3-carboxamide was prepared according to the method of Example 1 by replacing 1-phenylpiperazine with commercially available (1S,2R)-2-phenylcyclopropylamine in step 3.

$^1$H NMR (400 MHz, $d_6$-DMSO): 11.32 (broad s, 1H), 8.75 m, 1H), 8.39 (s, 1H), 7.81 (d, 2H), 7.59 (m, 3H), 7.27 (m, 2H), 7.17 (m, 3H), 6.29 (s, 1H), 3.02 (m, 1H), 2.09 (m, 1H), 1.36 (m, 1H), 1.33 (m, 1H).

EXAMPLE 68

7-hydroxy-5-[4-(methyloxy)phenyl]-N-(phenylmethyl)pyrazolo[1,5-a]pyrimidine-3-carboxamide (Compound 73)

7-hydroxy-5-[4-(methyloxy)phenyl]-N-(phenylmethyl)pyrazolo[1,5-a]pyrimidine-3-carboxamide was prepared according to the method of Example 1 by replacing ethyl 3-oxo-3-phenylpropionate with commercially available ethyl 4-methoxybenzoylacetate in step 1 and replacing 1-phenylpiperazine with commercially available benzylamine in step 3. $^1$H NMR (400 MHz, d$_6$-DMSO): 11.20-11.16 (br. s, 1H), 9.08-9.02 (m, 1H), 8.43 (s, 1H), 7.83-7.76 (m, 2H), 7.38-7.31 (m, 4H), 7.29-7.23 (m, 1H), 7.18-7.10 (m, 2H), 6.26 (s, 1H), 4.55-4.46 (m, 2H), 3.85 (m, 3H).

EXAMPLE 69

5-(3-fluorophenyl)-7-hydroxy-N-(phenylmethyl) pyrazolo[1,5-a]pyrimidine-3-carboxamide (Compound 74)

5-(3-fluorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-fluorobenzoylacetate in step 1, and replacing 1-phenylpiperazine with commercially available benzylamine in step 3. $^1$H NMR (400 MHz, d$_6$-DMSO): 11.54-11.43 (br. s, 1H), 9.07-9.01 (m, 1H), 8.47 (s, 1H), 7.74-7.58 (m, 3H), 7.50-7.41 (m, 1H), 7.38-7.31 (m, 4H), 7.29-7.23 (m, 1H), 6.33 (s, 1H), 4.55-4.47 (m, 2H).

EXAMPLE 70

7-hydroxy-5-phenyl-N-(1-phenylethyl)pyrazolo[1,5-a]pyrimidine-3-carboxamide (Compound 75)

7-hydroxy-5-phenyl-N-(1-phenylethyl)pyrazolo[1,5-a]pyrimidine-3-carboxamide was prepared according to the method of Example 1 by replacing 1-phenylpiperazine with commercially available 1-phenylethylamine in step 3.
$^1$H NMR (400 MHz, d$_6$-DMSO): 11.23 (s, 1H), 8.83 (d, 1H), 8.54 (s, 1H), 7.78 (d, 2H), 7.50-7.58 (m, 3H), 7.38 (d, 2H), 7.32 (t, 2H), 7.21 (t, 1H), 6.27 (s, 1H), 5.14-5.21 (m, 1H), 1.50 (d, 3H).

EXAMPLE 71

7-hydroxy-N-methyl-5-phenyl-N-(phenylmethyl) pyrazolo[1,5-a]pyrimidine-3-carboxamide (Compound 76)

7-hydroxy-N-methyl-5-phenyl-N-(phenylmethyl)pyrazolo[1,5-a]pyrimidine-3-carboxamide was prepared according to the method of Example 1 by replacing 1-phenylpiperazine with commercially available N-methylbenzylamine in step 3.
$^1$H NMR (400 MHz, d$_6$-DMSO): 11.81 (s, 1H), 8.34 (s, 1H), 7.81 (d, 2H), 7.54-7.61 (m, 3H), 7.27-7.35 (m, 4H), 6.30 (s, 1H), 4.73 (s, 2H), 2.50 (s, 3H).

EXAMPLE 72

1,1-dimethylethyl 4-({[(7-hydroxy-5-phenylpyrazolo [1,5-a]pyrimidin-3-yl)carbonyl]amino}methyl)piperidine-1-carboxylate (Compound 77)

1,1-dimethylethyl 4-({[(7-hydroxy-5-phenylpyrazolo[1,5-a]pyrimidin-3-yl)carbonyl]amino}methyl)piperidine-1-carboxylate was prepared according to the method of Example 1 by replacing 1-phenylpiperazine with commercially available 1-N-Boc-4-aminomethylpiperidine in step 3.
$^1$H NMR (400 MHz, CDCl$_3$): 10.66 (s, 1H), 8.20 (s, 1H), 7.69 (dd, 2H), 7.51-7.60 (m, 3H), 6.66 (s, 1H), 6.24 (s, 1H), 4.12 (s, 2H), 3.35 (s, 2H), 2.69 (s, 2H), 1.76 (d, 3H), 1.44 (s, 9H), 1.15-1.26 (m, 2H).

EXAMPLE 73

7-hydroxy-5-phenyl-N-(piperidin-4-ylmethyl)pyrazolo[1,5-a]pyrimidine-3-carboxamide (Compound 78)

7-hydroxy-5-phenyl-N-(piperidin-4-ylmethyl)pyrazolo[1,5-a]pyrimidine-3-carboxamide was prepared according to the method of Example 1 by replacing 1-phenylpiperazine with commercially available 1-N-Boc-4-aminomethylpiperidine in step 3 followed by Boc deprotection under standard conditions. $^1$H NMR (400 MHz, d$_6$-DMSO): 11.23 (s, 1H), 8.44 (s, 2H), 7.80 (d, 2H), 7.59 (d, 3H), 6.29 (s, 1H), 3.16-3.27 (m, 4H), 2.78-2.88 (m, 2H), 1.83 (d, 3H), 1.33-1.42 (m, 2H).

EXAMPLE 74

7-hydroxy-5-phenyl-N-(pyrrolidin-3-ylmethyl)pyrazolo[1,5-a]pyrimidine-3-carboxamide (Compound 79)

7-hydroxy-5-phenyl-N-(pyrrolidin-3-ylmethyl)pyrazolo[1,5-a]pyrimidine-3-carboxamide was prepared according to the method of Example 1 by replacing 1-phenylpiperazine with commercially available 1-N-Boc-3-aminomethylpyrrolidine in step 3 followed by Boc deprotection under standard conditions. $^1$H NMR (400 MHz, d$_6$-DMSO): 11.26 (s, 1H), 9.10 (broad s, 2H), 8.77 (t, 1H), 8.46 (s, 1H), 7.79-7.81 (m, 2H), 7.56-7.61 (m, 2H), 6.29 (s, 1H), 3.21-3.38 (m, 3H), 3.05-3.14 (m, 1H), 2.88-2.96 (m, 1H), 2.53-2.57 (m, 1H), 1.98-2.06 (m, 1H), 1.64-1.73 (m, 1H).

EXAMPLE 75

N-[(1-acetylpiperidin-4-yl)methyl]-7-hydroxy-5-phenylpyrazolo[1,5-a]pyrimidine-3-carboxamide (Compound 80)

N-[(1-acetylpiperidin-4-yl)methyl]-7-hydroxy-5-phenylpyrazolo[1,5-a]pyrimidine-3-carboxamide was prepared according to the method of Example 1 by replacing 1-phenylpiperazine with commercially available 1-acetylpiperidin-4-ylmethylamine in step 3.

EXAMPLE 76

3-{[4-(aminomethyl)piperidin-1-yl]carbonyl}-5-phenylpyrazolo[1,5-a]pyrimidin-7-ol (Compound 81)

3-{[4-(aminomethyl)piperidin-1-yl]carbonyl}-5-phenylpyrazolo[1,5-a]pyrimidin-7-ol was prepared according to the method of Example 1 by replacing 1-phenylpiperazine with commercially available 4-N-Boc-aminomethylpiperidine in step 3 followed by Boc deprotection under standard conditions. $^1$H NMR (400 MHz, d$_6$-DMSO): 8.77 (dd, 1H), 8.54 (dd, 1H), 8.03 (s, 2H), 7.81 (dd, 2H), 7.57-7.63 (m, 3H), 6.22 (s, 2H), 2.72-2.77 (m, 2H), 1.81-1.92 (m, 5H), 1.16-1.25 (m, 4H).

EXAMPLE 77

7-hydroxy-N-(phenylmethyl)-5-[3-(trifluoromethyl) phenyl]pyrazolo[1,5-a]pyrimidine-3-carboxamide (Compound 82)

7-hydroxy-N-(phenylmethyl)-5-[3-(trifluoromethyl)phenyl]pyrazolo[1,5-a]pyrimidine-3-carboxamide was prepared according to the method of Example 1 by replacing ethyl 3-oxo-3-phenylpropionate with commercially available ethyl 3-trifluoromethylbenzoylacetate in step 1, and replacing 1-phenylpiperazine with commercially available benzylamine in step 3. $^1$H NMR (400 MHz, $d_6$-DMSO): 11.84-11.77 (br. s, 1H), 9.05-8.99 (m, 1H), 8.48 (s, 1H), 8.13-8.05 (m, 2H), 7.99-7.92 (m, 1H), 7.83-7.76 (m, 1H), 7.38-7.31 (m, 4H), 7.29-7.23 (m, 1H), 6.34 (s, 1H), 4.54-4.47 (m, 2H).

EXAMPLE 78

7-hydroxy-5-(4-hydroxyphenyl)-N-(phenylmethyl) pyrazolo[1,5-a]pyrimidine-3-carboxamide (Compound 83)

7-hydroxy-5-(4-hydroxyphenyl)-N-(phenylmethyl)pyrazolo[1,5-a]pyrimidine-3-carboxamide was prepared according to the method of Example 1 by replacing ethyl 3-oxo-3-phenylpropionate with commercially available methyl 4-hydroxybenzoylacetate in step 1, and replacing 1-phenylpiperazine with commercially available benzylamine in step 3. $^1$H NMR (400 MHz, $d_6$-DMSO): 11.15-10.98 (br. s, 1H), 10.28 (s, 1H), 9.11-9.00 (m, 1H), 8.43 (s, 1H), 7.72-7.66 (m, 2H), 7.40-7.31 (m, 4H), 7.30-7.22 (m, 1H), 6.98-6.93 (m, 2H), 6.21 (s, 1H), 4.54-4.48 (m, 2H).

EXAMPLE 79

5-(3-chloro-4-fluorophenyl)-7-hydroxy-N-(phenylmethyl)pyrazolo[1,5-a]pyrimidine-3-carboxamide (Compound 84)

5-(3-chloro-4-fluorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3-chloro-4-fluorobenzoylacetate in step 1, and replacing 1-phenylpiperazine with commercially available benzylamine in step 3. $^1$H NMR (400 MHz, $d_6$-DMSO): 11.76-11.55 (br. s, 1H), 9.06-8.98 (m, 1H), 8.46 (s, 1H), 8.09-8.03 (m, 1H), 7.85-7.77 (m, 1H), 7.67-7.57 (m, 1H), 7.38-7.31 (m, 4H), 7.30-7.22 (m, 1H), 6.28 (s, 1H), 4.55-4.47 (m, 2H).

EXAMPLE 80

5-(2,5-difluorophenyl)-7-hydroxy-N-(phenylmethyl) pyrazolo[1,5-a]pyrimidine-3-carboxamide (Compound 85)

5-(2,5-difluorophenyl)-7-hydroxy-N-(phenylmethyl) pyrazolo[1,5-a]pyrimidine-3-carboxamide was prepared according to the method of Example 1 by replacing ethyl 3-oxo-3-phenylpropionate with commercially available ethyl 2,5-difluorobenzoylacetate in step 1, and replacing 1-phenylpiperazine with commercially available benzylamine in step 3. $^1$H NMR (400 MHz, $d_6$-DMSO): 12.18-12.00 (br. s, 1H), 9.05-8.96 (m, 1H), 8.49 (s, 1H), 7.70-7.61 (m, 1H), 7.52-7.41 (m, 2H), 7.38-7.31 (m, 4H), 7.30-7.22 (m, 1H), 6.19 (s, 1H), 4.53-4.46 (m, 2H).

EXAMPLE 81

5-(2,4-difluorophenyl)-7-hydroxy-N-(phenylmethyl) pyrazolo[1,5-a]pyrimidine-3-carboxamide (Compound 86)

5-(2,4-difluorophenyl)-7-hydroxy-N-(phenylmethyl) pyrazolo[1,5-a]pyrimidine-3-carboxamide was prepared according to the method of Example 1 by replacing ethyl 3-oxo-3-phenylpropionate with commercially available ethyl 2,4-difluorobenzoylacetate in step 1, and replacing 1-phenylpiperazine with commercially available benzylamine in step 3. $^1$H NMR (400 MHz, $d_6$-DMSO): 12.12-11.96 (br. s, 1H), 9.05-8.94 (m, 1H), 8.48 (s, 1H), 7.85-7.74 (m, 1H), 7.56-7.43 (m, 1H), 7.38-7.21 (m, 6H), 6.12 (s, 1H), 4.53-4.46 (m, 21-1).

EXAMPLE 82

5-(3,5-difluorophenyl)-7-hydroxy-N-(phenylmethyl) pyrazolo[1,5-a]pyrimidine-3-carboxamide (Compound 87)

5-(3,5-difluorophenyl)-7-hydroxy-N-(phenylmethyl) pyrazolo[1,5-a]pyrimidine-3-carboxamide was prepared according to the method of Example 1 by replacing ethyl 3-oxo-3-phenylpropionate with commercially available ethyl 3,5-difluorobenzoylacetate in step 1, and replacing 1-phenylpiperazine with commercially available benzylamine in step 3. $^1$H NMR (400 MHz, $d_6$-DMSO): 11.80-11.44 (br. s, 1H), 9.08-8.98 (m, 1H), 8.48 (s, 1H), 7.65-7.45 (m, 3H), 7.40-7.20 (m, 5H), 6.34 (s, 1H), 4.55-4.48 (m, 2H).

EXAMPLE 83

7-hydroxy-5-phenyl-N-pyrrolidin-3-ylpyrazolo[1,5-a]pyrimidine-3-carboxamide (Compound 88)

7-hydroxy-5-phenyl-N-pyrrolidin-3-ylpyrazolo[1,5-a]pyrimidine-3-carboxamide was prepared according to the method of Example 1 by replacing 1-phenylpiperazine with commercially available 1-N-Boc-3-aminopyrrolindine in step 3 followed by Boc deprotection under standard conditions. $^1$H NMR (400 MHz, $d_6$-DMSO): 11.31 (broad s, 1H), 8.94 (m, 1H), 8.82 (m, 1H), 8.58 (m, 1H), 8.38 (m, 1H), 7.79 (m, 2H), 7.58 (m, 3H), 6.28 (s, 1H), 4.49 (m, 1H), 3.58-3.14 (m, 4H), 2.23 (m, 1H), 2.02 (m, 1H).

EXAMPLE 84

5-phenyl-3-(piperazin-1-ylcarbonyl)pyrazolo (Compound 89)

5-phenyl-3-(piperazin-1-ylcarbonyl)pyrazolo[1,5-a]pyrimidin-7-ol was prepared according to the method of Example 1 by replacing 1-phenylpiperazine with commercially available 1-N-Boc-piperazine in step 3 followed by Boc deprotection under standard conditions.

EXAMPLE 85

3-[(4-acetylpiperazin-1-yl)carbonyl]-5-phenylpyrazolo[1,5-a]pyrimidin-7-ol (Compound 90)

3-[(4-acetylpiperazin-1-yl)carbonyl]-5-phenylpyrazolo[1,5-a]pyrimidin-7-ol was prepared according to the method of Example 1 by replacing 1-phenylpiperazine with commercially available 1-acetylpiperazine in step 3. $^1$H NMR (400 MHz, $d_6$-DMSO): 12.11 (broad s, 1H), 8.20 (s, 1H), 7.81 (m, 2H), 7.62 (m, 3H), 6.22 (s, 1H), 3.70 (m, 4H), 3.55 (m, 4H), 2.17 (s, 3H).

EXAMPLE 86

3-{[4-(methylsulfonyl)piperazin-1-yl]carbonyl}-5-phenylpyrazolo[1,5-a]pyrimidin-7-ol (Compound 91)

3-{([4-(methylsulfonyl)piperazin-1-yl]carbonyl}-5-phenylpyrazolo[1,5-a]pyrimidin-7-ol was prepared according to the method of Example 1 by replacing 1-phenylpiperazine with commercially available 1-methylsulfonylpiperazine in step 3. $^1$H NMR (400 MHz, $d_6$-DMSO): 12.17 (broad s, 1H), 8.18 (s, 1H), 7.81 (m, 2H), 7.61 (m, 3H), 6.21 (s, 1H), 3.76 (m, 4H), 3.21 (m, 4H), 2.92 (s, 3H).

EXAMPLE 87

N-(1-acetylpiperidin-4-yl)-7-hydroxy-5-phenylpyrazolo[1,5-a]pyrimidine-3-carboxamide (Compound 92)

N-(1-acetylpiperidin-4-yl)-7-hydroxy-5-phenylpyrazolo[1,5-a]pyrimidine-3-carboxamide was prepared according to the method of Example 1 by replacing 1-phenylpiperazine with commercially available 1-acetylpiperidin-4-ylamine in step 3.
$^1$H NMR (400 MHz, $d_6$-DMSO): 11.28 (broad s, 1H), 8.44 (s, 1H), 8.34 (d, 1H), 7.84 (dd, 2H), 7.62 (m, 3H), 6.31 (s, 1H), 4.36 (d, 1H), 4.03 (m, 1H), 3.86 (d, 1H), 3.14 (t, 1H), 2.66 (t, 1H), 2.03 (s, 3H), 1.88 (m, 2H), 1.45 (m, 2H).

EXAMPLE 88

7-hydroxy-N-[1-(methylsulfonyl)piperidin-4-yl]-5-phenylpyrazolo[1,5-a]pyrimidine-3-carboxamide (Compound 93)

7-hydroxy-N-[1-(methylsulfonyl)piperidin-4-yl]-5-phenylpyrazolo[1,5-a]pyrimidine-3-carboxamide was prepared according to the method of Example 1 by replacing 1-phenylpiperazine with commercially available 1-methylsulfonylpiperidin-4-ylamine in step 3. $^1$H NMR (400 MHz, $d_6$-DMSO): 11.29 (broad s, 1H), 8.43 (s, 1H), 8.39 (d, 1H), 7.83 (d, 2H), 7.61 (m, 3H), 6.31 (s, 1H), 3.95 (m, 1H), 3.60 (d, 2H), 2.90 (s, 3H), 2.86 (m, 2H), 1.97 (m, 2H), 1.60 (m, 2H).

EXAMPLE 89

7-hydroxy-N-[(1-methylpiperidin-4-yl)methyl]-5-phenylpyrazolo[1,5-a]pyrimidine-3-carboxamide (Compound 94)

7-hydroxy-N-[(1-methylpiperidin-4-yl)methyl]-5-phenylpyrazolo[1,5-a]pyrimidine-3-carboxamide was prepared according to the method of Example 1 by replacing 1-phenylpiperazine with commercially available 1-methylpiperidin-4-ylmethylamine in step 3.
$^1$H NMR (400 MHz, $d_6$-DMSO): 11.28 (broad s, 1H), 10.34 (broad s, 1H), 8.74 (m, 1H), 8.51 (d, 1H), 7.81 (m, 2H), 7.62 (m, 3H), 6.31 (s, 1H), 3.47 (m, 1H), 3.46 (m, 2H), 3.21 (m, 2H), 2.92 (m, 2H), 2.70 (m, 3H), 1.89 (m, 2H), 1.50 (m, 2H).

EXAMPLE 90

7-hydroxy-N-(1-methylpyrrolidin-3-yl)-5-phenylpyrazolo[1,5-a]pyrimidine-3-carboxamide (Compound 95)

7-hydroxy-N-(1-methylpyrrolidin-3-yl)-5-phenylpyrazolo[1,5-a]pyrimidine-3-carboxamide was prepared according to the method of Example 1 by replacing 1-phenylpiperazine with commercially available 1-methylpyrrolidin-3-ylamine in step 3.

EXAMPLE 91

7-hydroxy-N-[(2-morpholin-4-ylphenyl)methyl]-5-phenylpyrazolo[1,5-a]pyrimidine-3-carboxamide (Compound 96)

7-hydroxy-N-[(2-morpholin-4-ylphenyl)methyl]-5-phenylpyrazolo[1,5-a]pyrimidine-3-carboxamide was prepared according to the method of Example 1 by replacing 1-phenylpiperazine with commercially available 2-morpholinobenzylamine in step 3. $^1$H NMR (400 MHz, $d_6$-DMSO): 11.36 (broad s, 1H), 8.98 (m, 1H), 8.48 (s, 1H), 7.83 (dd, 2H), 7.62 (m, 3H), 7.27 (m, 2H), 7.10 (m, 2H), 6.30 (s, 1H), 4.62 (d, 2H), 3.76 (m, 4H), 2.88 (m, 4H).

EXAMPLE 92

7-hydroxy-N-[1-(methylsulfonyl)pyrrolidin-3-yl]-5-phenylpyrazolo[1,5-a]pyrimidine-3-carboxamide (Compound 97)

7-hydroxy-N-[1-(methylsulfonyl)pyrrolidin-3-yl]-5-phenylpyrazolo[1,5-a]pyrimidine-3-carboxamide was prepared according to the method of Example 1 by replacing 1-phenylpiperazine with 1-(methylsulfonyl)pyrrolidin-3ylamine in step 3.
$^1$H NMR (400 MHz, $d_6$-DMSO): 11.34 (broad s, 1H), 8.58 (d, 1H), 8.45 (s, 1H), 7.83 (m, 2H), 7.62 (m, 3H), 6.30 (s, 1H), 4.48 (m, 1H), 3.58 (m, 1H), 3.34 (m, 1H), 3.21 (m, 1H), 2.93 (s, 3H), 2.21 (m, 1H), 1.99 (m, 1H).

EXAMPLE 93

3-[(4-ethylpiperazin-1-yl)carbonyl]-5-phenylpyrazolo[1,5-a]pyrimidin-7-ol (Compound 98)

3-[(4-ethylpiperazin-1-yl)carbonyl]-5-phenylpyrazolo[1,5-a]pyrimidin-7-ol was prepared according to the method of Example 1 by replacing 1-phenylpiperazine with commercially available 1-ethylpiperazine in step 3. $^1$H NMR (400 MHz, $d_6$-DMSO): 12.17 (broad s, 1H), 9.90 (broad s, 1H), 8.21 (s, 1H), 7.79 (m, 2H), 7.59 (m, 3H), 6.23 (s, 1H), 3.53 (m, 2H); 3.19 (m, 2H), 3.04 (m, 2H), 1.25 (t, 3H).

EXAMPLE 94

3-{[4-(1-methylethyl)piperazin-1-yl]carbonyl}-5-phenylpyrazolo[1,5-a]pyrimidin-7-ol (Compound 99)

3-{[4-(1-methylethyl)piperazin-1-yl]carbonyl}-5-phenylpyrazolo[1,5-a]pyrimidin-7-ol was prepared according to the method of Example 1 by replacing 1-phenylpiperazine with commercially available 1-isopropylpiperazine in step 3. $^1$H NMR (400 MHz, $d_6$-DMSO): 12.16 (broad s, 1H), 9.75

(broad s, 1H), 8.18 (s, 1H), 7.78 (dd, 2H), 7.57 (m, 3H), 6.21 (s, 1H), 3.57 (m, 1H), 3.44 (m, 4H), 3.11 (m, 4H), 1.25 (d, 6H).

EXAMPLE 95

7-hydroxy-N-(1-methylpiperidin-4-yl)-5-phenylpyrazolo[1,5-a]pyrimidine-3-carboxamide (Compound 100)

7-hydroxy-N-(1-methylpiperidin-4-yl)-5-phenylpyrazolo[1,5-a]pyrimidine-3-carboxamide was prepared according to the method of Example 1 by replacing 1-phenylpiperazine with commercially available 1-methylpiperidin-4-ylamine in step 3.
$^1$H NMR (400 MHz, $d_6$-DMSO): 11.22 (broad s, 1H), 9.34 (broad s, 1H), 8.47 (d, 1H), 8.45 (s, 1H), 7.81 (d, 2H), 7.57 (m, 3H), 6.29 (s, 1H), 4.00 (m, 1H), 3.49 (m, 2H), 3.11 (m, 2H), 2.81 (m, 3H), 2.09 (m, 2H), 1.72 (m, 2H).

EXAMPLE 96

5-(3,4-difluorophenyl)-7-hydroxy-N-(phenylmethyl)pyrazolo[1,5-a]pyrimidine-3-carboxamide (Compound 101)

5-(3,4-difluorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 3,4-difluorobenzoylacetate in step 1, and replacing 1-phenylpiperazine with commercially available benzylamine in step 3. $^1$H NMR (400 MHz, $d_6$-DMSO): 11.68-11.44 (br. s, 1H), 9.07-9.00 (m, 1H), 8.46 (s, 1H), 8.02-7.92 (m, 1H) 7.72-7.59 (m, 2I-1), 7.38-7.30 (m, 4H), 7.29-7.22 (m, 1H), 6.29 (s, 1H), 4.55-4.49 (m, 2H).

EXAMPLE 97

5-(2,3-difluorophenyl)-7-hydroxy-N-(phenylmethyl)pyrazolo[1,5-a]pyrimidine-3-carboxamide (Compound 102)

5-(2,3-difluorophenyl)-7-hydroxy-N-(phenylmethyl)pyrazolo[1,5-a]pyrimidine-3-carboxamide was prepared according to the method of Example 1 by replacing ethyl 3-oxo-3-phenylpropionate with commercially available ethyl 2,3-difluorobenzoylacetate in step 1 and replacing 1-phenylpiperazine with commercially available benzylamine in step 3.

EXAMPLE 98

7-hydroxy-N-(phenylmethyl)-5-[4-(trifluoromethyl)phenyl]pyrazolo[1,5-a]pyrimidine-3-carboxamide (Compound 103)

7-hydroxy-N-(phenylmethyl)-5-[4-(trifluoromethyl)phenyl]pyrazolo[1,5-a]pyrimidine-3-carboxamide was prepared according to the method of Example 1 by replacing ethyl 3-oxo-3-phenylpropionate with commercially available ethyl 4-trifluoromethylbenzoylacetate in step 1 and replacing 1-phenylpiperazine with commercially available benzylamine in step 3. $^1$H NMR (400 MHz, $d_6$-DMSO): 11.75-11.65 (br. s, 1H), 9.09-9.00 (m, 1H), 8.48 (s, 1H), 8.15-7.82 (m, 4H), 7.38-7.30 (m, 4H), 7.29-7.22 (m, 1H), 6.33 (s, 1H), 4.54-4.48 (m, 2H).

EXAMPLE 99

3-(1,4'-bipiperidin-1'-ylcarbonyl)-5-phenylpyrazolo[1,5-a]pyrimidin-7-ol (Compound 104)

3-(1,4'-bipiperidin-1'-ylcarbonyl)-5-phenylpyrazolo[1,5-a]pyrimidin-7-ol was prepared according to the method of Example 1 by replacing 1-phenylpiperazine with commercially available 4-piperidinopiperidine in step 3. $^1$H NMR (400 MHz, $d_6$-DMSO): 12.15 (broad s, 1H), 10.52 (broad s, 1H), 8.19 (s, 1H), 7.79 (m, 2H), 7.59 (m, 3H), 6.21 (s, 1H), 3.46 (m, 1H), 2.90 (d, 4H), 2.51 (m, 4H), 2.16 (m, 2H), 1.86-1.68 (m, 7H), 1.38 (m, 1H).

EXAMPLE 100

5-phenyl-3-[(4-pyrrolidin-1-ylpiperidin-1-yl)carbonyl]pyrazolo[1,5-a]pyrimidin-7-ol (Compound 105)

5-phenyl-3-[(4-pyrrolidin-1-ylpiperidin-1-yl)carbonyl]pyrazolo[1,5-a]pyrimidin-7-ol was prepared according to the method of Example 1 by replacing 1-phenylpiperazine with commercially available 4-pyrrolidinopiperidine in step 3. $^1$H NMR (400 MHz, $d_6$-DMSO): 12.15 (broad s, 1H), 11.10 (broad s, 1H), 8.20 (s, 1H), 7.80 (m, 2H), 7.59 (m, 3H), 6.22 (s, 1H), 3.41 (m, 4H), 3.04 (m, 4H), 2.12 (d, 2H), 1.89 (m, 4H), 1.69 (m, 2H).

EXAMPLE 101

7-hydroxy-N-(phenylmethyl)-5-(2,4,5-trifluorophenyl)pyrazolo[1,5-a]pyrimidine-3-carboxamide (Compound 106)

7-hydroxy-N-(phenylmethyl)-5-(2,4,5-trifluorophenyl)pyrazolo[1,5-a]pyrimidine-3-carboxamide was prepared according to the method of Example 1 by replacing ethyl 3-oxo-3-phenylpropionate with commercially available ethyl 2,4,5-trifluorobenzoylacetate in step one and replacement of 1-phenylpiperazine with commercially available benzylamine in step 3.

$^1$H NMR (400 MHz, $d_6$-DMSO): 12.21-12.09 (br. s, 1H), 9.05-8.96 (m, 1H), 8.49 (s, 1H), 8.00-7.90 (m, 1H), 7.86-7.75 (m, 1H), 7.38-7.30 (m, 4H), 7.29-7.22 (m, 1H), 6.16 (s, 1H), 4.53-4.46 (m, 2H).

EXAMPLE 102

5-(2,4-difluorophenyl)-N-[1-ethylpiperidin-4-yl)methyl]-7-hydroxypyrazolo[1,5-a]pyrimidine-3-carboxamide (Compound 107)

5-(2,4-difluorophenyl)-N-[(1-ethylpiperidin-4-yl)methyl]-7-hydroxypyrazolo[1,5-a]pyrimidine-3-carboxamide was prepared according to the method of Example 1 by replacing ethyl 3-oxo-3-phenylpropionate with commercially available ethyl 2,4-difluorobenzoylacetate in step one and replacing 1-phenylpiperazine with commercially available 1-ethylpiperidin-4-ylmethylamine in step 3.

$^1$H NMR (400 MHz, $d_6$-DMSO): 12.00-11.94 (br. s, 1H), 8.61-8.54 (m, 1H), 8.47 (s, 1H), 7.86-7.75 (m, 1H), 7.57-7.46 (m, 1H), 7.32-7.24 (m, 1H), 6.13 (s, 1H), 3.51-3.43 (m, 2H), 3.26-2.98 (m, 5H), 2.91-2.76 (m, 2H), 1.93-1.72 (m, 3H), 1.54-1.38 (m, 1H), 1.23 (t, 3H).

EXAMPLE 103

5-(3-chloro-4-fluorophenyl)-N-[(1-ethylpiperidin-4-yl)methyl]-7-hydroxypyrazolo[1,5-a]pyrimidine-3-carboxamide (Compound 108)

5-(3-chloro-4-fluorophenyl)-N-[(1-ethylpiperidin-4-yl)methyl]-7-hydroxypyrazolo[1,5-a]pyrimidine-3-carboxamide was prepared according to the method of Example 1 by replacing ethyl 3-oxo-3-phenylpropionate with commercially available ethyl 3-chloro-4-fluorobenzoylacetate in step one and replacing 1-phenylpiperazine with commercially available 1-ethylpiperidin-4-ylmethylamine in step 3.

EXAMPLE 104

5-(4-fluorophenyl)-7-hydroxy-N-{[1-(1-methylethyl)piperidin-4-yl]methyl}pyrazolo[1,5-a]pyrimidine-3-carboxamide (Compound 109)

5-(4-fluorophenyl)-7-hydroxy-N-{[1-(1-methylethyl)piperidin-4-yl]methyl}pyrazolo[1,5-a]pyrimidine-3-carboxamide was prepared according to the method of Example 1 by replacing ethyl 3-oxo-3-phenylpropionate with commercially available ethyl 4-fluorobenzoylacetate in step 1 and replacing 1-phenylpiperazine with commercially available 1-isopropylpiperidin-4-ylmethylamine in step 3. $^1$H NMR (400 MHz, CD$_3$OD): 8.33 (s, 1H), 7.90-7.87 (m, 2H), 7.38-7.33 (m, 2H), 6.27 (s, 1H), 3.53-3.47 (m, 3H), 3.38-3.35 (m, 2H), 3.08-3.00 (m, 2H), 2.13-2.08 (m, 2H), 2.01-1.94 (m, 1H), 1.63-1.54 (m, 2H), 1.36 (d, 6H).

EXAMPLE 105

5-(4-fluorophenyl)-7-hydroxy-N-[(1-methylpiperidin-4-yl)methyl]pyrazolo[1,5-a]pyrimidine-3-carboxamide (Compound 110)

5-(4-fluorophenyl)-7-hydroxy-N-[(1-methylpiperidin-4-yl)methyl]pyrazolo[1,5-a]pyrimidine-3-carboxamide was prepared according to the method of Example 1 by replacing ethyl 3-oxo-3-phenylpropionate with commercially available ethyl 4-fluorobenzoylacetate in step 1 and replacing 1-phenylpiperazine with commercially available 1-methylpiperidin-4-ylmethylamine in step 3. $^1$H NMR (400 MHz, d$_6$-DMSO): 11.36 (s, 1H), 9.88 (s, 1H), 8.64 (s, 1H), 8.46 (s, 1H), 7.92-7.84 (m, 2H), 7.47-7.41 (m, 2H), 6.27 (s, 1H), 3.22-3.18 (m, 2H), 2.93-2.84 (m, 2H), 2.71 (s, 3H), 1.91-1.84 (m, 2H), 1.79-1.71 (m, 1H), 1.52-1.41 (m, 2H).

EXAMPLE 106

N-[(1-ethylpiperidin-4-yl)methyl]-5-(4-fluorophenyl)-7-hydroxypyrazolo[1,5-a]pyrimidine-3-carboxamide (Compound 111)

N-[(1-ethylpiperidin-4-yl)methyl]-5-(4-fluorophenyl)-7-hydroxypyrazolo[1,5-a]pyrimidine-3-carboxamide was prepared according to the method of Example 1 by replacing ethyl 3-oxo-3-phenylpropionate with commercially available ethyl 4-fluorobenzoylacetate in step 1 and replacing 1-phenylpiperazine with commercially available 1-ethylpiperidin-4-ylmethylamine in step 3. $^1$H NMR (400 MHz, CD$_3$OD): 8.36 (m, 1H), 7.94-7.88 (m, 2H), 7.39-7.32 (m, 2H), 6.28 (s, 1H), 3.76-3.58 (m, 4H), 3.39-3.34 (m, 1H), 3.20-3.14 (m, 2H), 2.98-2.89 (m, 2H), 2.12-2.06 (m, 2H), 2.00-1.94 (m, 2H), 1.59-1.49 (m, 1H), 1.36-1.31 (m, 3H).

EXAMPLE 107

7-hydroxy-N-{[1-(2-methylpropyl)piperidin-4-yl]methyl}-5-phenylpyrazolo[1,5-a]pyrimidine-3-carboxamide (Compound 112)

7-hydroxy-N-{[1-(2-methylpropyl)piperidin-4-yl]methyl}-5-phenylpyrazolo[1,5-a]pyrimidine-3-carboxamide was prepared according to the method of Example 1 by replacing 1-phenylpiperazine with commercially available 1-isobutylpiperidin-4-ylmethylamine in step 3. $^1$H NMR (400 MHz, d$_6$-DMSO): 11.28 (broad s, 1H), 9.37 (broad s, 1H), 8.71 (m, 1H), 8.49 (s, 1H), 7.81 (d, 2H), 7.62 (m, 3H), 6.31 (s, 1H), 3.71 (m, 1H), 3.34 (m, 4H), 2.85 (m, 4H), 2.08 (m, 1H), 1.86 (m, 4H), 1.63 (m, 2H), 0.96 (m, 6H).

EXAMPLE 108

N-[(1-ethylpiperidin-4-yl)methyl]-7-hydroxy-5-phenylpyrazolo[1,5-a]pyrimidine-3-carboxamide (Compound 113)

N-[(1-ethylpiperidin-4-yl)methyl]-7-hydroxy-5-phenylpyrazolo[1,5-a]pyrimidine-3-carboxamide was prepared according to the method of Example 1 by replacing 1-phenylpiperazine with commercially available 1-ethylpiperidin-4-ylmethylamine in step 3. $^1$H NMR (400 MHz, d$_6$-DMSO): 11.28 (broad s, 1H), 10.16 (broad s, 1H), 8.75 (m, 1H), 8.51 (s, 1H), 7.82 (m, 2H), 7.62 (m, 3H), 6.31 (s, 1H), 3.48 (m, 2H), 3.20 (m, 2H), 3.04 (m, 2H), 2.81 (m, 2H), 1.86 (m, 3H), 1.53 (m, 2H), 1.24 (m, 3H).

EXAMPLE 109

7-hydroxy-N-{[1-(1-methylethyl)piperidin-4-yl]methyl}-5-phenylpyrazolo[1,5-a]pyrimidine-3-carboxamide (Compound 114)

7-hydroxy-N-{[1-(1-methylethyl)piperidin-4-yl]methyl}-5-phenylpyrazolo[1,5-a]pyrimidine-3-carboxamide was prepared according to the method of Example 1 by replacing 1-phenylpiperazine with commercially available 1-isopropylpiperidin-4-ylmethylamine in step 3. $^1$H NMR (400 MHz, d$_6$-DMSO): 11.28 (broad s, 1H), 10.18 (broad s, 1H), 8.78 (m, 1H), 8.52 (s, 1H), 7.82 (m, 1H), 7.62 (m, 3H), 6.31 (s, 1H), 3.84 (m, 4H), 3.36 (m, 2H), 3.19 (m, 2H), 2.89 (m, 2H), 1.89 (m, 2H), 1.67 (m, 2H), 1.27 (d, 6H).

EXAMPLE 110

7-hydroxy-N-{[4-(4-methylpiperazin-1-yl)phenyl]methyl}-5-phenylpyrazolo[1,5-a]pyrimidine-3-carboxamide (Compound 115)

7-hydroxy-N-{[4-(4-methylpiperazin-1-yl)phenyl]methyl}-5-phenylpyrazolo[1,5-a]pyrimidine-3-carboxamide was prepared according to the method of Example 1 by replacing 1-phenylpiperazine with commercially available 4-(1-methylpiperazin-4-yl)benzylamine in step 3. $^1$H NMR (400 MHz, d$_6$-DMSO): 11.28 (broad s, 1H), 10.67 broad s, 1H), 9.02 (t, 1H), 8.46 (s, 1H), 7.79 (d, 2H), 7.58 (m, 3H), 7.42

(d, 2H), 7.22 (d, 2H), 6.29 (s, 1H), 5.41 (d, 2H), 3.75 (d, 2H), 3.49 (m, 2H), 3.14-2.99 (m, 2H), 2.79 (m, 3H).

EXAMPLE 111

5-(2,4-difluorophenyl)-7-hydroxy-N-[(1-methylpiperidin-4-yl)methyl]pyrazolo[1,5-a]pyrimidine-3-carboxamide (Compound 116)

5-(2,4-difluorophenyl)-7-hydroxy-N-[(1-methylpiperidin-4-yl)methyl]pyrazolo[1,5-a]pyrimidine-3-carboxamide was prepared according to the method of Example 1 by replacing ethyl 3-oxo-3-phenylpropionate with commercially available ethyl 2,4-difluorobenzoylacetate in step one and replacement of 1-phenylpiperazine with commercially available 1-methylpiperidin-4-ylmethylamine in step 3. $^1$H NMR (400 MHz, $d_6$-DMSO): 12.01-11.93 (br. s, 1H), 10.09-9.95 (br. s, 1H), 8.65-8.57 (m, 1H), 8.51-8.45 (br. s, 1H), 7.87-7.73 (m, 1H), 7.56-7.42 (m, 1H), 7.34-7.23 (m, 1H), 6.13 (s, 1H), 3.77-2.62 (m, 8H), 1.98-1.26 (m, 6I-1).

EXAMPLE 112

5-(2,4-difluorophenyl)-7-hydroxy-N-{[1-(2-methylpropyl)piperidin-4-yl]methyl}pyrazolo[1,5-a]pyrimidine-3-carboxamide (Compound 117)

5-(2,4-difluorophenyl)-7-hydroxy-N-{[1-(2-methylpropyl)piperidin-4-yl]methyl}pyrazolo[1,5-a]pyrimidine-3-carboxamide was prepared according to the method of Example 1 by replacing ethyl 3-oxo-3-phenylpropionate with commercially available ethyl 2,4-difluorobenzoylacetate in step one and replacing 1-phenylpiperazine with commercially available 1-isobutylpiperidin-4-ylmethylamine in step 3. $^1$H NMR (400 MHz, $d_6$-DMSO): 12.04-11.93 (br. s, 1H), 9.60-9.45 (br. s, 1H), 8.72-8.62 (m, 1H), 8.56-8.48 (br. s, 1H), 7.87-7.75 (m, 1H), 7.58-7.46 (m, 1H), 7.35-7.22 (m, 1H), 6.13 (s, 1H), 3.87-2.74 (m, 9H), 2.17-1.99 (m, 1H), 1.95-1.58 (m, 4H), 0.97 (d, 6H).

EXAMPLE 113

5-(4-fluorophenyl)-7-hydroxy N-{[1-(2-methylpropyl)piperidin-4-yl]methyl}pyrazolo[1,5-a]pyrimidine-3-carboxamide (Compound 118)

5-(4-fluorophenyl)-7-hydroxy-N-{[1-(2-methylpropyl)piperidin-4-yl]methyl}pyrazolo[1,5-a]pyrimidine-3-carboxamide was prepared according to the method of Example 1 by replacing ethyl 3-oxo-3-phenylpropionate with commercially available ethyl 4-fluorobenzoylacetate in step 1 and replacing 1-phenylpiperazine with commercially available 1-isobutylpiperidin-4-ylmethylamine in step 3. $^1$H NMR (400 MHz, $CD_3OD$): 8.33 (s, 1H), 7.92-7.88 (m, 2H), 7.39-7.34 (m, 2H), 6.28 (s, 1H), 3.75-3.57 (m, 6H), 3.38-3.34 (m, 2H), 2.98-2.94 (m, 4H), 2.08-2.04 (m, 1H), 1.63-1.58 (m, 1H), 1.05 (d, 6I-1).

EXAMPLE 114

5-(2,4-difluorophenyl)-7-hydroxy-N-{[1-(1-methylethyl)piperidin-4-yl]methyl}pyrazolo[1,5-a]pyrimidine-3-carboxamide (Compound 119)

5-(2,4-difluorophenyl)-7-hydroxy-N-{[1-(1-methylethyl)piperidin-4-yl]methyl}pyrazolo[1,5-a]pyrimidine-3-carboxamide was prepared according to the method of Example 1 by replacing ethyl 3-oxo-3-phenylpropionate with commercially available ethyl 2,4-difluorobenzoylacetate in step 1 and replacing 1-phenylpiperazine with commercially available 1-isopropylpiperidin-4-ylmethylamine in step 3. $^1$H NMR (400 MHz, $d_6$-DMSO): 12.04-11.94 (br. s, 1H), 9.96-9.80 (br. s, 1H), 8.68-8.62 (m, 1H), 8.54-8.48 (br. s, 1H), 7.85-7.76 (m, 1H), 7.56-7.47 (m, 1H), 7.32-7.24 (m, 1H), 6.13 (s, 1H), 3.52-3.28 (m, 3H), 3.25-3.11 (m, 2H), 2.97-2.80 (m, 2H), 1.94-1.75 (m, 3H), 1.72-1.52 (m, 2H), 1.25 (d, 6H).

EXAMPLE 115

5-(3-chloro-4-fluorophenyl)-7-hydroxy-N-{[1-(1-methylethyl)piperidin-4-yl]methyl}pyrazolo[1,5-a]pyrimidine-3-carboxamide (Compound 120)

5-(3-chloro-4-fluorophenyl)-7-hydroxy-N-{[1-(1-methylethyl)piperidin-4-yl]methyl}pyrazolo[1,5-a]pyrimidine-3-carboxamide was prepared according to the method of Example 1 by replacing ethyl 3-oxo-3-phenylpropionate with commercially available ethyl 3-chloro-4-fluorobenzoylacetate in step 1 and replacing 1-phenylpiperazine with commercially available 1-isopropylpipericlin-4-ylmethylamine in step 3. $^1$H NMR (400 MHz, $d_6$-DMSO): 11.62 (broad s, 1H), 9.95 (broad s, 1H), 8.67 (m, 1H), 8.48 (s, 1H), 8.07 (m, 1H), 7.81 (m, 1H), 7.61 (m, 1H), 6.29 (s, 1H), 3.68 (m, 2H), 3.34 (m, 2H), 2.91 (m, 2H), 1.90 (m, 2H), 1.63 (m, 2H), 1.26 (m, 6H).

EXAMPLE 116

N-[(1-ethylpyrrolidin-2-yl)methyl]-7-hydroxy-5-phenylpyrazolo[1,5-a]pyrimidine-3-carboxamide (Compound 121)

N-[(1-ethylpyrrolidin-2-yl)methyl]-7-hydroxy-5-phenylpyrazolo[1,5-a]pyrimidine-3-carboxamide was prepared according to the method of Example 1 by replacing 1-phenylpiperazine with commercially available 2-(aminomethyl)-1-ethylpyrrolidine in step 3. $^1$H NMR (400 MHz, $d_6$-DMSO): 11.30 (broad s, 1H), 10.06 (broad s, 1H), 9.01 (s, 1H), 8.48 (s, 1H), 7.80 (d, 2H), 7.57 (m, 3H), 6.29 (s, 1H), 3.70 (m, 4H), 3.08 (m, 2H), 2.14-1.81 (m, 4H), 1.30 (t, 3H).

EXAMPLE 117

7-hydroxy-N-[(1-methylpiperidin-2-yl)methyl]-5-phenylpyrazolo[1,5-a]pyrimidine-3-carboxamide (Compound 122)

7-hydroxy-N-[(1-methylpiperidin-2-yl)methyl]-5-phenylpyrazolo[1,5-a]pyrimidine-3-carboxamide was prepared according to the method of Example 1 by replacing 1-phenylpiperazine with commercially available 1-methyl-piperidin-2-ylmethylamine in step 3. $^1$H NMR (400 MHz, $d_6$-DMSO): 11.30 (broad s, 1H), 10.47 (borad s, 1H), 8.92 (m, 1H), 8.59 (m, 1H), 7.79 (m, 2H), 7.57 (m, 3H), 6.29 (s, 1H), 3.72-3.00 (m, 6H), 2.88 (d, 2H), 1.91-1.43 (m, 6H).

EXAMPLE 118

7-hydroxy-N-[(1-methylpiperidin-3-yl)methyl]-5-phenylpyrazolo[1,5-a]pyrimidine-3-carboxamide (Compound 123)

7-hydroxy-N-[(1-methylpiperidin-3-yl)methyl]-5-phenylpyrazolo[1,5-a]pyrimidine-3-carboxamide Prepared according to the method of Example 1 by replacing 1-phenylpiperazine with commercially available 1-methyl-piperidin-3-ylmethylamine in step 3.

$^1$H NMR (400 MHz, d$_6$-DMSO): 11.30 (broad s, 1H), 10.47 (borad s, 1H), 8.92 (m, 1H), 8.59 (m, 1H), 7.79 (m, 2H), 7.57 (m, 3H), 6.29 (s, 1H), 3.72-3.00 (m, 6H), 2.88 (d, 2H), 1.91-1.43 (m, 6H).

EXAMPLE 119

7-hydroxy-N-[(1-methylpyrrolidin-2-yl)methyl]-5-phenylpyrazolo[1,5-a]pyrimidine-3-carboxamide (Compound 124)

7-hydroxy-N-[(1-methylpyrrolidin-2-yl)methyl]-5-phenylpyrazolo[1,5-a]pyrimidine-3-carboxamide was prepared according to the method of Example 1 by replacing 1-phenylpiperazine with commercially available 1-methyl-pyrrolidin-2-ylmethylamine in step 3. $^1$H NMR (400 MHz, d$_6$-DMSO): 11.30 (broad s, 1H), 9.07 (m, 1H), 8.56 (m, 1H), 7.80 (m, 2H), 7.59 (m, 3H), 6.29 (s, 1H), 339-3.37 (m, 4H), 3.04 (m, 1H), 2.89 (s, 3H), 2.16-1.75 (m, 4H).

EXAMPLE 120

5-(3-chloro-4-fluorophenyl)-7-hydroxy-N-[(1-methylpiperidin-4-yl)methyl]pyrazolo[1,5-a]pyrimidine-3-carboxamide (Compound 125)

5-(3-chloro-4-fluorophenyl)-7-hydroxy-N-[(1-methylpiperidin-4-yl)methyl]pyrazolo[1,5-a]pyrimidine-3-carboxamide was prepared according to the method of Example 1 by replacing ethyl 3-oxo-3-phenylpropionate with commercially available ethyl 3-chloro-4-fluorobenzoylacetate in step 1 and replacing 1-phenylpiperazine with commercially available 1-methylpiperidin-4-ylmethylamine in step 3. $^1$H NMR (400 MHz, d$_6$-DMSO): 11.60 (broad s, 1H), 10.19 (broad s, 1H), 8.66 (m, 1H), 8.47 (s, 1H), 8.05 (m, 1H), 7.81 (m, 1H), 7.63 (t, 1H), 6.29 (s, 1H), 3.67-3.37 (m, 4H), 3.20 (s, 3H), 2.92-2.71 (m, 2H), 1.88-1.48 (m, 5H).

EXAMPLE 121

7-hydroxy-N-[(1-methylpyrrolidin-3-yl)methyl]-5-phenylpyrazolo[1,5-a]pyrimidine-3-carboxamide (Compound 126)

7-hydroxy-N-[(1-methylpyrrolidin-3-yl)methyl]-5-phenylpyrazolo[1,5-a]pyrimidine-3-carboxamide was prepared according to the method of Example 1 by replacing 1-phenylpiperazine with commercially available 1-methyl-pyrrolidin-3-ylmethylamine in step 3. $^1$H NMR (400 MHz, CD$_3$OD): 8.41 (s, 1H), 7.83-7.73 (m, 2H), 7.65-7.54 (m, 3H), 6.22 (m, 1H), 3.90-3.46 (m, 5H), 3.25-3.15 (m, 1H), 2.98 (s, 3H), 2.85-2.77 (m, 1H), 2.42-2.20 (m, 1H), 2.09-1.96 (m, 1H).

EXAMPLE 122

7-hydroxy-N-{[2-(4-methylpiperazin-1-yl)phenyl]methyl}-5-phenylpyrazolo[1,5-a]pyrimidine-3-carboxamide (Compound 129)

7-hydroxy-N-{[2-(4-methylpiperazin-1-yl)phenyl]methyl}-5-phenylpyrazolo[1,5-a]pyrimidine-3-carboxamide was prepared according to the method of Example 1 by replacing 1-phenylpiperazine with commercially available 2-(1-methylpiperazin-4-yl)benzylamine in step 3. $^1$H NMR (400 MHz, CD$_3$OD): 7.81 (br m, 2H), 7.61 (br m, 4H), 7.43 (br m, 1H), 7.32 (br m, 2H), 7.20 (br m, 2H), 6.26 (br s, 1H), 4.72 (br m, 2H), 3.65 (br m, 4H), 3.47 (s, 3H), 3.01 (br m, 4H).

Using the same or analogous synthetic techniques described in Example 3 and/or substituting with alternative reagents, the compounds shown in Table 1 were prepared.

Biological Assay

For a biochemical measurement of CK2 inhibitory activity, compounds of the invention were screened in a luciferase-coupled chemiluminescence assay that detects consumption of ATP by the CK2 enzyme. The assay was performed using two different constructs of the enzyme, CK2 holoenzyme and CK2 alpha subunit. The assay buffer is composed of 20 mM Tris, pH 7.5, 10 mM MgCl$_2$, 0.03% Triton-X-1000, 1 mM DTT and 0.1 mM NaVO$_3$.

For the CK2 alpha subunit assay, the assay is performed as follows: 0.5 µl of test compound is added to a microtiter plate, followed by the addition of 100 substrate containing CK2 peptide (RRRDDDSDDD) and ATP and 10 µl of alpha subunit of the CK2 enzyme. The concentration of CK2 peptide is 9 µM, ATP is 2 µM and CK2-alpha subunit is 10 nM.

For the CK2 holoenzyme assay, the assay is performed as follows: 0.5 µl of test compound is added to a microtiter plate, followed by the addition of 10 µl substrate containing casein and ATP and 10 µl of CK2 holoenzyme. The concentration of casein is 2 µM, ATP is 2 µM and CK2 holoenzyme is 6 nM.

For both assays, the mixture is shaken briefly and incubated for 120 min at room temperature. At the end of the incubation, 10 µl of Kinase Glo (luciferase) is added and the signal is detected in a luminescence reader (Victor, Perkin Elmer).

The compounds in Table 1 have been tested for their CK2 inhibitory activity (IC$_{50}$ values), and these compounds have CK2 IC$_{50}$ values of less than 5000 nM. A preferred group of compounds of Table 1 have CK2 IC$_{50}$ values of less than 4000 nm. Another preferred group of compounds of Table 1 have CK2 IC$_{50}$ values of less than 510 nm. Another preferred group of compounds of Table 1 have CK2 IC$_{50}$ values of less than 500 nm. Another preferred group of compounds of Table 1 have CK2 IC$_{50}$ values of less than 200 nm. Another preferred group of compounds of Table 1 have CK2 IC$_{50}$ values of less than 100 nm.

Compounds of the invention may also be active againt PIM 1 and/or PIM 2 kinase activity. Accordingly, compounds of the invention can also be useful for treating proliferative disorders associated with PIM1 and/or PIM 2 kinase activity.

PIM Assay Protocol

PIM kinase activity can be measured by monitoring peptide substrate dependent hydrolysis of ATP via quantitation of remaining ATP with luciferase based chemiluminescence. For compound evaluation, 0.5 ul compound dissolved in DMSO is added to 10 ul of PIM-1 and/or PIM-3 dissolved in assay buffer (20 mM HEPES pH 7.5, 10 mM MgCl2, 0.03% Triton and 1 mM DTT). After preincubation for about 30 minutes at about room temperature, the reaction is initiated by addition of 10 ul of ATP and substrate peptide AKRRRLSA in assay buffer. The reaction mixture is incubated for about 120 min at room temperature, and the reaction progress can be quantitated by addition of 10 ul Kinase-Glo (Promega) and measuring chemiluminescence in a Victor reader (Perkin Elmer). A reaction in which compound is omitted is used to determine maximum reaction progress. Omission of compound and enzyme from the reaction can be used to determine zero reaction progress.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound according to Formula I:

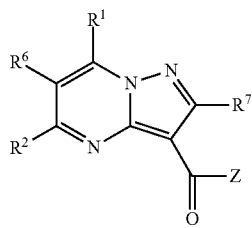

I or a pharmaceutically acceptable salt thereof, wherein:

$R^1$ is selected from —OH, —O—($C_1$-$C_6$)alkyl, and —NH($C_1$-$C_6$)alkyl-phenyl;

$R^2$ is selected from -(5-10 membered)heteroaryl, -(4-10 membered)heterocycloalkyl, phenyl, and —($C_1$-$C_6$)alkyl, wherein the -(5-10 membered)heteroaryl, phenyl and -(4-10 membered)heterocycloalkyl are each optionally substituted with 1-3 groups independently selected from halo, —OH, —$NH_2$, —NH($C_1$-$C_6$)alkyl, —N[($C_1$-$C_6$)alkyl]$_2$, —$NO_2$, —CN, —O—($C_1$-$C_6$)alkyl, —S—($C_1$-$C_6$)alkyl, —$CF_3$, —($C_1$-$C_6$)alkyl, —($C_3$-$C_{10}$)cycloalkyl, and —($C_1$-$C_6$)alkyl-($C_3$-$C_{10}$)cycloalkyl;

$R^3$ is selected from H, —($C_1$-$C_6$)alkyl-phenyl, —C($R^5$)—($C_1$-$C_6$)alkyl-phenyl, —C($R^5$)—($C_1$-$C_6$)alkyl, —C($R^5$)-phenyl, —C($R^5$)—($C_3$-$C_{10}$)cycloalkyl, —C($R^5$)—($C_1$-$C_6$)alkyl-($C_3$-$C_{10}$)cycloalkyl, —C($R^5$)—($C_1$-$C_6$)alkyl-(4-10 membered)heterocycloalkyl, —C($R^5$)-(5-10 membered)heteroaryl, —($C_1$-$C_6$)alkyl-($C_3$-$C_{10}$)cycloalkyl, —($C_3$-$C_{10}$)cycloalkyl, —($C_1$-$C_6$)alkyl-N[($C_1$-$C_6$)alkyl]$_2$, —($C_1$-$C_6$)alkyl, —($C_1$-$C_6$)alkyl-(4-10 membered)heterocycloalkyl, and -(4-10 membered)heterocycloalkyl, wherein each —($C_1$-$C_6$)alkyl-phenyl, —C($R^5$)—($C_1$-$C_6$)alkyl-phenyl, —C($R^5$)—($C_1$-$C_6$)alkyl, —C($R^5$)-phenyl, —C($R^5$)—($C_3$-$C_{10}$)cycloalkyl, —C($R^5$)—($C_1$-$C_6$)alkyl-($C_3$-$C_{10}$)cycloalkyl, —C($R^5$)—($C_1$-$C_6$)alkyl-(4-10 membered)heterocycloalkyl, —C($R^5$)-(4-10 membered)heterocycloalkyl, —($C_3$-$C_{10}$)cycloalkyl, —($C_1$-$C_6$)alkyl-($C_3$-$C_{10}$)cycloalkyl, —($C_1$-$C_6$)alkyl-N[($C_1$-$C_6$)alkyl]$_2$, —($C_1$-$C_6$)alkyl, —($C_1$-$C_6$)alkyl-(4-10 membered)heterocycloalkyl, and -(4-10 membered)heterocycloalkyl are optionally substituted with 1-3 groups independently selected from —($C_1$-$C_6$)alkyl, —O—($C_1$-$C_6$)alkyl, halo, phenyl, —$NO_2$, —C(O)O—($C_1$-$C_6$)alkyl, —C(O)—($C_1$-$C_6$)alkyl, —O-phenyl, —S—$CH_3$, —$SO_2$—$CH_3$, —C(O)$CH_3$, —$CF_3$ and -(4-10 membered)heterocycloalkyl optionally substituted with —($C_1$-$C_6$)alkyl, —$SO_2$—$CH_3$, or —N[($C_1$-$C_6$)alkyl]$_2$;

$R^4$ is H or —($C_1$-$C_6$)alkyl, or $R^3$ and $R^4$, together with the nitrogen atom to which they are attached, form a -(4-10 membered)heterocycloalkyl optionally substituted with 1-3 groups independently selected from halo, —($C_1$-$C_6$)alkyl, —O—($C_1$-$C_6$)alkyl, phenyl, —$SO_2$—($C_1$-$C_6$)alkyl, -(4-10 membered)heterocycloalkyl, -(3-10 membered)cycloalkyl, -(5-10 membered)heteroaryl and —C(O)—($C_1$-$C_6$)alkyl, wherein each phenyl, —$SO_2$—($C_1$-$C_6$)alkyl, -(4-10 membered)heterocycloalkyl, -(3-10 membered)cycloalkyl, and (5-10 membered)heteroaryl is optionally substituted with 1, 2 or 3 groups selected from —($C_1$-$C_6$)alkyl, —O—($C_1$-$C_6$)alkyl, halo, —$NO_2$, phenyl, —($C_3$-$C_{10}$)cycloalkyl, —($C_1$-$C_6$)alkyl-($C_3$-$C_{10}$)cycloalkyl, -(4-10 membered)heterocycloalkyl, —($C_1$-$C_6$)alkyl-(4-10 membered)heterocycloalkyl, -(5-10 membered)heteroaryl, —S—$CH_3$, and —$CF_3$;

$R^5$ is —C(O)O($C_1$-$C_6$)alkyl;

$R^6$ is H;

$R^7$ is H, —NH($C_1$-$C_6$alkyl) or —N[($C_1$-$C_6$)alkyl]$_2$;

$R^8$ is selected from phenyl, —($C_3$-$C_{10}$)cycloalkyl, —($C_1$-$C_6$)alkyl-($C_3$-$C_{10}$)cycloalkyl, -(4-10 membered)heterocycloalkyl, —($C_1$-$C_6$)alkyl-(4-10 membered)heterocycloalkyl, and -(5-10 membered)heteroaryl, —($C_1$-$C_6$)alkyl-(5-10 membered)heteroaryl and —($C_1$-$C_6$)alkyl-phenyl; and Z is —$OR^8$ or —$NR^3R^4$, with the proviso that when $R^1$ is —OH, $R^2$ is $CH_3$, $R^6$ is H, $R^7$ is H, and Z is —$NHR^3$, then $R^3$ is not

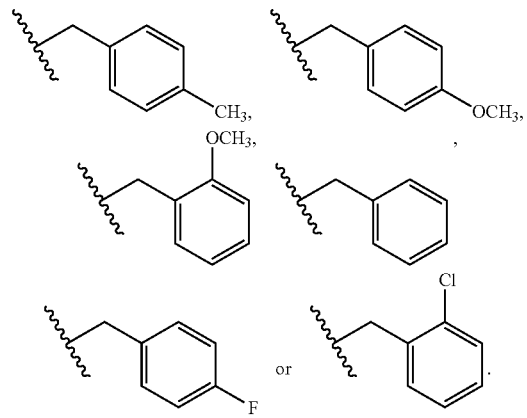

2. The compound according to claim 1, wherein $R^8$ is phenyl or —($C_1$-$C_6$)alkyl-phenyl.

3. The compound according to claim 1, wherein $R^3$ is —($C_1$-$C_6$)alkyl-phenyl substituted with 1-3 groups independently selected from —($C_2$-$C_6$)alkyl, —O—($C_2$-$C_6$)alkyl, Br, phenyl, —$NO_2$, —C(O)O—($C_1$-$C_6$)alkyl, —C(O)—($C_1$-$C_6$)alkyl, —phenyl, —S—$CH_3$, —$SO_2$—$CH_3$, —$CF_3$ and -(5-10 membered)heterocycloalkyl optionally substituted with —($C_1$-$C_6$)alkyl, —$SO_2CH_3$ or —N[($C_1$-$C_6$)alkyl]$_2$.

4. The compound according to claim 1, wherein $R^1$ is OH.

5. The compound according to claim 1, wherein $R^2$ is phenyl optionally substituted with 1, 2 or 3 halo.

6. The compound according to claim 1, wherein $R^3$ is —($C_1$-$C_6$)alkyl-phenyl optionally substituted with morpholinyl or piperizinyl optionally substituted with —($C_1$-$C_6$)alkyl.

7. The compound according to claim 1, wherein $R^3$ is —($C_3$-$C_6$)cycloalkyl optionally substituted with phenyl.

8. A compound of Formula II:

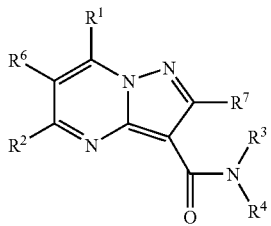

or a pharmaceutically acceptable salt thereof, wherein:
$R^1$ is —OH or —O($C_1$-$C_3$)alkyl;
$R^2$ is independently selected from —($C_1$-$C_3$)alkyl; phenyl optionally substituted with 1-3 groups independently selected from halo, —$CF_3$, —O($C_1$-$C_3$)alkyl, and —($C_1$-$C_3$)alkyl; furanyl and pyridinyl optionally substituted with methyl;
$R^3$ is selected from H, —($C_1$-$C_3$)alkyl-phenyl optionally substituted with 1-3 substituents independently selected from —$OCH_3$, —$NO_2$, halo, phenyl, —S—$CH_3$, —O-phenyl, —($C_1$-$C_3$)alkyl, morpholinyl, —$CF_3$, —($C_1$-$C_6$)alkyl, piperizinyl optionally substituted with —($C_1$-$C_3$)alkyl and —($C_1$-$C_3$)alkyl-piperidinyl optionally substituted with —($C_1$-$C_3$)alkyl; cyclohexyl; —($C_1$-$C_3$) alkyl-N($CH_3$)$_2$; —($C_1$-$C_6$)alkyl; cyclopentyl; piperizinyl optionally substituted with phenyl; —($C_1$-$C_3$)alkyl-morpholinyl; piperidinyl optionally substituted with —$CH_3$, —$SO_2CH_3$, —$CH_2$—$NH_2$, piperidinyl or pyrrolidinyl; 3,4-dihydroisoquinolinyl; cyclopropyl optionally substituted with phenyl; pyrrolidinyl optionally substituted with methyl; —$CH_2$-pyrrolidinyl optionally substituted with —$CH_3$; —($C_1$-$C_3$)alkyl-piperidinyl optionally substituted with —($C_1$-$C_3$)alkyl, —C(O)—($C_1$-$C_3$)alkyl, or —C(O)C($CH_3$)$_3$; and -cyclopentyl-phenyl;
$R^4$ is H or —($C_1$-$C_3$)alkyl,
or $R^3$ and $R^4$, together with the nitrogen atom to which they are attached, form dihydroisoquinolinyl, morpholinyl, piperidinyl, pyrrolidinyl or piperizinyl, wherein the piperidinyl, pyrrolidinyl and piperizinyl are each optionally substituted with —C(O)—$CH_3$,
—$SO_2$—$CH_3$, piperidinyl, pyrrolidinyl, phenyl, —($C_1$-$C_3$)alkyl, or —$CH_2$—$NH_2$;
$R^6$ is H; and
$R^7$ is H.
9. A compound of Formula III:

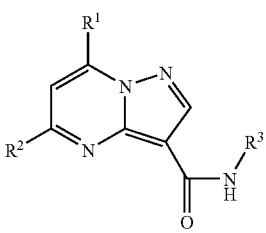

or a pharmaceutically acceptable salt thereof, wherein:
$R^1$ is —OH or —$OCH_3$;
$R^2$ is independently selected from —$CH_3$, phenyl optionally substituted with 1-3 groups independently selected from halo, —$CF_3$, —$OCH_3$; and —($C_1$-$C_3$)alkyl; furanyl and pyridinyl optionally substituted with methyl;
$R^3$ is selected from —$CH_2$-phenyl optionally substituted with 1-3 substituents independently selected from —$OCH_3$, halo, phenyl, —S—$CH_3$, —O-phenyl, —$CH_3$, —$CF_3$, —($C_1$-$C_6$)alkyl, piperizinyl optionally substituted with —($C_1$-$C_3$)alkyl, morpholinyl, and —$CH_2$-piperidine optionally substituted with —($C_1$-$C_3$)alkyl; —($C_1$-$C_3$)alkylmorpholinyl; —($C_1$-$C_3$)alkyl-piperidinyl optionally substituted with —($C_1$-$C_3$)alkyl; -piperidinyl optionally substituted with —($C_1$-$C_3$)alkyl; —($C_1$-$C_3$)alkyl-piperizinyl optionally substituted with —($C_1$-$C_3$)alkyl; piperidinyl optionally substituted with —$SO_2CH_3$, -piperizinyl optionally substituted with —($C_1$-$C_3$)alkyl.
10. A compound according to claim 1 selected from:
N-(biphenyl-4-ylmethyl)-7-hydroxy-5-methylpyrazolo[1,5-a]pyrimidine-3-carboxamide;
N-[(2-bromophenyl)methyl]-7-hydroxy-5-methylpyrazolo[1,5-a]pyrimidine-3-carboxamide;
7-hydroxy-5-methyl-N-[(3-nitrophenyl)methyl]pyrazolo[1,5-a]pyrimidine-3-carboxamide;
N-[(3-bromophenyl)methyl]-7-hydroxy-5-methylpyrazolo[1,5-a]pyrimidine-3-carboxamide;
7-hydroxy-5-methyl-N-[(2-nitrophenyl)methyl]pyrazolo[1,5-a]pyrimidine-3-carboxamide;
7-hydroxy-N-[(4-iodophenyl)methyl]-5-methylpyrazolo[1,5-a]pyrimidine-3-carboxamide;
7-hydroxy-5-methyl-N-{[2-(methylthio)phenyl]methyl}pyrazolo[1,5-a]pyrimidine-3-carboxamide;
7-hydroxy-5-methyl-N-{[3-(phenyloxy)phenyl]methyl}pyrazolo[1,5-a]pyrimidine-3-carboxamide;
7-hydroxy-5-methyl-N-{[4-(phenyloxy)phenyl]methyl}pyrazolo[1,5-a]pyrimidine-3-carboxamide;
7-hydroxy-5-phenyl-N-(phenylmethyl)pyrazolo[1,5-a]pyrimidine-3-carboxamide;
5-ethyl-7-hydroxy-N-(phenylmethyl)pyrazolo[1,5-a]pyrimidine-3-carboxamide;
7-hydroxy-5-methyl-N-[(3-methylphenyl)methyl]pyrazolo[1,5-a]pyrimidine-3-carboxamide;
7-hydroxy-N-[(3-iodophenyl)methyl]-5-methylpyrazolo[1,5-a]pyrimidine-3-carboxamide;
7-hydroxy-5-methyl-N-{[3-(trifluoromethyl)phenyl]methyl}pyrazolo[1,5-a]pyrimidine-3-carboxamide;
7-hydroxy-5-(1-methylethyl)-N-(phenylmethyl)pyrazolo[1,5-a]pyrimidine-3-carboxamide;
7-hydroxy-N-(phenylmethyl)-5-pyridin-2-ylpyrazolo[1,5-a]pyrimidine-3-carboxamide;
N-cyclohexyl-7-hydroxy-5-methylpyrazolo[1,5-a]pyrimidine-3-carboxamide;
5-furan-3-yl-7-hydroxy-N-(phenylmethyl)pyrazolo[1,5-a]pyrimidine-3-carboxamide;
ethyl N-[(7-hydroxy-5-methylpyrazolo[1,5-a]pyrimidin-3-yl)carbonyl]-L-phenylalaninate;
phenylmethyl 7-hydroxy-5-phenylpyrazolo[1,5-a]pyrimidine-3-carboxylate;
7-hydroxy-N-{[4-(methyloxy)phenyl]methyl}-5-phenylpyrazolo[1,5-a]pyrimidine-3-carboxamide;
N,N-diethyl-7-hydroxy-5-phenylpyrazolo[1,5-a]pyrimidine-3-carboxamide;
N-cyclohexyl-7-hydroxy-5-phenylpyrazolo[1,5-a]pyrimidine-3-carboxamide;
N-ethyl-7-hydroxy-5-phenylpyrazolo[1,5-a]pyrimidine-3-carboxamide;
5-phenyl-3-[(4-phenylpiperazin-1-yl)carbonyl]pyrazolo[1,5-a]pyrimidin-7-ol;

N-cyclopentyl-7-hydroxy-5-phenylpyrazolo[1,5-a]pyrimidine-3-carboxamide;
7-hydroxy-N-{[2-(methyloxy)phenyl]methyl}-5-phenylpyrazolo[1,5-a]pyrimidine-3-carboxamide;
7-hydroxy-N-[(3-methylphenyl)methyl]-5-phenylpyrazolo[1,5-a]pyrimidine-3-carboxamide;
7-hydroxy-N-[(4-methylphenyl)methyl]-5-phenylpyrazolo[1,5-a]pyrimidine-3-carboxamide;
7-hydroxy-N-[(2-methylphenyl)methyl]-5-phenylpyrazolo[1,5-a]pyrimidine-3-carboxamide;
N-[(2-bromophenyl)methyl]-7-hydroxy-5-phenylpyrazolo[1,5-a]pyrimidine-3-carboxamide;
N-[(3-bromophenyl)methyl]-7-hydroxy-5-phenylpyrazolo[1,5-a]pyrimidine-3-carboxamide;
N-[(4-bromophenyl)methyl]-7-hydroxy-5-phenylpyrazolo[1,5-a]pyrimidine-3-carboxamide;
5-(4-fluorophenyl)-7-hydroxy-N-(phenylmethyl)pyrazolo[1,5-a]pyrimidine-3-carboxamide;
5-(2-fluorophenyl)-7-hydroxy-N-(phenylmethyl)pyrazolo[1,5-a]pyrimidine-3-carboxamide;
7-hydroxy-N-(2-morpholin-4-ylethyl)-5-phenylpyrazolo[1,5-a]pyrimidine-3-carboxamide;
3-[(4-methylpiperazin-1-yl)carbonyl]-5-phenylpyrazolo[1,5-a]pyrimidin-7-ol;
7-hydroxy-N-methyl-5-phenylpyrazolo[1,5-a]pyrimidine-3-carboxamide;
5-phenyl-3-(piperidin-1-ylcarbonyl)pyrazolo[1,5-a]pyrimidin-7-ol;
3-(3,4-dihydroisoquinolin-2(1H)-ylcarbonyl)-5-phenylpyrazolo[1,5-a]pyrimidin-7-ol;
7-hydroxy-N-(3-morpholin-4-ylpropyl)-5-phenylpyrazolo[1,5-a]pyrimidine-3-carboxamide;
7-hydroxy-N-methyl-N-(1-methylpiperidin-4-yl)-5-phenylpyrazolo[1,5-a]pyrimidine-3-carboxamide;
N-cyclopropyl-7-hydroxy-5-phenylpyrazolo[1,5-a]pyrimidine-3-carboxamide;
7-hydroxy-N-[(3-endo)-8-methyl-8-azabicyclo[3.2.1]oct-3-yl]-5-phenylpyrazolo[1,5-a]pyrimidine-3-carboxamide;
5-[2-bromo-5-(methyloxy)phenyl]-7-hydroxy-N-(phenylmethyl)pyrazolo[1,5-a]pyrimidine-3-carboxamide;
7-hydroxy-5-phenyl-N-{[4-(phenyloxy)phenyl]methyl}pyrazolo[1,5-a]pyrimidine-3-carboxamide;
5-(3-bromophenyl)-7-hydroxy-N-(phenylmethyl)pyrazolo[1,5-a]pyrimidine-3-carboxamide;
7-hydroxy-N-(phenylmethyl)-5-pyridin-4-ylpyrazolo[1,5-a]pyrimidine-3-carboxamide;
5-(3-chlorophenyl)-7-hydroxy-N-(phenylmethyl)pyrazolo[1,5-a]pyrimidine-3-carboxamide;
5-(4-chlorophenyl)-7-hydroxy-N-(phenylmethyl)pyrazolo[1,5-a]pyrimidine-3-carboxamide;
7-hydroxy-5-phenyl-N-(2-phenylethyl)pyrazolo[1,5-a]pyrimidine-3-carboxamide;
ethyl N-[(7-hydroxy-5-phenylpyrazolo[1,5-a]pyrimidin-3-yl)carbonyl]-L-phenylalaninate;
7-hydroxy-N,5-diphenylpyrazolo[1,5-a]pyrimidine-3-carboxamide;
N-(cyclopropylmethyl)-7-hydroxy-5-phenylpyrazolo[1,5-a]pyrimidine-3-carboxamide;
N-(1,1-dimethylethyl)-7-hydroxy-5-phenylpyrazolo[1,5-a]pyrimidine-3-carboxamide;
7-hydroxy-N-(2-methylpropyl)-5-phenylpyrazolo[1,5-a]pyrimidine-3-carboxamide;
7-hydroxy-N-(3-methylbutyl)-5-phenylpyrazolo[1,5-a]pyrimidine-3-carboxamide;
N-(2,2-dimethylpropyl)-7-hydroxy-5-phenylpyrazolo[1,5-a]pyrimidine-3-carboxamide;
7-hydroxy-5-phenyl-N-(2-piperidin-1-ylethyl)pyrazolo[1,5-a]pyrimidine-3-carboxamide;
7-hydroxy-5-phenyl-N-piperidin-4-ylpyrazolo[1,5-a]pyrimidine-3-carboxamide;
7-hydroxy-5-phenylpyrazolo[1,5-a]pyrimidine-3-carboxamide;
7-hydroxy-N-(1-methylethyl)-5-phenylpyrazolo[1,5-a]pyrimidine-3-carboxamide;
3-(morpholin-4-ylcarbonyl)-5-phenylpyrazolo[1,5-a]pyrimidin-7-ol;
7-hydroxy-5-phenyl-N-[(1S,2R)-2-phenylcyclopropyl]pyrazolo[1,5-a]pyrimidine-3-carboxamide;
7-hydroxy-5-[4-(methyloxy)phenyl]-N-(phenylmethyl)pyrazolo[1,5-a]pyrimidine-3-carboxamide;
5-(3-fluorophenyl)-7-hydroxy-N-(phenylmethyl)pyrazolo[1,5-a]pyrimidine-3-carboxamide;
7-hydroxy-5-phenyl-N-(1-phenylethyl)pyrazolo[1,5-a]pyrimidine-3-carboxamide;
7-hydroxy-N-methyl-5-phenyl-N-(phenylmethyl)pyrazolo[1,5-a]pyrimidine-3-carboxamide;
1,1-dimethylethyl 4-({[(7-hydroxy-5-phenylpyrazolo[1,5-a]pyrimidin-3-yl)carbonyl]amino}methyl)piperidine-1-carboxylate;
7-hydroxy-5-phenyl-N-(piperidin-4-ylmethyl)pyrazolo[1,5-a]pyrimidine-3-carboxamide;
7-hydroxy-5-phenyl-N-(pyrrolidin-3-ylmethyl)pyrazolo[1,5-a]pyrimidine-3-carboxamide;
N-[(1-acetylpiperidin-4-yl)methyl]-7-hydroxy-5-phenylpyrazolo[1,5-a]pyrimidine-3-carboxamide;
7-hydroxy-N-(phenylmethyl)-5-[3-(trifluoromethyl)phenyl]pyrazolo[1,5-a]pyrimidine-3-carboxamide;
7-hydroxy-5-(4-hydroxyphenyl)-N-(phenylmethyl)pyrazolo[1,5-a]pyrimidine-3-carboxamide;
5-(3-chloro-4-fluorophenyl)-7-hydroxy-N-(phenylmethyl)pyrazolo[1,5-a]pyrimidine-3-carboxamide;
5-(2,5-difluorophenyl)-7-hydroxy-N-(phenylmethyl)pyrazolo[1,5-a]pyrimidine-3-carboxamide;
5-(2,4-difluorophenyl)-7-hydroxy-N-(phenylmethyl)pyrazolo[1,5-a]pyrimidine-3-carboxamide;
5-(3,5-difluorophenyl)-7-hydroxy-N-(phenylmethyl)pyrazolo[1,5-a]pyrimidine-3-carboxamide;
7-hydroxy-5-phenyl-N-pyrrolidin-3-ylpyrazolo[1,5-a]pyrimidine-3-carboxamide;
5-phenyl-3-(piperazin-1-ylcarbonyl)pyrazolo[1,5-a]pyrimidin-7-ol;
3-[(4-acetylpiperazin-1-yl)carbonyl]-5-phenylpyrazolo[1,5-a]pyrimidin-7-ol;
3-{[4-(methylsulfonyl)piperazin-1-yl]carbonyl}-5-phenylpyrazolo[1,5-a]pyrimidin-7-ol;
N-(1-acetylpiperidin-4-yl)-7-hydroxy-5-phenylpyrazolo[1,5-a]pyrimidine-3-carboxamide;
7-hydroxy-N-[1-(methylsulfonyl)piperidin-4-yl]-5-phenylpyrazolo[1,5-a]pyrimidine-3-carboxamide;
7-hydroxy-N-[(1-methylpiperidin-4-yl)methyl]-5-phenylpyrazolo[1,5-a]pyrimidine-3-carboxamide;
7-hydroxy-N-(1-methylpyrrolidin-3-yl)-5-phenylpyrazolo[1,5-a]pyrimidine-3-carboxamide;
7-hydroxy-N-[(2-morpholin-4-ylphenyl)methyl]-5-phenylpyrazolo[1,5-a]pyrimidine-3-carboxamide;
7-hydroxy-N-[1-(methylsulfonyl)pyrrolidin-3-yl]-5-phenylpyrazolo[1,5-a]pyrimidine-3-carboxamide;
3-[(4-ethylpiperazin-1-yl)carbonyl]-5-phenylpyrazolo[1,5-a]pyrimidin-7-ol;
3-{[4(1-methylethyl)piperazin-1-yl]carbonyl}-5-phenylpyrazolo[1,5-a]pyrimidin-7-ol;
7-hydroxy-N-(1-methylpiperidin-4-yl)-5-phenylpyrazolo[1,5-a]pyrimidine-3-carboxamide;

5-(3,4-difluorophenyl)-7-hydroxy-N-(phenylmethyl)pyrazolo[1,5-a]pyrimidine-3-carboxamide;
5-(2,3-difluorophenyl)-7-hydroxy-N-(phenylmethyl)pyrazolo[1,5-a]pyrimidine-3-carboxamide;
7-hydroxy-N-(phenylmethyl)-5-[4-(trifluoromethyl)phenyl]pyrazolo[1,5-a]pyrimidine-3-carboxamide;
3-(1,4'-bipiperidin-1'-ylcarbonyl)-5-phenylpyrazolo[1,5-a]pyrimidin-7-ol;
5-phenyl-3-[(4-pyrrolidin-1-ylpiperidin-1-yl)carbonyl]pyrazolo[1,5-a]pyrimidin-7-ol;
7-hydroxy-N-(phenylmethyl)-5-(2,4,5-trifluorophenyl)pyrazolo[1,5-a]pyrimidine-3-carboxamide;
5-(2,4-difluorophenyl)-N-[(1-ethylpiperidin-4-yl)methyl]-7-hydroxypyrazolo[1,5-a]pyrimidine-3-carboxamide;
5-(3-chloro-4-fluorophenyl)-N-[(1-ethylpiperidin-4-yl)methyl]-7-hydroxypyrazolo[1,5-a]pyrimidine-3-carboxamide;
5-(4-fluorophenyl)-7-hydroxy-N-{[1-(1-methylethyl)piperidin-4-yl]methyl}pyrazolo[1,5-a]pyrimidine-3-carboxamide;
5-(4-fluorophenyl)-7-hydroxy-N-[(1-methylpiperidin-4-yl)methyl]pyrazolo[1,5-a]pyrimidine-3-carboxamide;
N-[(1-ethylpiperidin-4-yl)methyl]-5-(4-fluorophenyl)-7-hydroxypyrazolo[1,5-a]pyrimidine-3-carboxamide;
7-hydroxy-N-{[1-(2-methylpropyl)piperidin-4-yl]methyl}-5-phenylpyrazolo[1,5-a]pyrimidine-3-carboxamide;
N-[(1-ethylpiperidin-4-yl)methyl]-7-hydroxy-5-phenylpyrazolo[1,5-a]pyrimidine-3-carboxamide;
7-hydroxy-N-{[1-(1-methylethyl)piperidin-4-yl]methyl}-5-phenylpyrazolo[1,5-a]pyrimidine-3-carboxamide;
7-hydroxy-N-{[4-(4-methylpiperazin-1-yl)phenyl]methyl}-5-phenylpyrazolo[1,5-a]pyrimidine-3-carboxamide;
5-(2,4-difluorophenyl)-7-hydroxy-N-[(1-methylpiperidin-4-yl)methyl]pyrazolo[1,5-a]pyrimidine-3-carboxamide;
5-(2,4-difluorophenyl)-7-hydroxy-N-{[1-(2-methylpropyl)piperidin-4-yl]methyl}pyrazolo[1,5-a]pyrimidine-3-carboxamide;
5-(4-fluorophenyl)-7-hydroxy-N-{[1-(2-methylpropyl)piperidin-4-yl]methyl}pyrazolo[1,5-a]pyrimidine-3-carboxamide;
5-(2,4-difluorophenyl)-7-hydroxy-N-{[1-(2-methylethyl)piperidin-4-yl]methyl}pyrazolo[1,5-a]pyrimidine-3-carboxamide;
5-(3-chloro-4-fluorophenyl)-7-hydroxy-N-{[1-(1-methylethyl)piperidin-4-yl]methyl}pyrazolo[1,5-a]pyrimidine-3-carboxamide;
N-[(1-ethylpyrrolidin-2-yl)methyl]-7-hydroxy-5-phenylpyrazolo[1,5-a]pyrimidine-3-carboxamide;
7-hydroxy-N-[(1-methylpiperidin-2-yl)methyl]-5-phenylpyrazolo[1,5-a]pyrimidine-3-carboxamide;
7-hydroxy-N-[(1-methylpiperidin-3-yl)methyl]-5-phenylpyrazolo[1,5-a]pyrimidine-3-carboxamide;
7-hydroxy-N-[(1-methylpyrrolidin-2-yl)methyl]-5-phenylpyrazolo[1,5-a]pyrimidine-3-carboxamide;
5-(3-chloro-4-fluorophenyl)-7-hydroxy-N-[(1-methylpiperidin-4-yl)methyl]pyrazolo[1,5-a]pyrimidine-3-carboxamide;
7-hydroxy-N-[(1-methylpyrrolidin-3-yl)methyl]-5-phenylpyrazolo[1,5-a]pyrimidine-3-carboxamide;
7-hydroxy-N-{[2-(4-methylpiperazin-1-yl)phenyl]methyl}-5-phenylpyrazolo[1,5-a]pyrimidine-3-carboxamide; and,
7-hydroxy-N-{[3-(4-methylpiperazin-1-yl)phenyl]methyl}-5-phenylpyrazolo[1,5-a]pyrimidine-3-carboxamide; and or a pharmaceutically acceptable salt thereof.

11. A compound that is
N-[3-(dimethylamino)propyl]-7-hydroxy-5-phenylpyrazolo[1,5-a]pyrimidine-3-carboxamide;
3-{[4-(aminomethyl)piperidin-1-yl]carbonyl}-5-phenylpyrazolo[1,5-a]pyrimidin-7-ol, or a pharmaceutically acceptable salt thereof.

12. A pharmaceutical composition comprising the compound according to claim 1 and a pharmaceutically acceptable carrier, excipient, or diluent.

\* \* \* \* \*